US012734212B2

(12) United States Patent
Lee et al.

(10) Patent No.: US 12,734,212 B2
(45) Date of Patent: Sep. 15, 2026

(54) **COMPOSITION FOR PREVENTION OR TREATMENT OF *STAPHYLOCOCCUS AUREUS* INFECTIOUS DISEASE**

(71) Applicants: CLIPSBNC CO., LTD., Seoul (KR); PUSAN NATIONAL UNIVERSITY INDUSTRY-UNIVERSITY COOPERATION FOUNDATION, Busan (KR)

(72) Inventors: Bok Luel Lee, Busan (KR); Dong Ho Ahn, Seoul (KR)

(73) Assignees: CLIPSBNC CO., LTD., Seoul (KR); PUSAN NATIONAL UNIVERSITY INDUSTRY-UNIVERSITY COOPERATION FOUNDATION, Busan (KR)

( * ) Notice: Subject to any disclaimer, the term of this patent is extended or adjusted under 35 U.S.C. 154(b) by 556 days.

(21) Appl. No.: 18/024,800

(22) PCT Filed: Sep. 8, 2021

(86) PCT No.: PCT/KR2021/012222
§ 371 (c)(1),
(2) Date: Mar. 6, 2023

(87) PCT Pub. No.: WO2022/055252
PCT Pub. Date: Mar. 17, 2022

(65) Prior Publication Data
US 2023/0310543 A1 Oct. 5, 2023

(30) Foreign Application Priority Data
Sep. 8, 2020 (KR) ........................ 10-2020-0114435

(51) Int. Cl.

| | |
|---|---|
| ***A61K 39/02*** | (2006.01) |
| ***A61K 38/16*** | (2006.01) |
| ***A61K 39/00*** | (2006.01) |
| ***A61K 39/085*** | (2006.01) |
| ***A61P 31/04*** | (2006.01) |

(52) U.S. Cl.
CPC ............ *A61K 38/164* (2013.01); *A61K 39/00* (2013.01); *A61P 31/04* (2018.01)

(58) Field of Classification Search
None
See application file for complete search history.

(56) References Cited

U.S. PATENT DOCUMENTS

| | | | |
|---|---|---|---|
| 2008/0131457 | A1 | 6/2008 | Taylor et al. |
| 2009/0053235 | A1 | 2/2009 | Taylor et al. |
| 2011/0027265 | A1 | 2/2011 | Bubeck-Wardenburg et al. |
| 2015/0086539 | A1 | 3/2015 | Nagy et al. |
| 2015/0165015 | A1 | 6/2015 | Taylor et al. |
| 2018/0221466 | A9 | 8/2018 | Taylor et al. |

FOREIGN PATENT DOCUMENTS

| | | | |
|---|---|---|---|
| CN | 109384844 | A | 2/2019 |
| KR | 10-2015-0035587 | A | 4/2015 |
| KR | 10-2017-0136637 | A | 12/2017 |
| WO | 00/12131 | A1 | 3/2000 |
| WO | 2007/1 45689 | A1 | 12/2007 |
| WO | 2009/029831 | A1 | 3/2009 |
| WO | 2013/156534 | A1 | 10/2013 |
| WO | 2013/156534 | A9 | 10/2013 |

OTHER PUBLICATIONS

Shweta Kailasan et al., "Rational Design of Toxoid Vaccine Candidates for *Staphylococcus aureus* Leukocidin AB (LukAB)", Toxins, 2019, pp. 1-21, vol. 11, No. 339.

Ashley L. Dumont et al., "Identification of a Crucial Residue Required for *Staphylococcus aureus* LukAB Cytotoxicity and Receptor Recognition", Infection and Immunity, Mar. 2014, pp. 1268-1276, vol. 82, No. 3.

John Vernachio et al., "Anti-Clumping Factor A Immunoglobulin Reduces the Duration of Methicillin-Resistant *Staphylococcus aureus* Bacteremia in an Experimental Model of Infective Endocarditis", Antimicrobial Agents and Chemotherapy, Nov. 2003, pp. 3400-3406, vol. 47, No. 11.

Alice G. Cheng et al., "Contribution of Coagulases towards *Staphylococcus aureus* Disease and Protective Immunity", PLoS Pathogens, Aug. 2010, pp. 1-18, vol. 6, Issue 8, e1001036.

International Search Report of PCT/KR2021/012222 dated Dec. 21, 2021 [PCT/ISA/210].

Zhang Qingfeng, "Inhibition of five bi-component leukocidins-mediated human PMN lysis is by the combination of three antibodies to *S. aureus* LukS, HlgA and $LukA_{E323A}B$", Feb. 2021, Department of Manufacturing Pharmacy, The Graduate School Pusan National University, pp. 1-42 (52 pages).

Michael L. Landrum et al., "Safety and immunogenicity of a recombinant *Staphylococcus aureus* α-toxoid and a recombinant Panton-Valentine Leukocidin subunit, in healthy adults", 2017, Human Vaccines & Immunotherapeutics, vol. 13, No. 4, 791-801 (11 pages).

Partial Supplementary European Search Report dated Sep. 30, 2024 in Application No. 21867117.0.

Japanese Office Action dated Nov. 5, 2024 in Application No. 2023-515623.

Korean Office Action dated Sep. 12, 2024 in Application No. 10-2021-0119782.

*Primary Examiner* — Jennifer E Graser
(74) *Attorney, Agent, or Firm* — Sughrue Mion, PLLC

(57) ABSTRACT

A composition for prevention or treatment of a *Staphylococcus aureus* infectious disease and a composition for prevention or treatment of a thrombotic disorder caused by *Staphylococcus aureus* infection are disclosed. Cell lysis by 11 toxins of *Staphylococcus aureus* can be thoroughly inhibited by using the cross-reactivity of antibodies against *Staphylococcus aureus* toxins, even with a minimal combination of antigens. The composition can be used as an effective therapeutic composition that can comprehensively remove or alleviate comprehensive pathological conditions caused by infection, away from piecemeal amelioration of individual symptoms caused by *Staphylococcus aureus* infection, by inducing opsonophagocytosis and effectively controlling blood coagulation in infected individuals.

7 Claims, 41 Drawing Sheets

Specification includes a Sequence Listing.

kbp
3
1
0.5
1 2 3 4 5 6 7
LukS-PV
LukF-PV
HlgA
HlgB
HlgC
LukE
LukD
Band size: 1.1 Kbp (lane: 1, 3~7)
Band size: 1.2 Kbp (lane: 2)

kbp
3
2
1
LukAB
Band size: 2.1 Kbp kbp
3
2
1
Hla
Band size: 1.1 kbp kbp
3
2
1
Hla H35L
Band size: 1.1 kbp kbp
3
2
1
LukS T244A
Band size: 1.1 kbp kbp
3
2
1
LukA E323A B
Band size: 2.1 kbp

[FIG. 2]
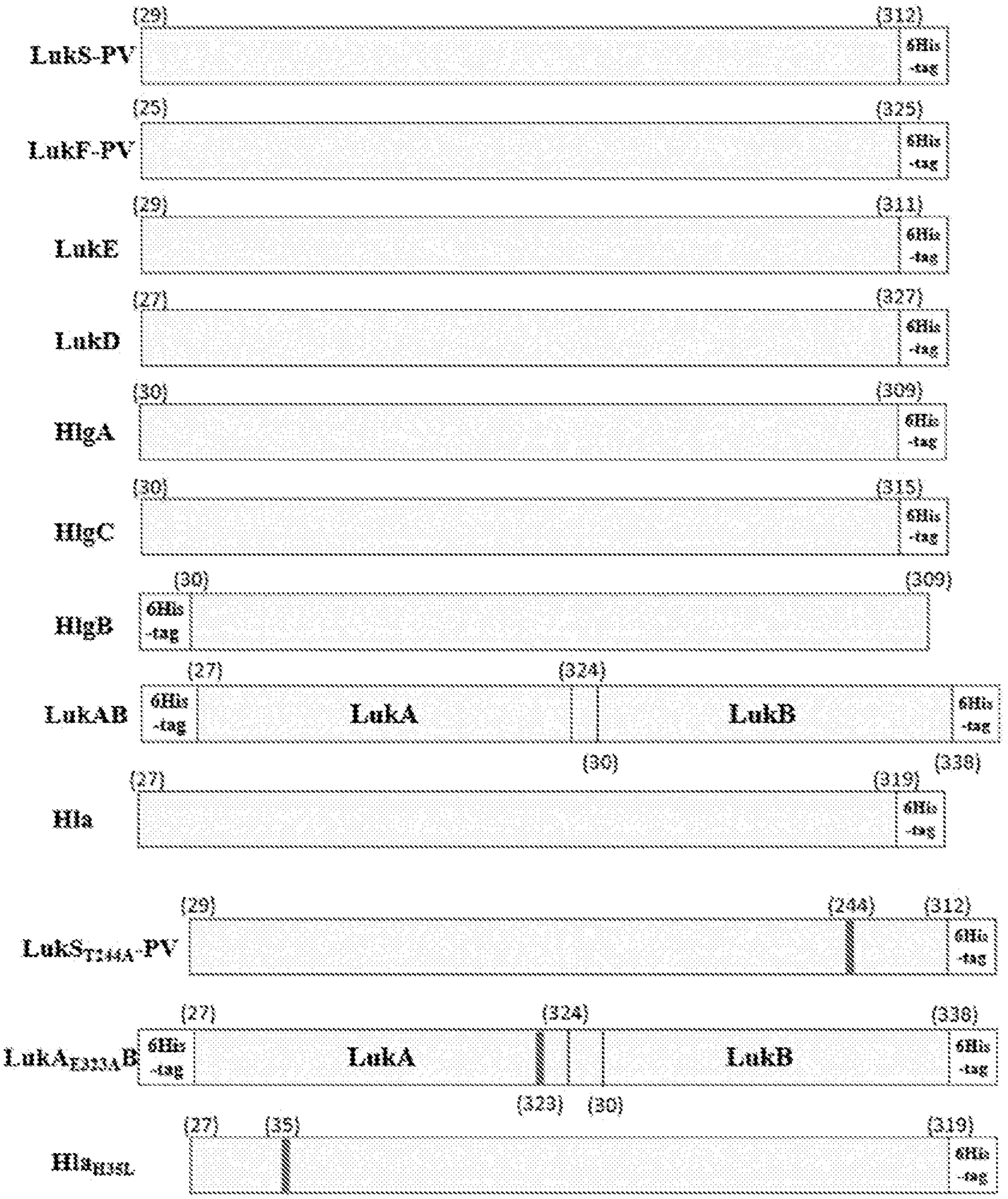

[FIG. 3a]
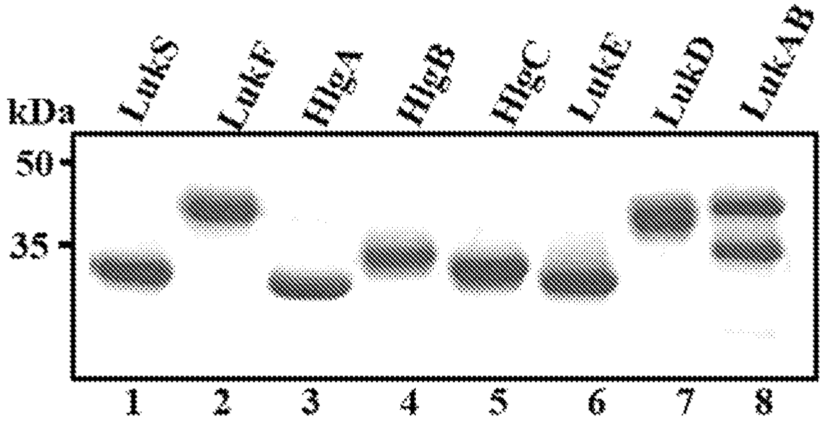
[FIG. 3b]
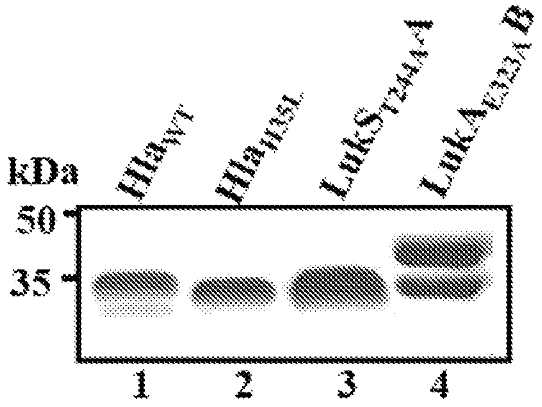

[FIG. 3c]
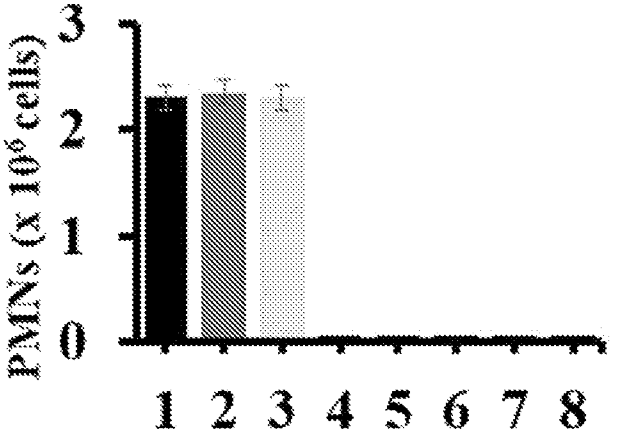
1: No toxin
2:LukS$_{T244A}$-PV+LukF-PV
3:LukA$_{E323A}$B
4:LukS-PV+LukF-PV
5:LukE+LukD
6:HlgC+HlgB
7:HlgA+HlgB
8:LukAB
[FIG. 3d]
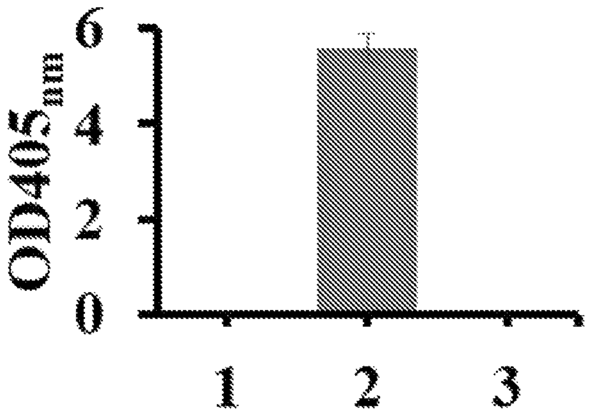
1: PBS
2: Hla$_{WT}$
3: Hla$_{H35L}$

[FIG. 4]
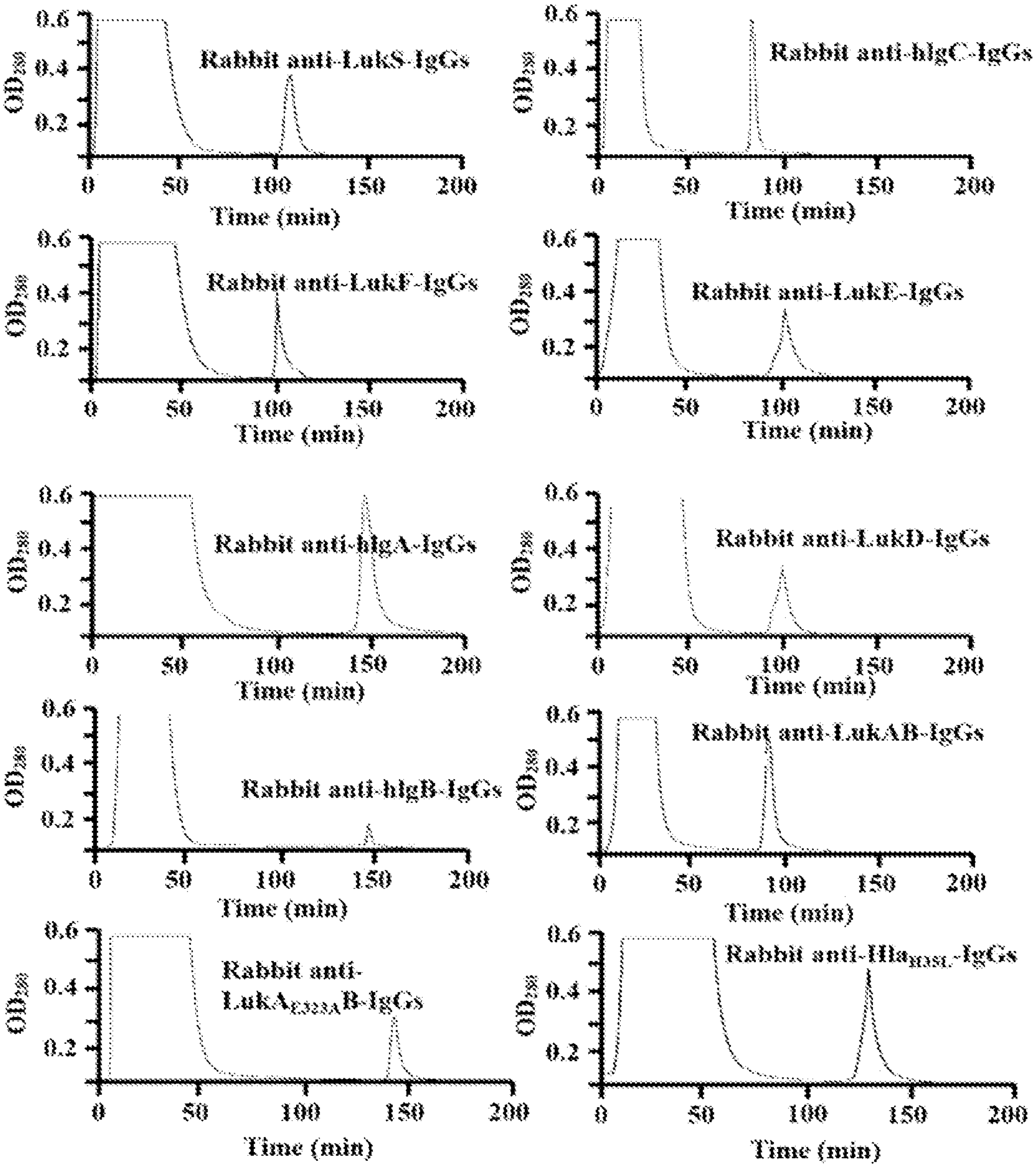

[FIG. 5]
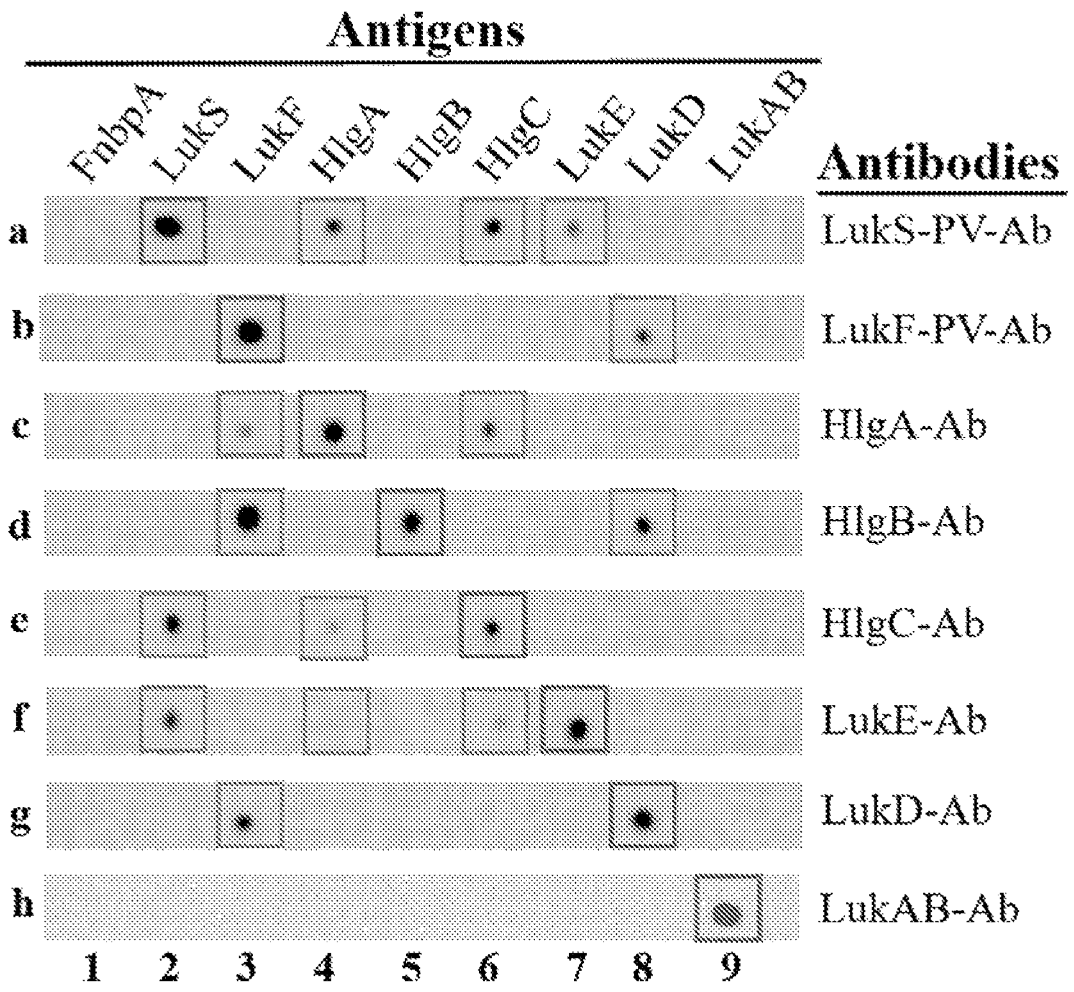

PMNs survival (%)
100
50
0
1 2 3 4 5 6
anti-LukS-PV-IgG 100
50
0
1 2 3 4 5 6
anti-HlgA-IgG PMNs survival (%)
100
50
0
1 2 3 4 5 6
anti-HlgC-IgG 100
50
0
1 2 3 4 5 6
anti-LukE-IgG PMNs survival (%)
100
50
0
1 2 3 4 5 6
anti-LukE+LukD-IgGs 100
50
0
1 2 3 4 5 6
anti-HlgA+HlgB-IgGs PMNs survival (%)
100
50
0
1 2 3 4 5 6
anti-HlgC+HlgB-IgGs 100
50
0
1 2 3 4 5 6
anti-LukS+LukF-PV-IgGs

[FIG. 12]
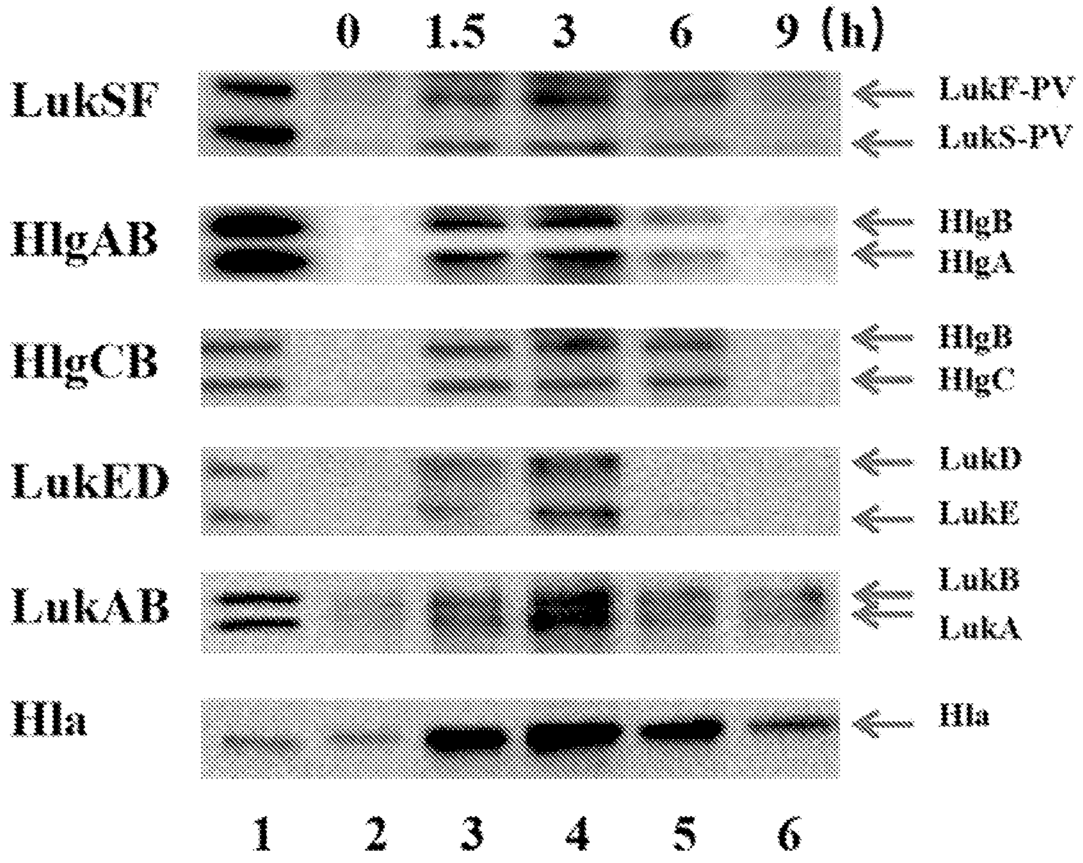

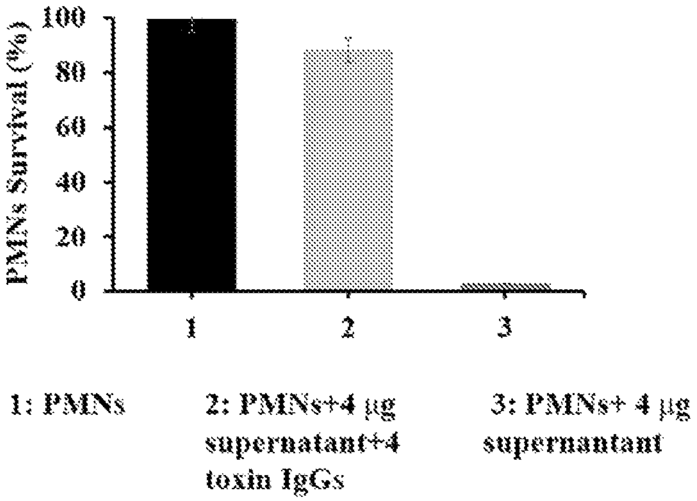
[FIG. 14b]
1: PMNs 2: PMNs+4 μg supernatant+4 toxin IgGs 3: PMNs+ 4 μg supernatant
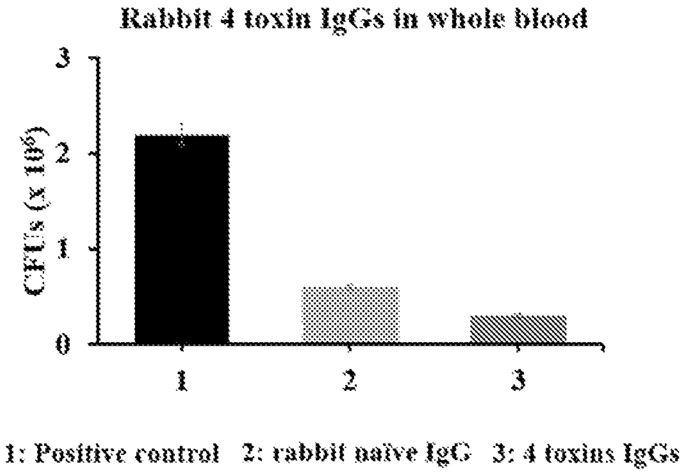
[FIG. 15]
1: Positive control 2: rabbit naive IgG 3: 4 toxins IgGs
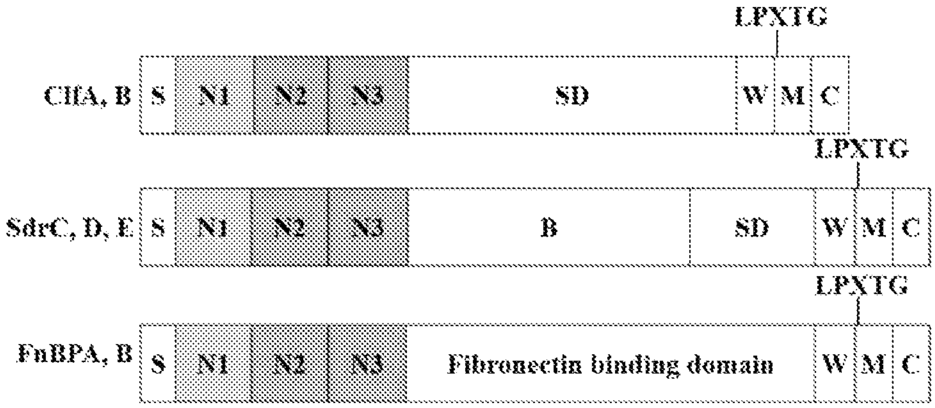
[FIG. 16a]

[FIG. 16b]
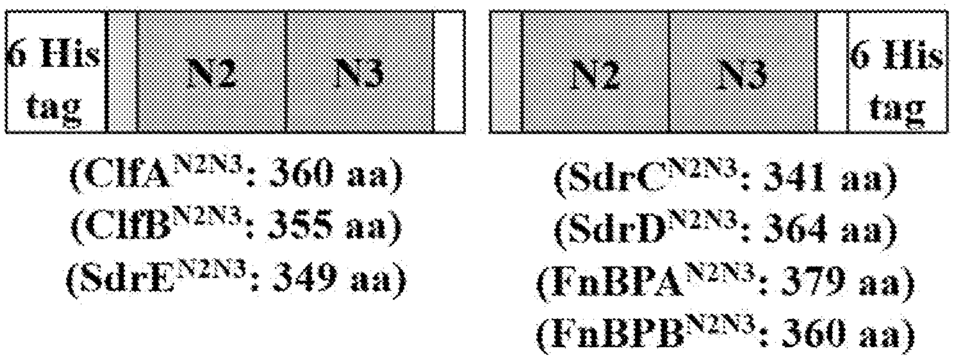
[FIG. 16c]
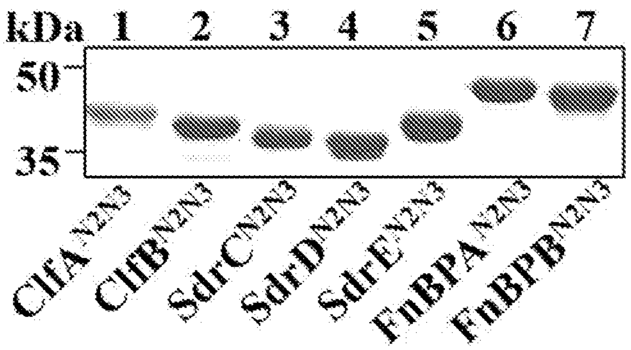
[FIG. 17a]
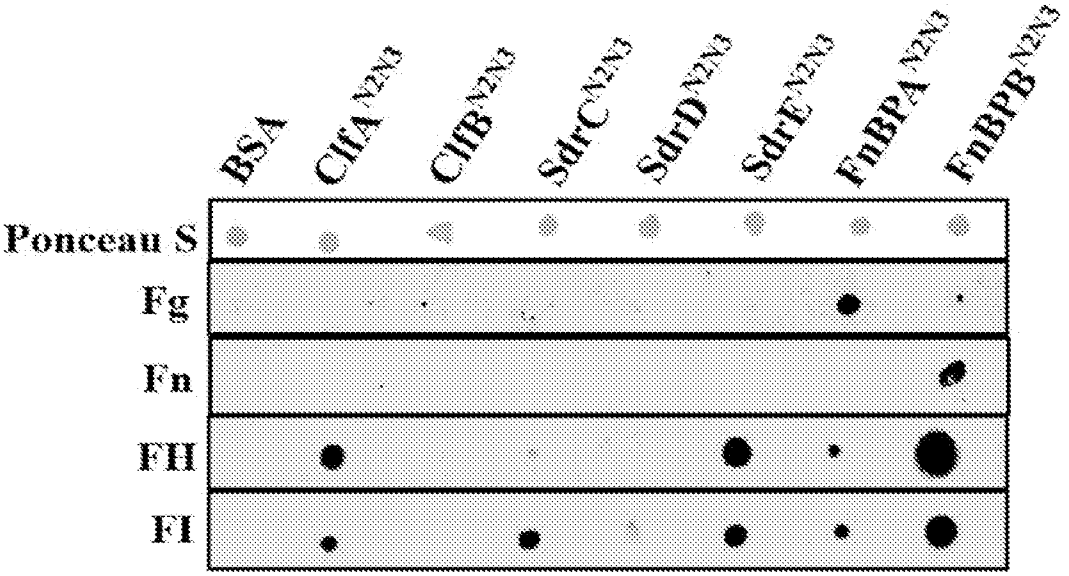

[FIG. 17b]
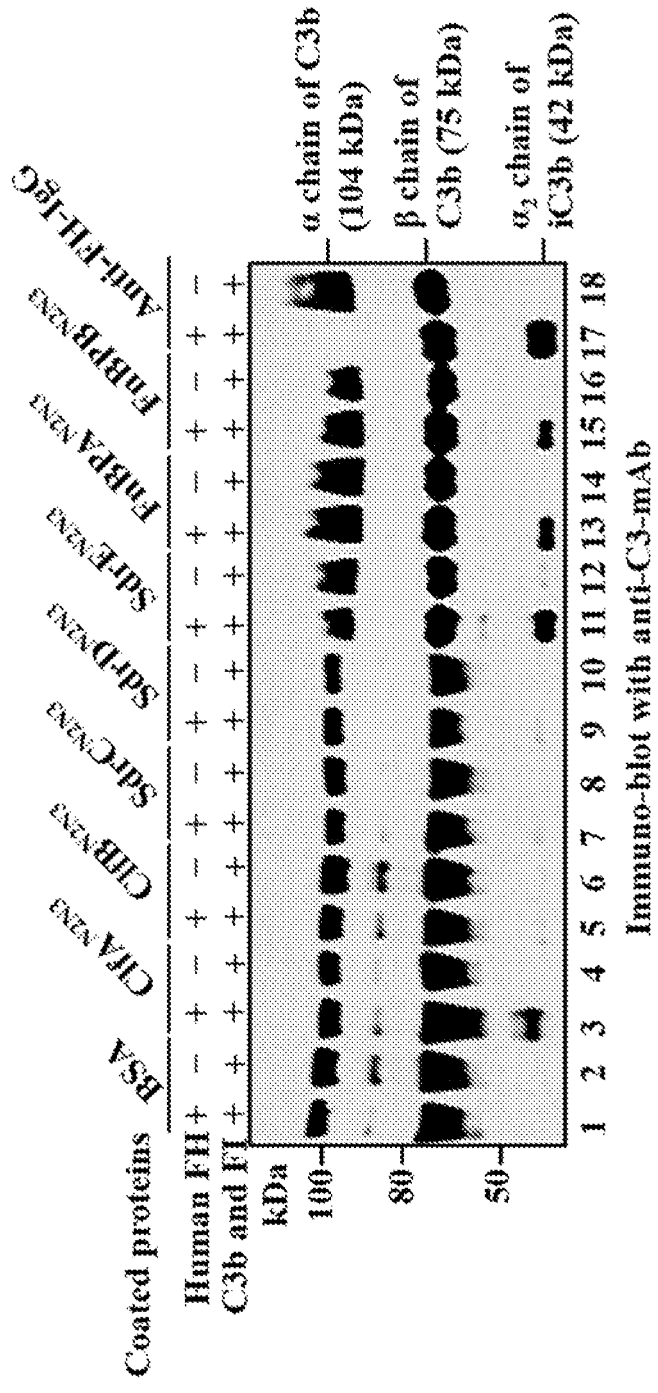

[FIG. 18a]
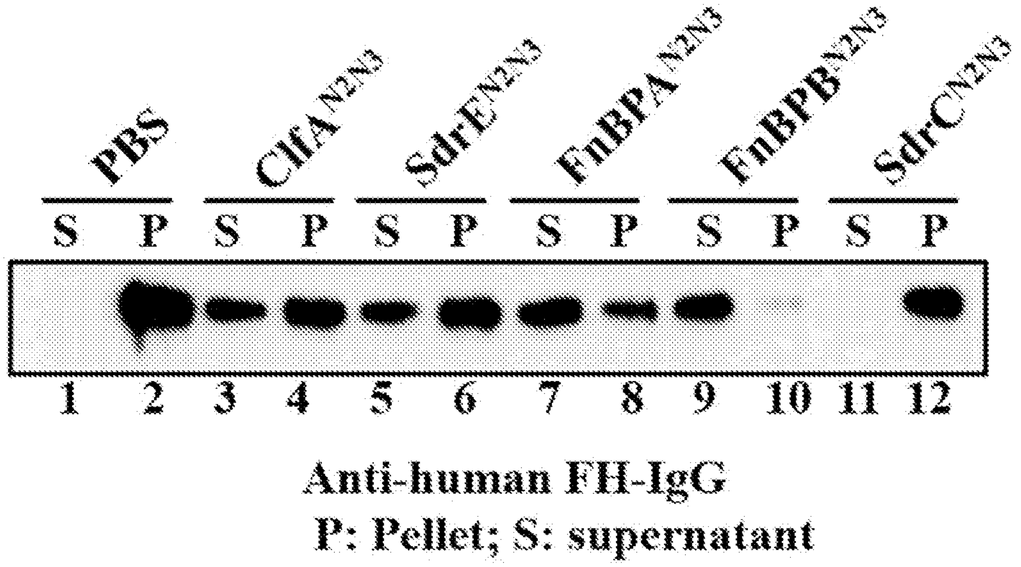
[FIG. 18b]
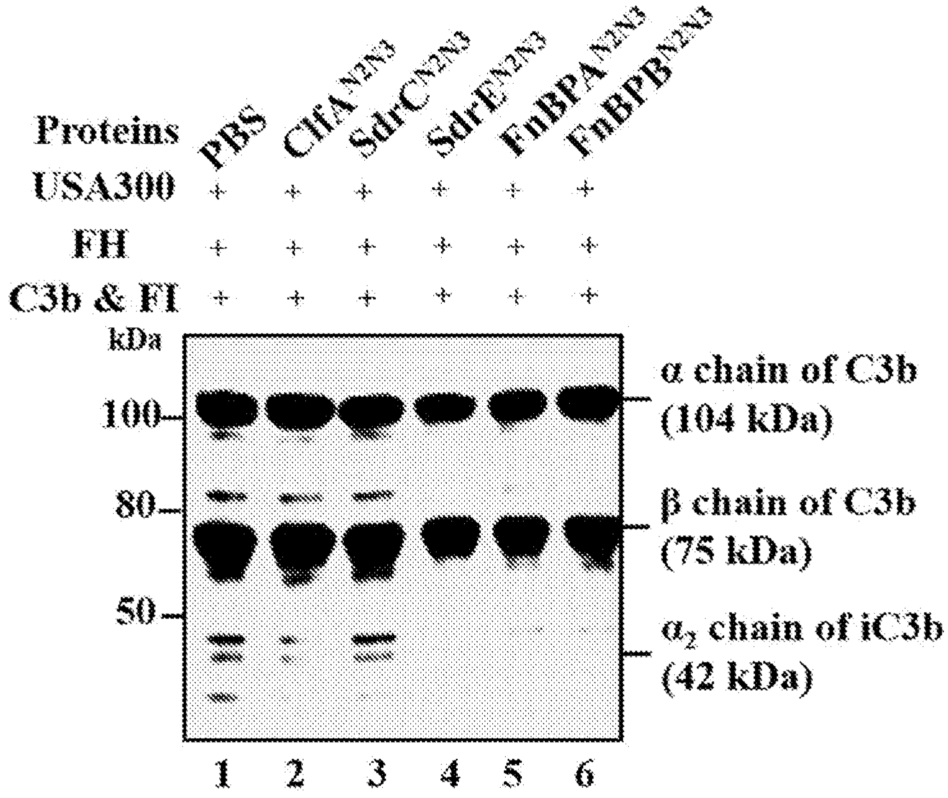

[FIG. 19a]
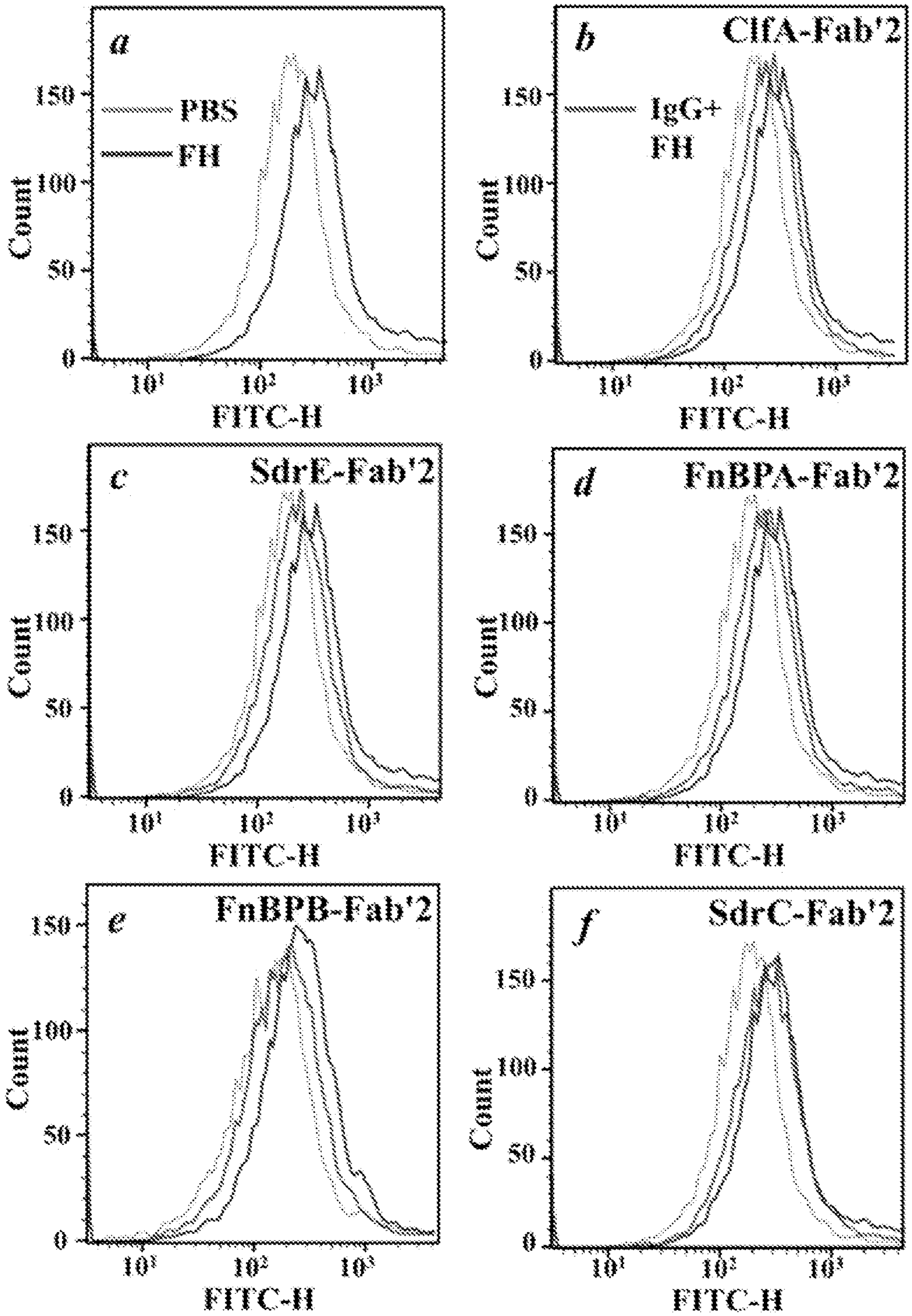

[FIG. 19b]
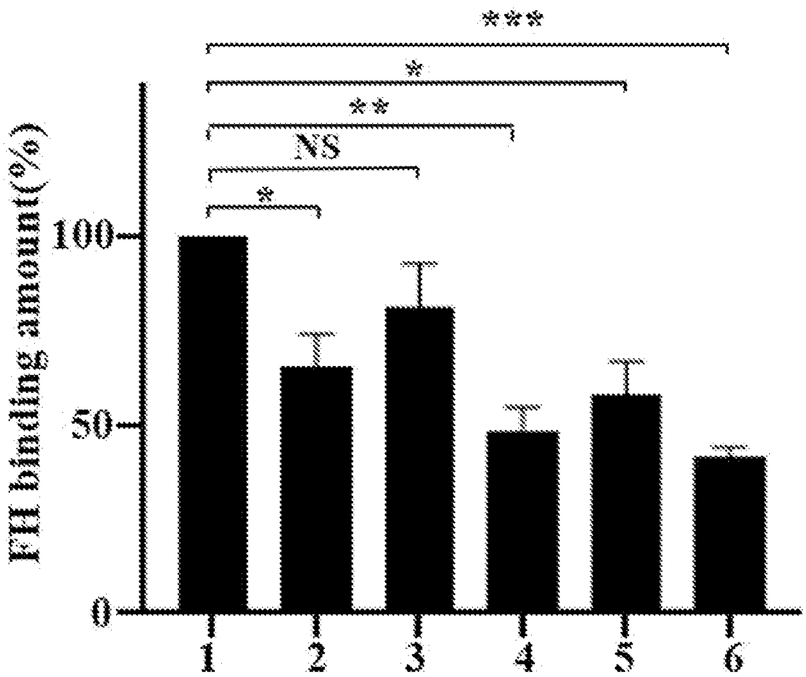

[FIG. 20a]
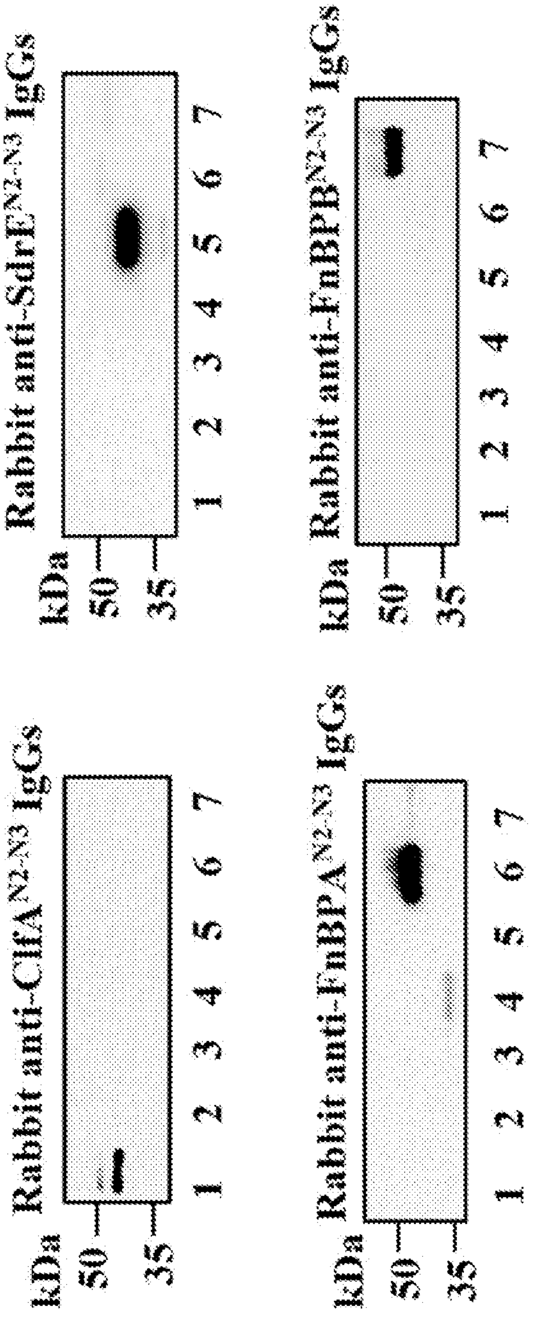

[FIG. 20b]
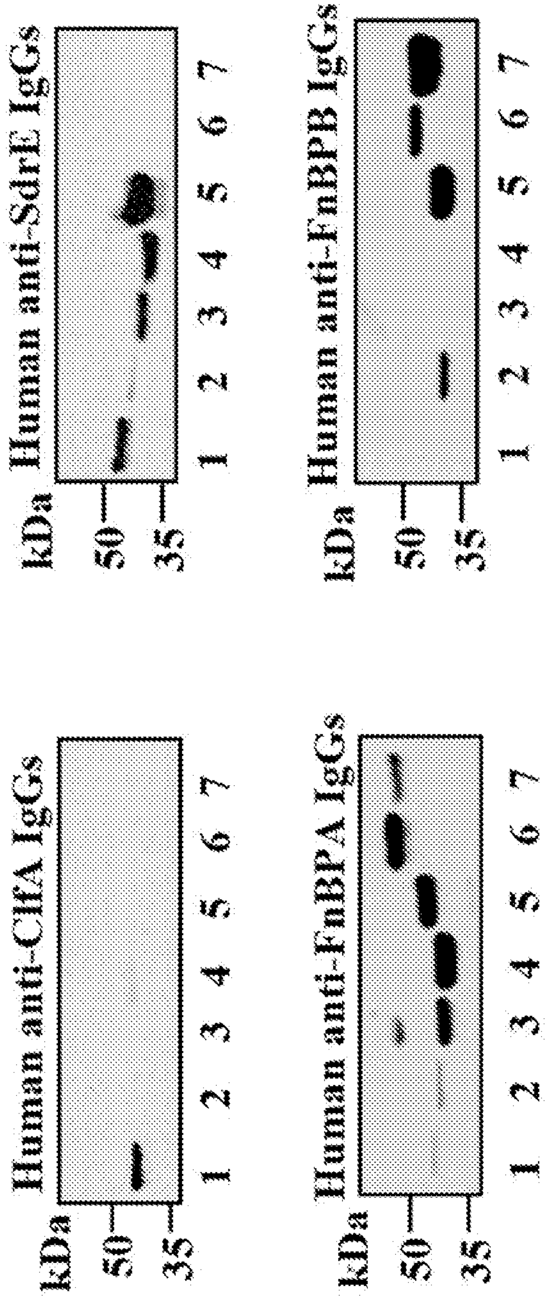

[FIG. 21a]
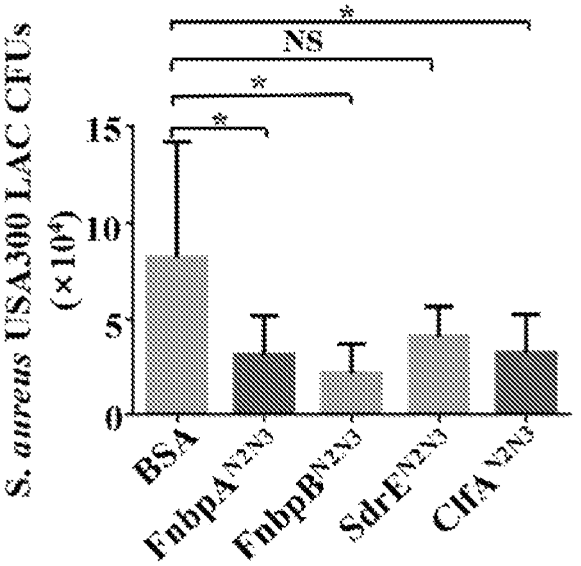
[FIG. 21b]
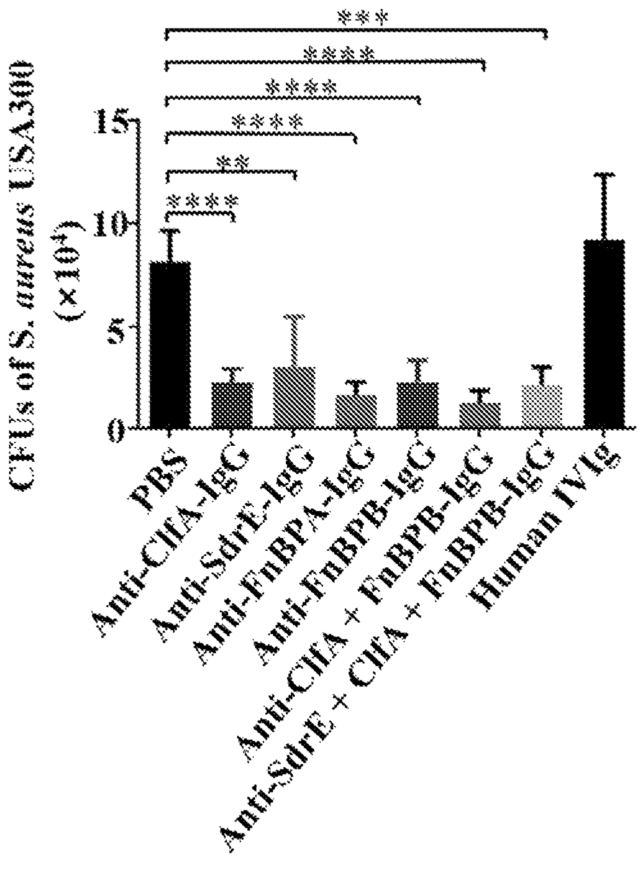

[FIG. 21c]
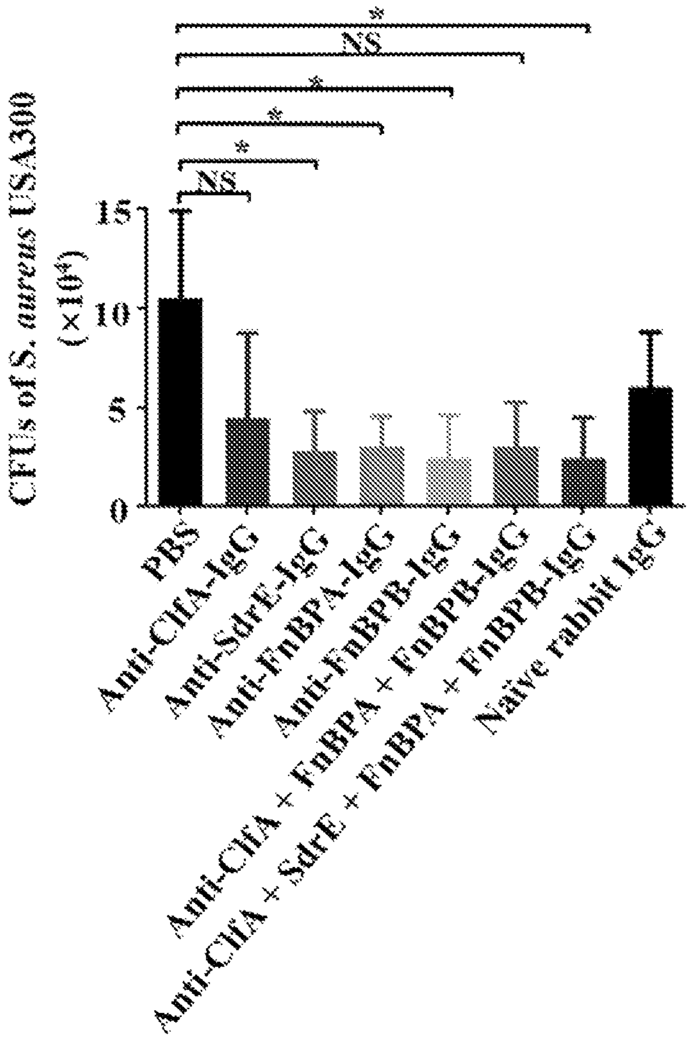

[FIG. 22]
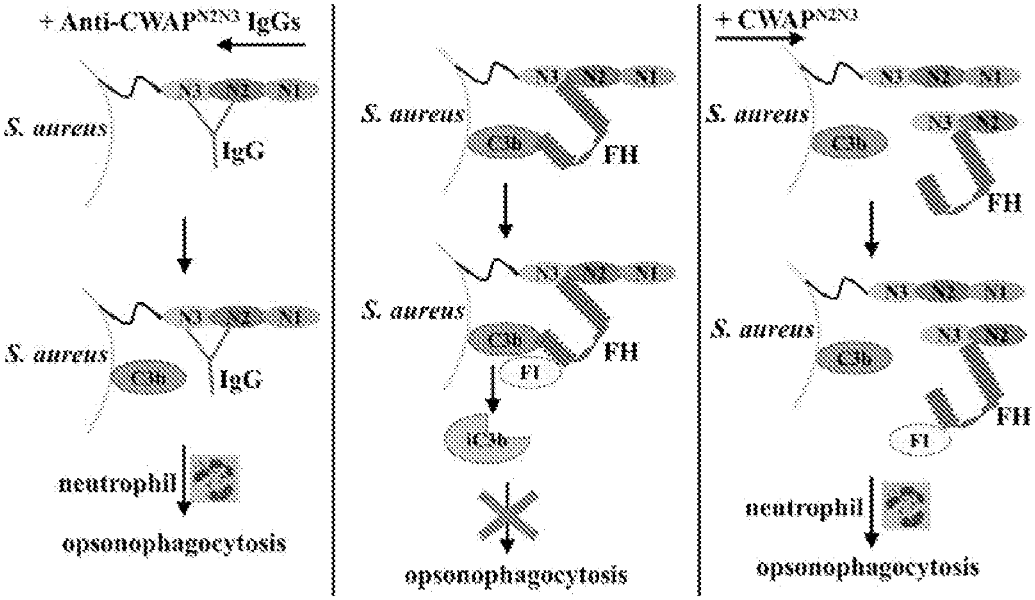
[FIG. 23]
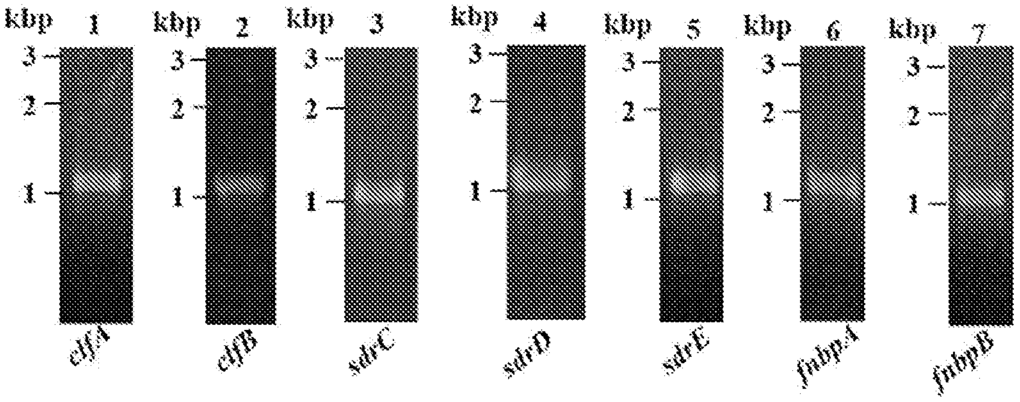
[FIG. 24a]
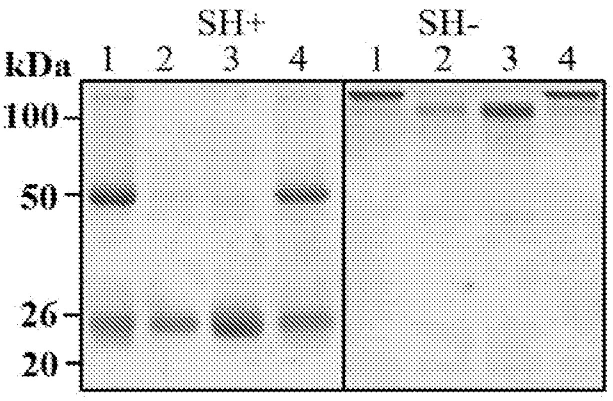

[FIG. 24b]
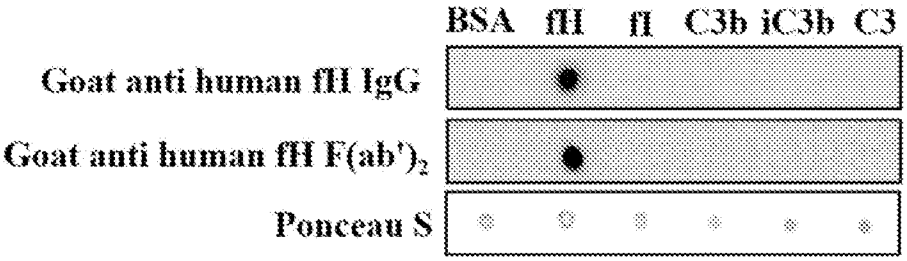
[FIG. 24c]
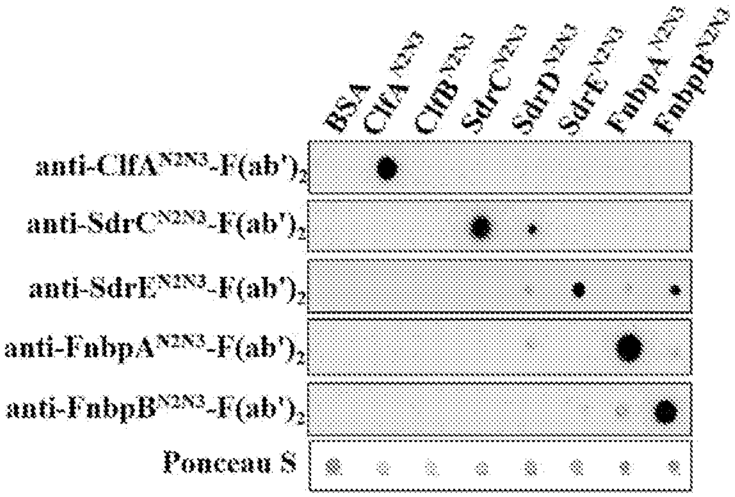
[FIG. 25a]
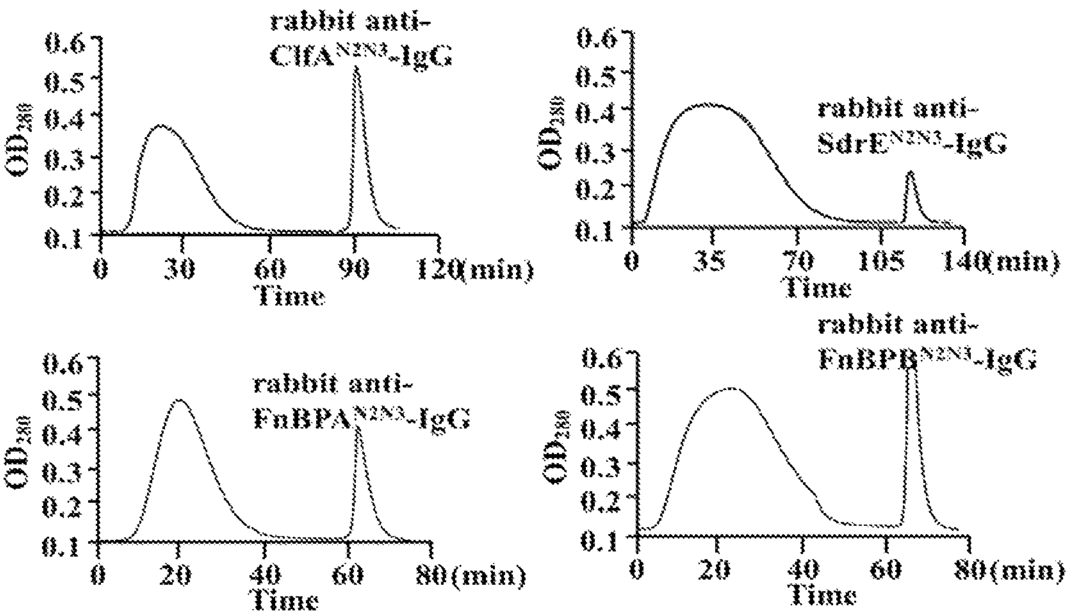

[FIG. 25b]
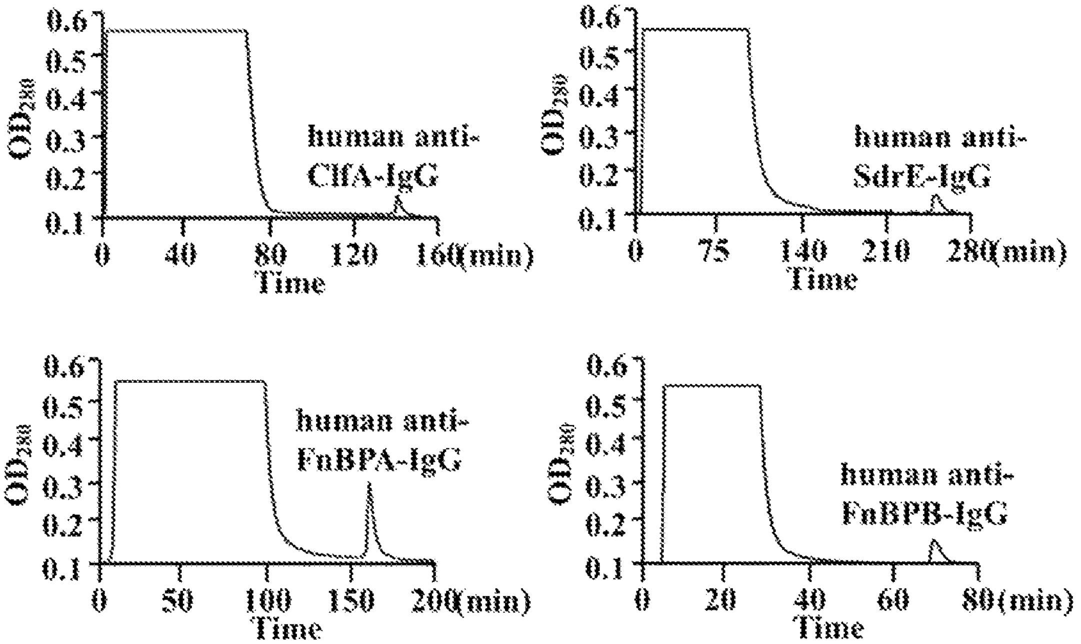
[FIG. 26]
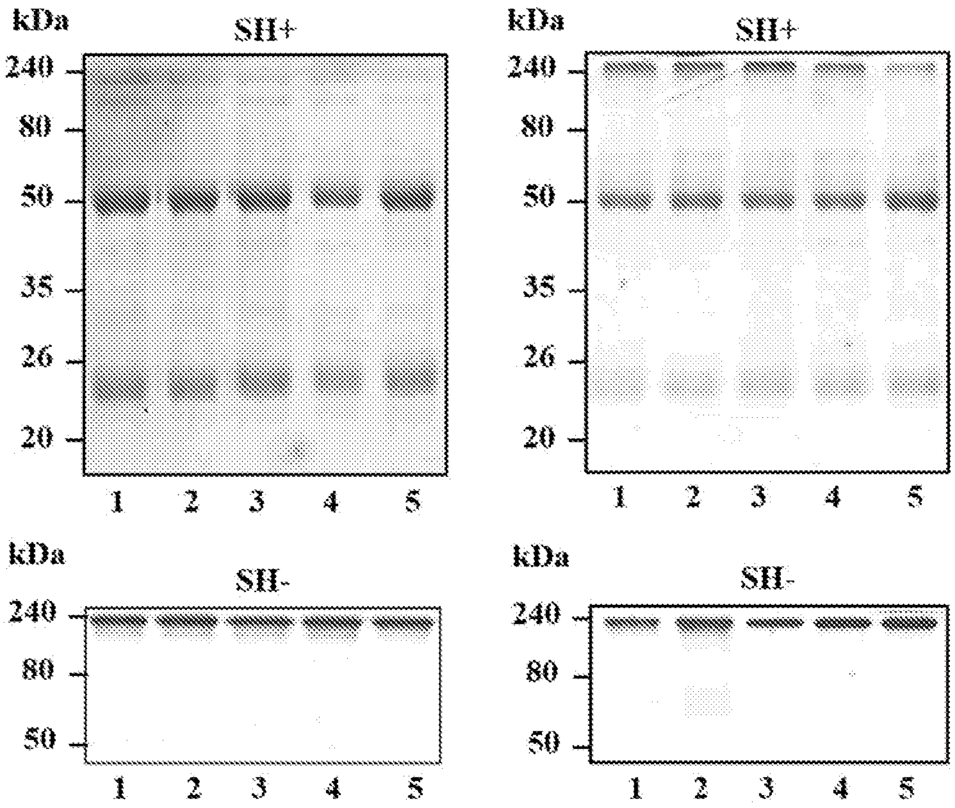

[FIG. 27a]
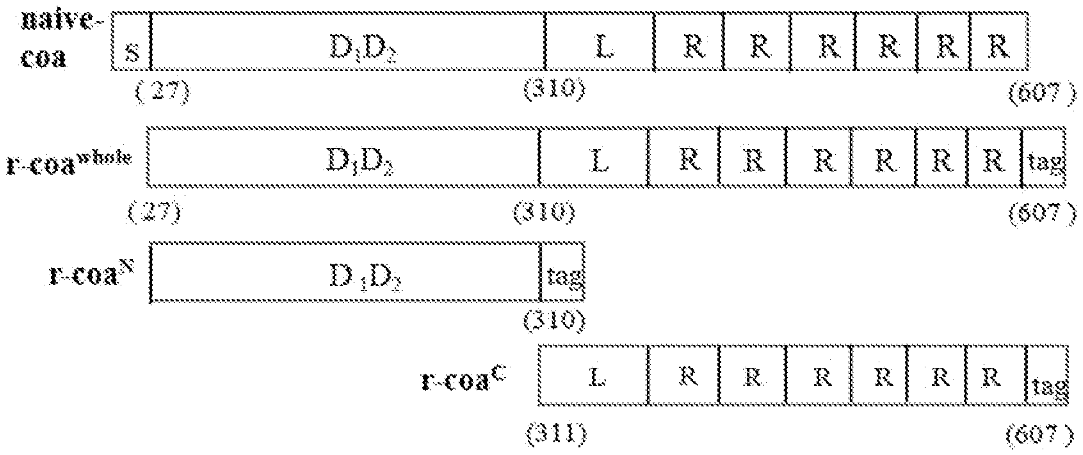
[FIG. 27b]
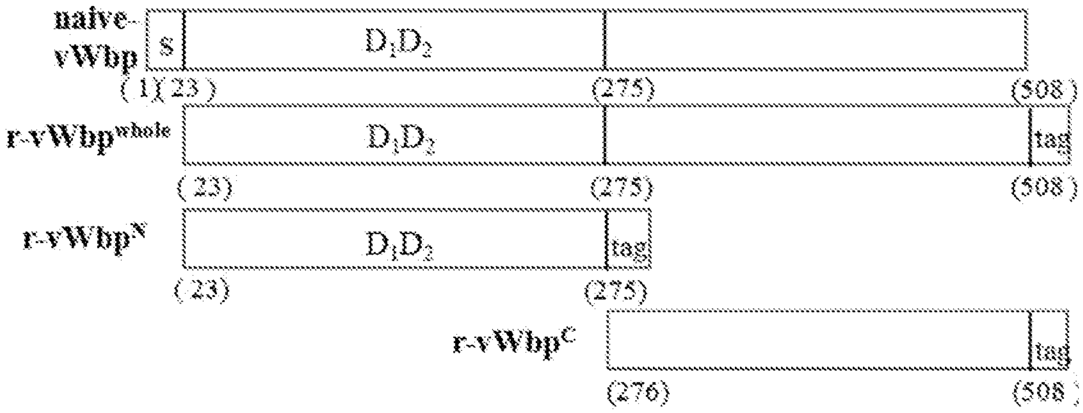
[FIG. 28]
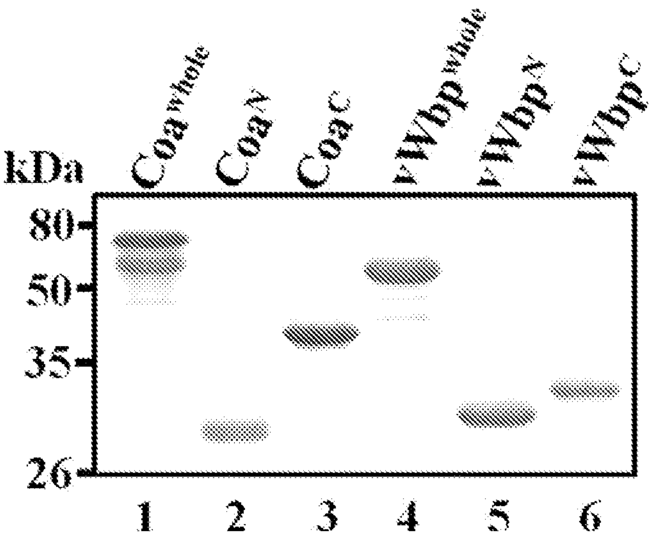

[FIG. 29a]
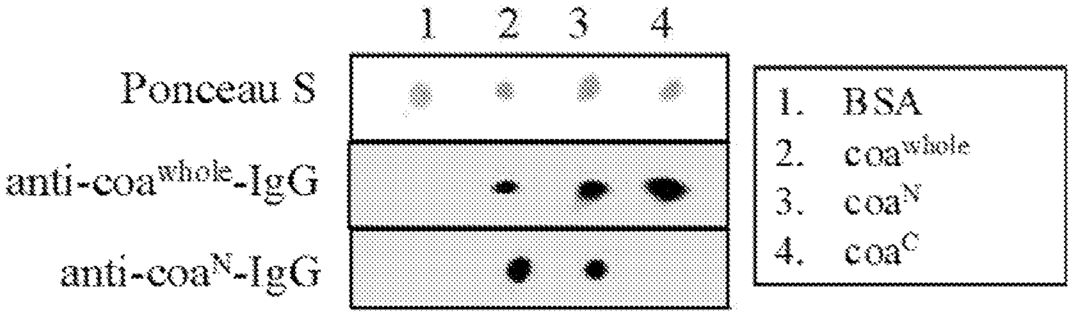
[FIG. 29b]
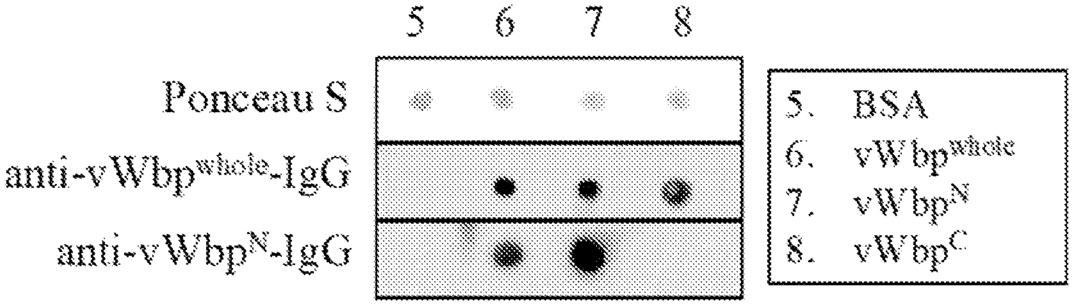
[FIG. 30a]
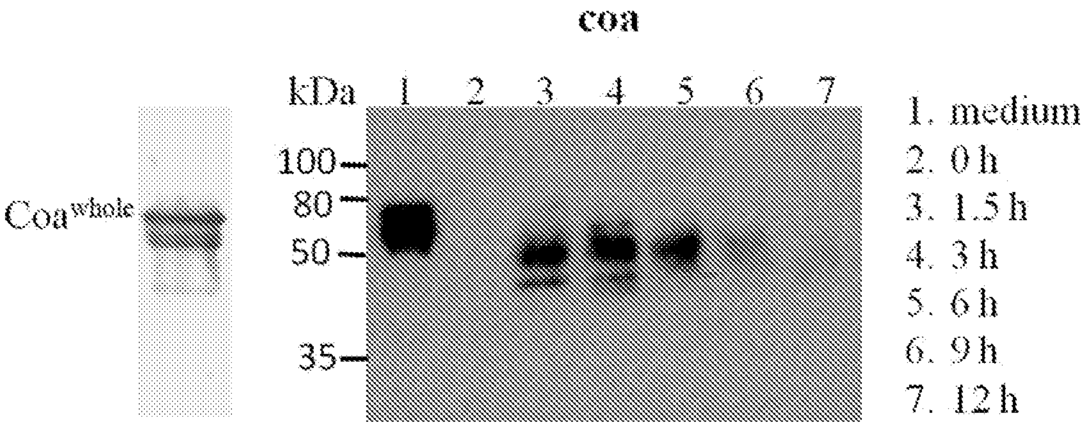

[FIG. 30b]
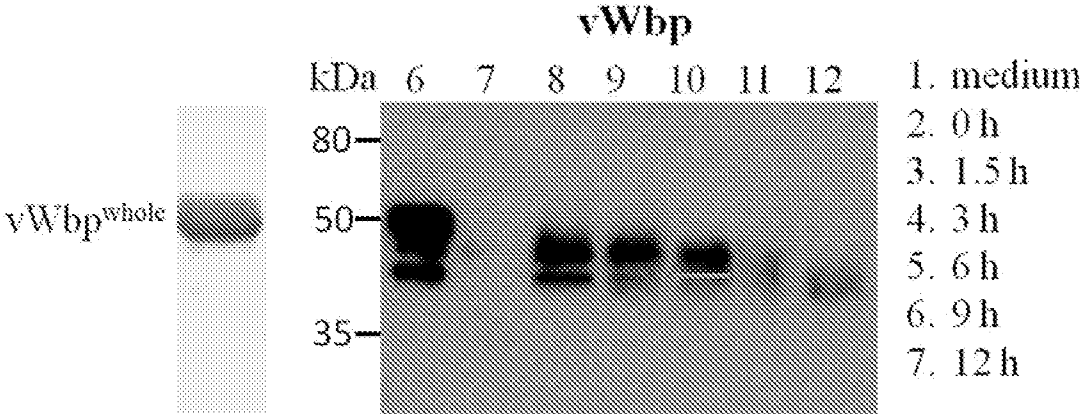
[FIG. 31a]
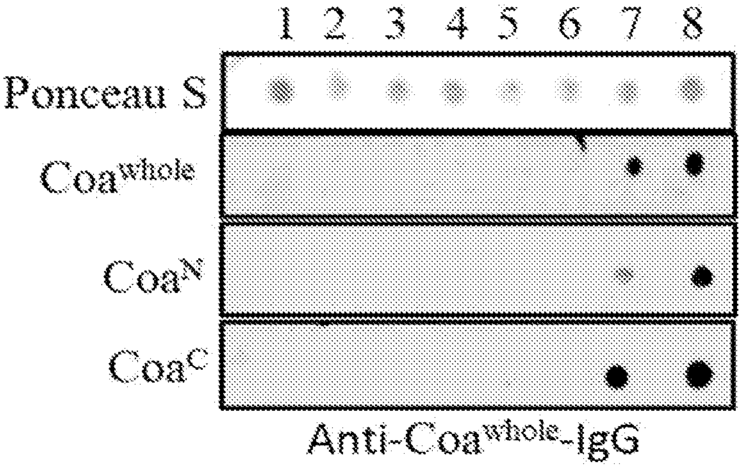
[FIG. 31b]
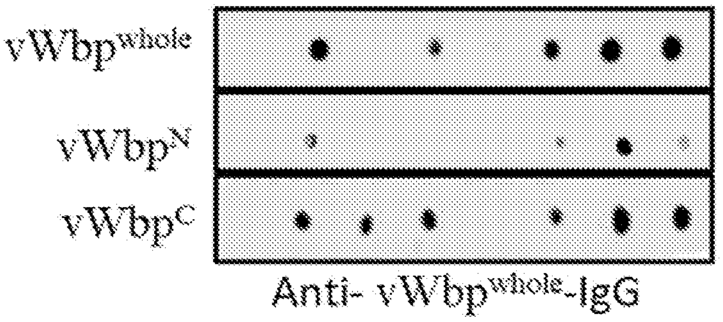

[FIG. 32]
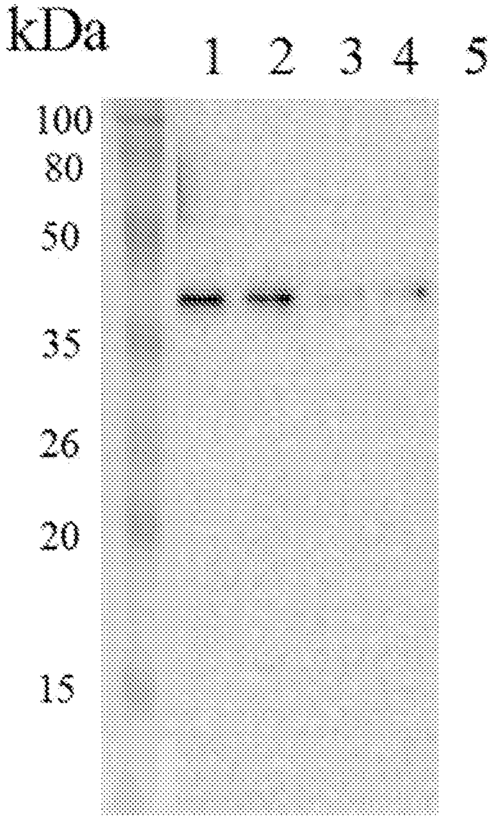
1. PBS+ $Coa^{C}$ —pellet
2. PBS+ anti-$SdrC^{N2N3}$-F(ab')2 +$Coa^{C}$ —pellet
3. PBS+ anti-$FnBPA^{N2N3}$-F(ab')2 +$Coa^{C}$ —pellet
4. PBS+ anti-$FnBPB^{N2N3}$-F(ab')2 +$Coa^{C}$ —pellet

[FIG. 33a]
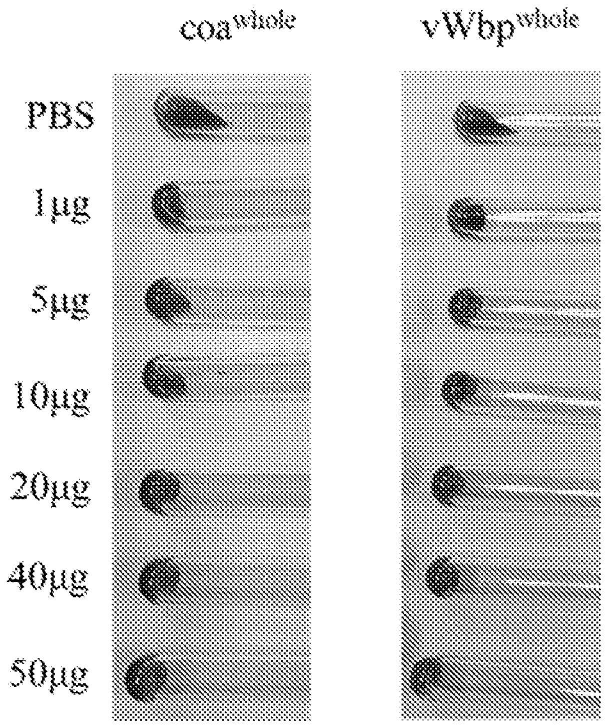
[FIG. 33b]
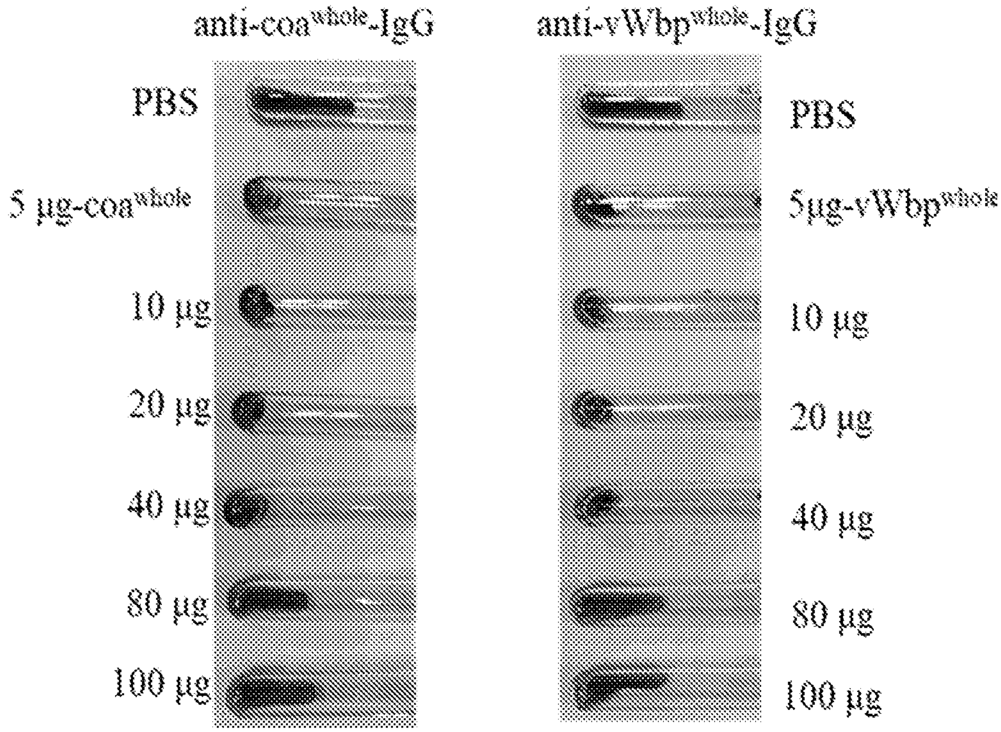

[FIG. 34]
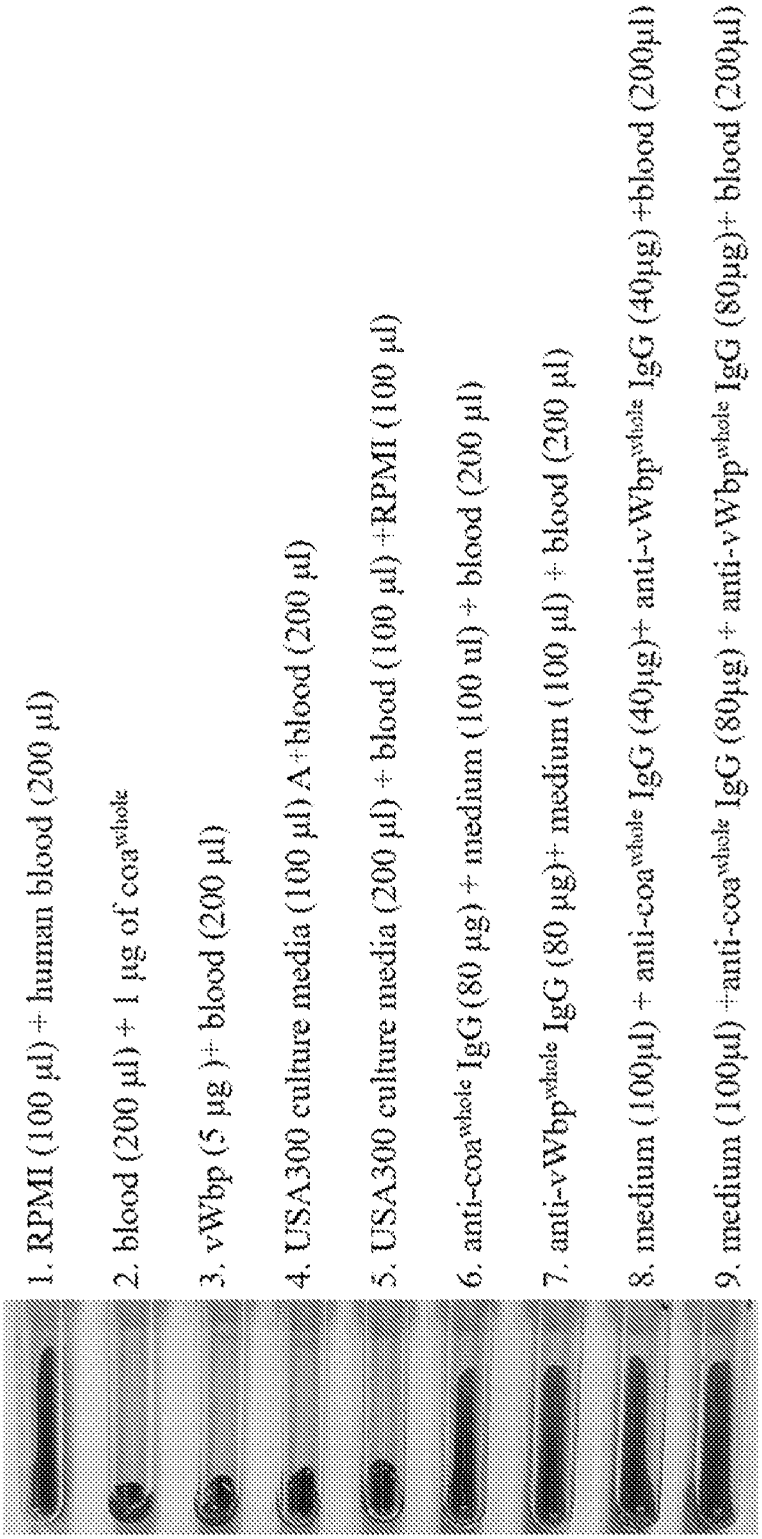

[FIG. 35]
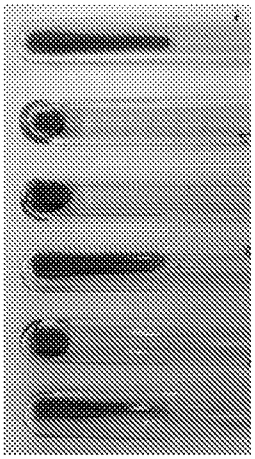
1. blood (200 μl) + RPMI medium (100 μl)
2. USA300 culture medium (100μl) + human blood (200μl)
3. blood (200 μl) + vWbp$^{N}$ (5 μg)
4. blood (200 μl) + vWbp$^{C}$ (5 μg)
5. blood (200 μl) +coa$^{N}$ (1 μg)
6. blood (200 μl) + coa$^{C}$ (1 μg)
[FIG. 36a]
Culture media
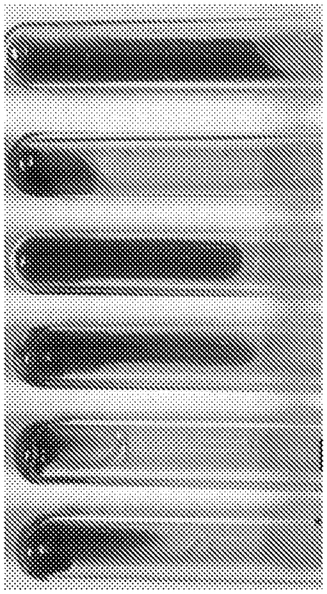
1 RPMI
2 medium
3 coa$^{N}$-Ab
4 vWbp$^{N}$-Ab
5 coa$^{C}$-Ab
6 vWbp$^{C}$-Ab

[FIG. 36b]
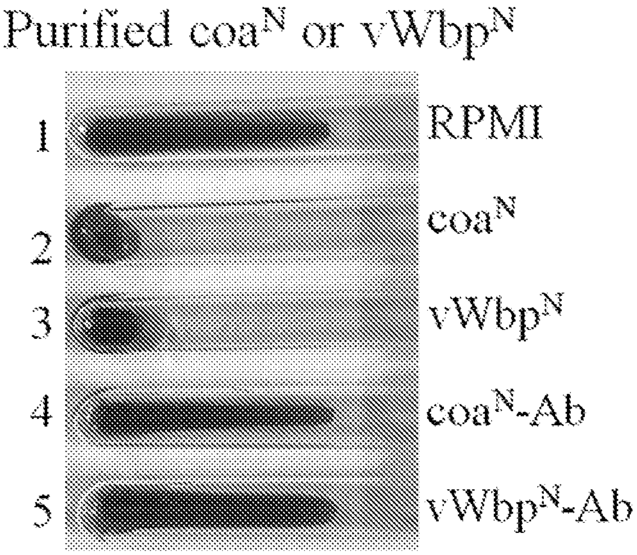
[FIG. 37]
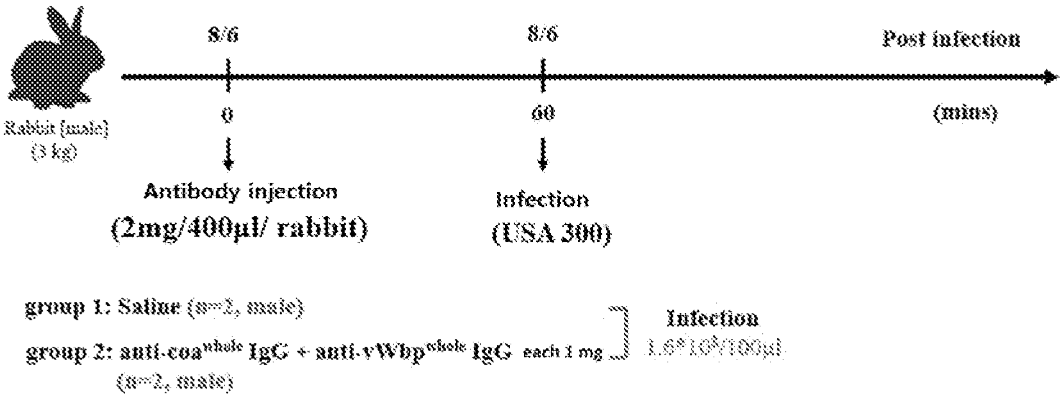

[FIG. 38]
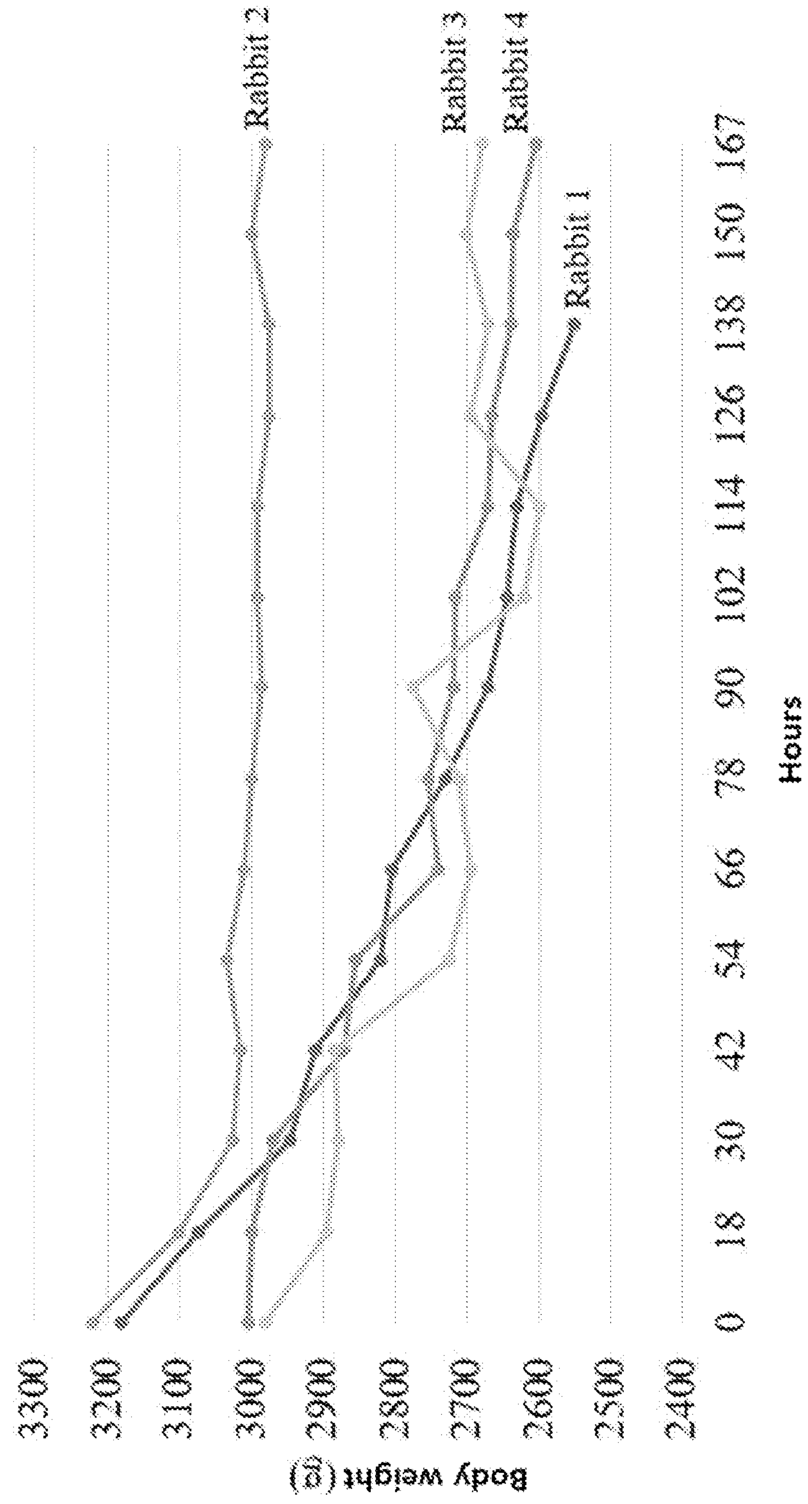

[FIG. 39a]
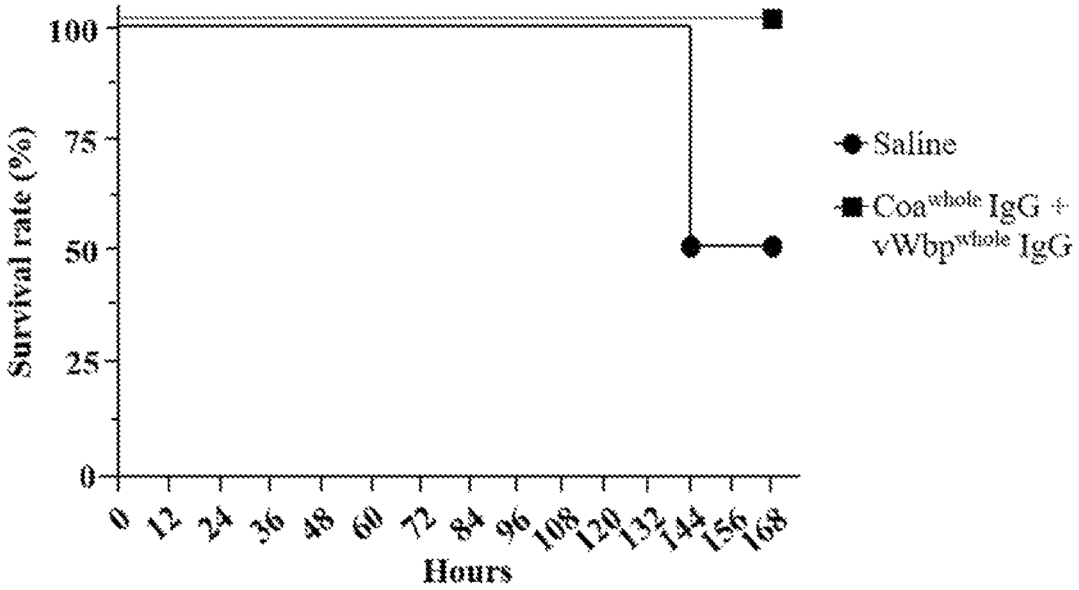
[FIG. 39b]
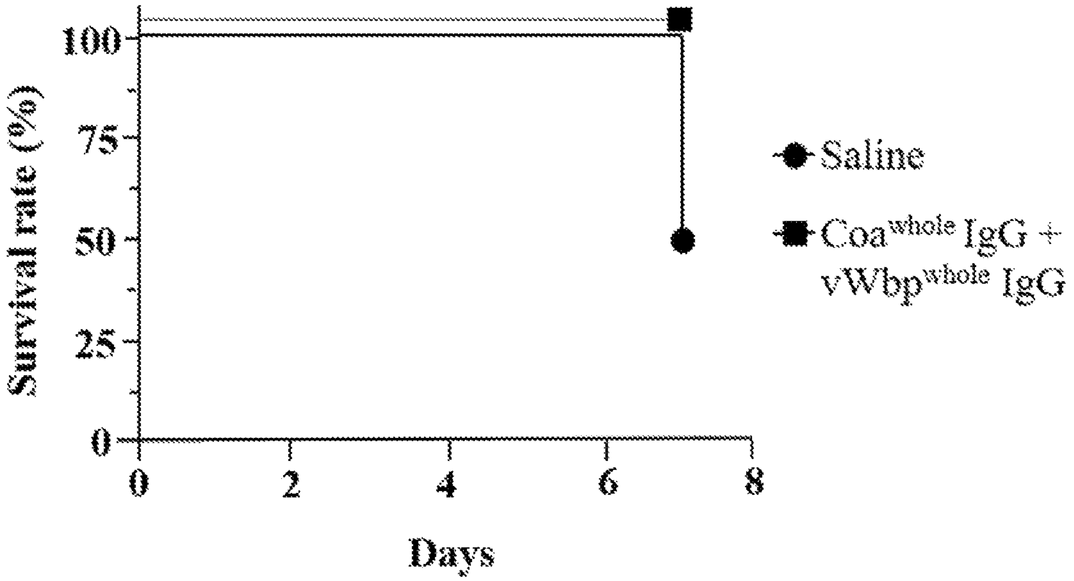

[FIG. 40a]
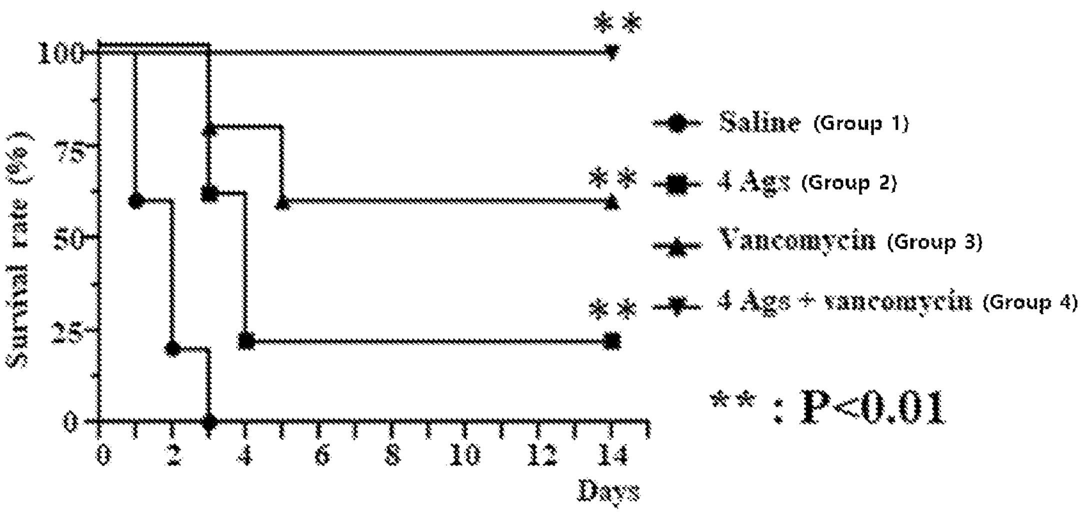
[FIG. 40b]
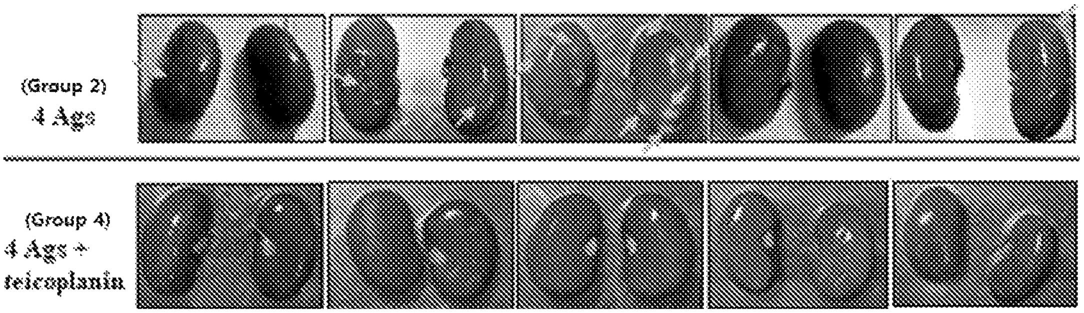

[FIG. 41a]
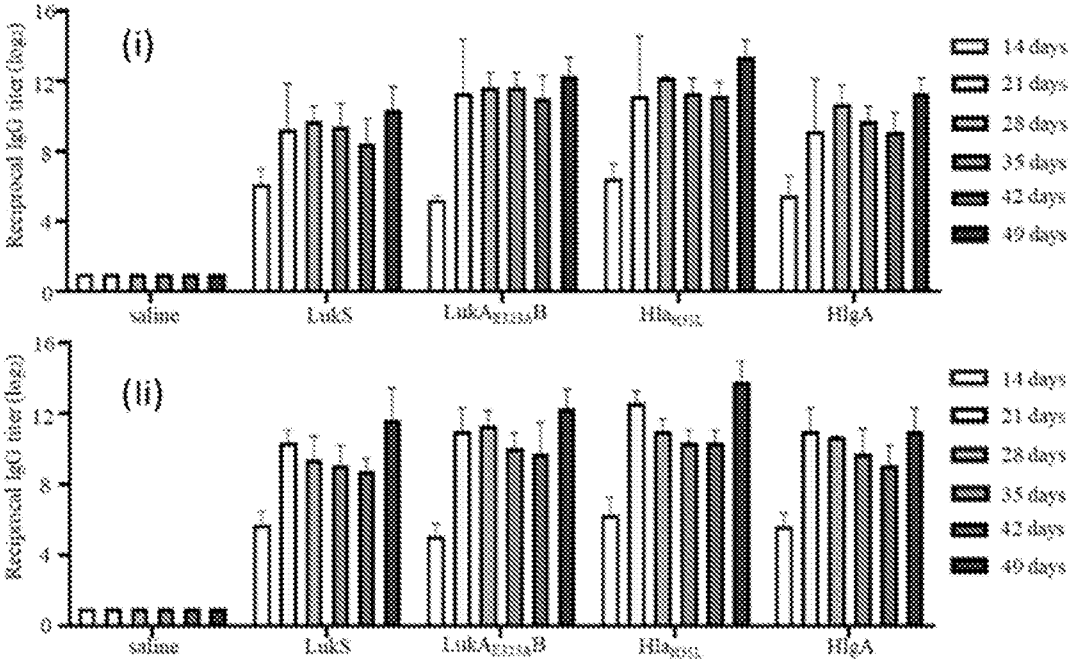
[FIG. 41b]
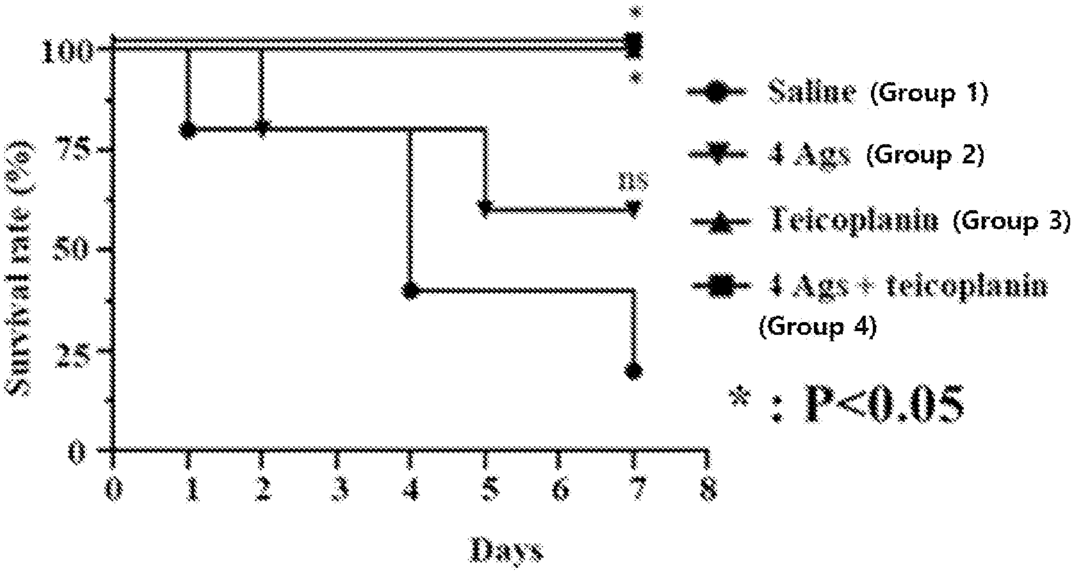

[FIG. 41c]
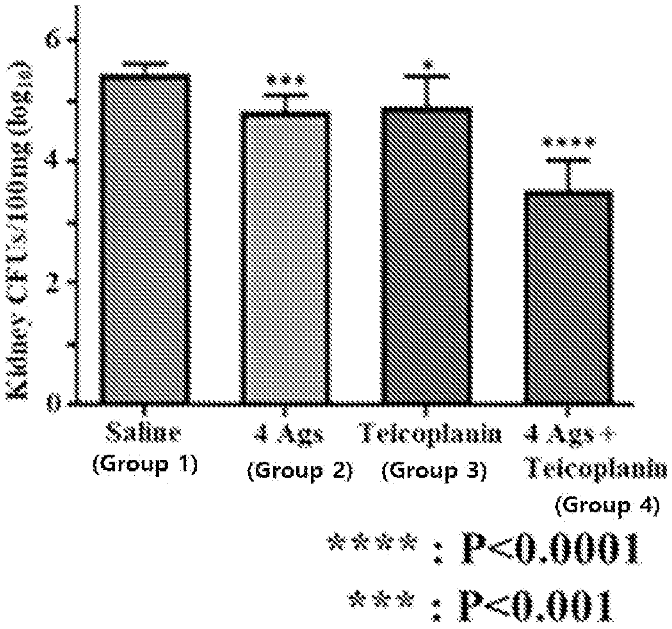
[FIG. 41d]
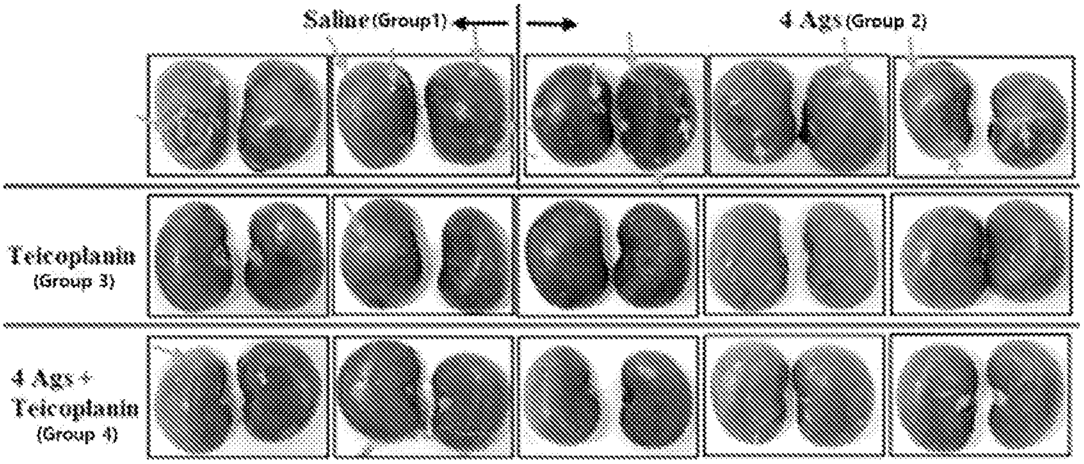

SEQUENCE LISTING

```
<160> NUMBER OF SEQ ID NOS: 54

<210> SEQ ID NO 1
<211> LENGTH: 29
<212> TYPE: DNA
<213> ORGANISM: Artificial Sequence
<220> FEATURE:
<223> OTHER INFORMATION: Vector-pET28a-F primer
```

-continued

<400> SEQUENCE: 1
catggtatat ctccttctta aagttaaac 29

<210> SEQ ID NO 2
<211> LENGTH: 25
<212> TYPE: DNA
<213> ORGANISM: Artificial Sequence
<220> FEATURE:
<223> OTHER INFORMATION: Vector-pET28a-R primer

<400> SEQUENCE: 2
caccaccacc accaccactg agatc 25

<210> SEQ ID NO 3
<211> LENGTH: 49
<212> TYPE: DNA
<213> ORGANISM: Artificial Sequence
<220> FEATURE:
<223> OTHER INFORMATION: pET28a-6 His-LukS-R primer

<400> SEQUENCE: 3
gtggtggtgg tggtgattat gtcctttcac tttaatttca tgagttttc 49

<210> SEQ ID NO 4
<211> LENGTH: 54
<212> TYPE: DNA
<213> ORGANISM: Artificial Sequence
<220> FEATURE:
<223> OTHER INFORMATION: pET28a-6 His-LukS-F primer

<400> SEQUENCE: 4
ctttaagaag gagatatacc atggataaca atattgagaa tattggtgat ggcg 54

<210> SEQ ID NO 5
<211> LENGTH: 29
<212> TYPE: DNA
<213> ORGANISM: Artificial Sequence
<220> FEATURE:
<223> OTHER INFORMATION: pET28a-6 His-LukST244A-R primer

<400> SEQUENCE: 5
catggtatat ctccttctta aagttaaac 29

<210> SEQ ID NO 6
<211> LENGTH: 37
<212> TYPE: DNA
<213> ORGANISM: Artificial Sequence
<220> FEATURE:
<223> OTHER INFORMATION: pET28a-6 His-LukST244A-F primer

<400> SEQUENCE: 6
ctattgccat agtgtgctgt tcttctagta gcatgag 37

<210> SEQ ID NO 7
<211> LENGTH: 44
<212> TYPE: DNA
<213> ORGANISM: Artificial Sequence
<220> FEATURE:
<223> OTHER INFORMATION: pET28a-6 His-LukF-R primer

<400> SEQUENCE: 7
gtggtggtgg tggtggctca taggattttt ttccttagat tgag 44

<210> SEQ ID NO 8

-continued

<211> LENGTH: 50
<212> TYPE: DNA
<213> ORGANISM: Artificial Sequence
<220> FEATURE:
<223> OTHER INFORMATION: pET28a-6 His-LukF-F primer

<400> SEQUENCE: 8
ctttaagaag gagatatacc atggctcaac atatcacacc tgtaagtgag 50

<210> SEQ ID NO 9
<211> LENGTH: 45
<212> TYPE: DNA
<213> ORGANISM: Artificial Sequence
<220> FEATURE:
<223> OTHER INFORMATION: pET28a-6 His-HlgA-R primer

<400> SEQUENCE: 9
gtggtggtgg tggtgcttag gtgtgatgct tttaattttt acttc 45

<210> SEQ ID NO 10
<211> LENGTH: 55
<212> TYPE: DNA
<213> ORGANISM: Artificial Sequence
<220> FEATURE:
<223> OTHER INFORMATION: pET28a-6 His-HlgA-F primer

<400> SEQUENCE: 10
ctttaagaag gagatatacc atggaaaata agatagaaga tatcggccaa ggtgc 55

<210> SEQ ID NO 11
<211> LENGTH: 42
<212> TYPE: DNA
<213> ORGANISM: Artificial Sequence
<220> FEATURE:
<223> OTHER INFORMATION: pET28a-6 His-HlgC-R primer

<400> SEQUENCE: 11
gtggtggtgg tggtgattct gtcctttcac cttgatttca tg 42

<210> SEQ ID NO 12
<211> LENGTH: 51
<212> TYPE: DNA
<213> ORGANISM: Artificial Sequence
<220> FEATURE:
<223> OTHER INFORMATION: pET28a-6 His-HlgC-F primer

<400> SEQUENCE: 12
ctttaagaag gagatatacc atgctaacga tactgaagac atcggtaaag g 51

<210> SEQ ID NO 13
<211> LENGTH: 48
<212> TYPE: DNA
<213> ORGANISM: Artificial Sequence
<220> FEATURE:
<223> OTHER INFORMATION: pET28a-6 His-LukE-R primer

<400> SEQUENCE: 13
gtggtggtgg tggtgttatg tcctttcact ttaatttcgt gtgttttc 48

<210> SEQ ID NO 14
<211> LENGTH: 57
<212> TYPE: DNA
<213> ORGANISM: Artificial Sequence
<220> FEATURE:
<223> OTHER INFORMATION: pET28a-6 His-LukE-F primer

<400> SEQUENCE: 14
ctttaagaag gagatatacc atgaatacta atattgaaaa tattggtgat ggtgctg 57

<210> SEQ ID NO 15
<211> LENGTH: 44
<212> TYPE: DNA
<213> ORGANISM: Artificial Sequence
<220> FEATURE:
<223> OTHER INFORMATION: pET28a-6 His-LukD-R primer

<400> SEQUENCE: 15
gtggtggtgg tggtgtactc caggattagt ttctttagaa tccg 44

<210> SEQ ID NO 16
<211> LENGTH: 48
<212> TYPE: DNA
<213> ORGANISM: Artificial Sequence
<220> FEATURE:
<223> OTHER INFORMATION: pET28a-6 His-LukD-F primer

<400> SEQUENCE: 16
ctttaagaag gagatatacc atggctcaac atatcacacc tgtaagcg 48

<210> SEQ ID NO 17
<211> LENGTH: 46
<212> TYPE: DNA
<213> ORGANISM: Artificial Sequence
<220> FEATURE:
<223> OTHER INFORMATION: pET28a-6 His-Hla-R primer

<400> SEQUENCE: 17
cagtggtggt ggtggtggtg atttgtcatt tcttcttttt cccaat 46

<210> SEQ ID NO 18
<211> LENGTH: 48
<212> TYPE: DNA
<213> ORGANISM: Artificial Sequence
<220> FEATURE:
<223> OTHER INFORMATION: pET28a-6 His-Hla-F primer

<400> SEQUENCE: 18
aagaaggaga tataccatgg cagattctga tattaatatt aaaaccgg 48

<210> SEQ ID NO 19
<211> LENGTH: 37
<212> TYPE: DNA
<213> ORGANISM: Artificial Sequence
<220> FEATURE:
<223> OTHER INFORMATION: pET28a-6 His-HlaH35L-R primer

<400> SEQUENCE: 19
gaagaacgat ctatccattt atctttagta ttggtac 37

<210> SEQ ID NO 20
<211> LENGTH: 46
<212> TYPE: DNA
<213> ORGANISM: Artificial Sequence
<220> FEATURE:
<223> OTHER INFORMATION: pET28a-6 His-HlaH35L-F primer

<400> SEQUENCE: 20
gataaagaaa atggcatgct caaaaaagta ttttatagtt ttatcg 46

<210> SEQ ID NO 21
<211> LENGTH: 22
<212> TYPE: DNA

```
<213> ORGANISM: Artificial Sequence
<220> FEATURE:
<223> OTHER INFORMATION: Vector-pET28a-R primer

<400> SEQUENCE: 21

gtgatgatga tgatgatggc tg                                              22


<210> SEQ ID NO 22
<211> LENGTH: 25
<212> TYPE: DNA
<213> ORGANISM: Artificial Sequence
<220> FEATURE:
<223> OTHER INFORMATION: Vector-pET28a-F primer

<400> SEQUENCE: 22

caccaccacc accaccactg agatc                                           25


<210> SEQ ID NO 23
<211> LENGTH: 54
<212> TYPE: DNA
<213> ORGANISM: Artificial Sequence
<220> FEATURE:
<223> OTHER INFORMATION: pET28a-6 His-hlgB-R primer

<400> SEQUENCE: 23

ttgttagcag ccggatctca tttattgttt tcagtttctt ttgtatctaa caat           54


<210> SEQ ID NO 24
<211> LENGTH: 47
<212> TYPE: DNA
<213> ORGANISM: Artificial Sequence
<220> FEATURE:
<223> OTHER INFORMATION: pET28a-6 His-hlgB-F primer

<400> SEQUENCE: 24

atgggcagca gccatcatca tcatcatcac gaaggtaaaa taacacc                   47


<210> SEQ ID NO 25
<211> LENGTH: 57
<212> TYPE: DNA
<213> ORGANISM: Artificial Sequence
<220> FEATURE:
<223> OTHER INFORMATION: pET28a-6 His-LukA-R primer

<400> SEQUENCE: 25

atgggcagca gccatcatca tcatcatcac aattcagctc ataaagactc tcaagac        57


<210> SEQ ID NO 26
<211> LENGTH: 53
<212> TYPE: DNA
<213> ORGANISM: Artificial Sequence
<220> FEATURE:
<223> OTHER INFORMATION: pET28a-6 His-LukA-F primer

<400> SEQUENCE: 26

tagtaatccg ccctttcaat attatccttc tttataaggt ttattgtcat cag            53


<210> SEQ ID NO 27
<211> LENGTH: 56
<212> TYPE: DNA
<213> ORGANISM: Artificial Sequence
<220> FEATURE:
<223> OTHER INFORMATION: pET28a-6 His-LukB-R primer

<400> SEQUENCE: 27

cagtggtggt ggtggtggtg ttatttcttt tcattatcat taagtacttt tacaaa         56
```

<210> SEQ ID NO 28
<211> LENGTH: 53
<212> TYPE: DNA
<213> ORGANISM: Artificial Sequence
<220> FEATURE:
<223> OTHER INFORMATION: pET28a-6 His-LukB-F primer

<400> SEQUENCE: 28
tattgaaagg gcggattact aatgaagatt aattctgaaa tcaaacaagt ttc 53

<210> SEQ ID NO 29
<211> LENGTH: 53
<212> TYPE: DNA
<213> ORGANISM: Artificial Sequence
<220> FEATURE:
<223> OTHER INFORMATION: pET28a-6 His-LukAE323A-F primer

<400> SEQUENCE: 29
tagtaatccg ccctttcaat attatcctgc tttataaggt ttattgtcat cag 53

<210> SEQ ID NO 30
<211> LENGTH: 57
<212> TYPE: DNA
<213> ORGANISM: Artificial Sequence
<220> FEATURE:
<223> OTHER INFORMATION: pET28a-6 His-LukAE323A-R primer

<400> SEQUENCE: 30
atgggcagca gccatcatca tcatcatcac aattcagctc ataaagactc tcaagac 57

<210> SEQ ID NO 31
<211> LENGTH: 47
<212> TYPE: DNA
<213> ORGANISM: Artificial Sequence
<220> FEATURE:
<223> OTHER INFORMATION: clfA-F primer

<400> SEQUENCE: 31
ttgttagcag ccggatctca tgaattagaa tcgctgccag aatctga 47

<210> SEQ ID NO 32
<211> LENGTH: 55
<212> TYPE: DNA
<213> ORGANISM: Artificial Sequence
<220> FEATURE:
<223> OTHER INFORMATION: clfA-R primer

<400> SEQUENCE: 32
atgggcagca gccatcatca tcatcatcac gcatttagtt tagcggcagt agctg 55

<210> SEQ ID NO 33
<211> LENGTH: 39
<212> TYPE: DNA
<213> ORGANISM: Artificial Sequence
<220> FEATURE:
<223> OTHER INFORMATION: clfB-F primer

<400> SEQUENCE: 33
ttgttagcag ccggatctca ttctgggtca accggcggc 39

<210> SEQ ID NO 34
<211> LENGTH: 53
<212> TYPE: DNA
<213> ORGANISM: Artificial Sequence
<220> FEATURE:

<223> OTHER INFORMATION: clfB-R primer

<400> SEQUENCE: 34
atgggcagca gccatcatca tcatcatcac gttgctgaac cggtagtaaa tgc 53

<210> SEQ ID NO 35
<211> LENGTH: 51
<212> TYPE: DNA
<213> ORGANISM: Artificial Sequence
<220> FEATURE:
<223> OTHER INFORMATION: sdrC-F primer

<400> SEQUENCE: 35
ctttaagaag gagatatacc atgagaactt taaatcgcat ggcagtgaat a 51

<210> SEQ ID NO 36
<211> LENGTH: 47
<212> TYPE: DNA
<213> ORGANISM: Artificial Sequence
<220> FEATURE:
<223> OTHER INFORMATION: sdrC-R primer

<400> SEQUENCE: 36
cagtggtggt ggtggtggtg tgtatcttcc catacatagt cacctag 47

<210> SEQ ID NO 37
<211> LENGTH: 51
<212> TYPE: DNA
<213> ORGANISM: Artificial Sequence
<220> FEATURE:
<223> OTHER INFORMATION: sdrD-F primer

<400> SEQUENCE: 37
ctttaagaag gagatatacc atggcaccta aacgtttgaa tacaagaatg c 51

<210> SEQ ID NO 38
<211> LENGTH: 43
<212> TYPE: DNA
<213> ORGANISM: Artificial Sequence
<220> FEATURE:
<223> OTHER INFORMATION: sdrD-R primer

<400> SEQUENCE: 38
cagtggtggt ggtggtggtg atatacttct tgaccagctc cgc 43

<210> SEQ ID NO 39
<211> LENGTH: 54
<212> TYPE: DNA
<213> ORGANISM: Artificial Sequence
<220> FEATURE:
<223> OTHER INFORMATION: sdrE-F primer

<400> SEQUENCE: 39
ttgttagcag ccggatctca aattttgtat aacttttctt caggtttaac agta 54

<210> SEQ ID NO 40
<211> LENGTH: 55
<212> TYPE: DNA
<213> ORGANISM: Artificial Sequence
<220> FEATURE:
<223> OTHER INFORMATION: sdrE-R primer

<400> SEQUENCE: 40
atgggcagca gccatcatca tcatcatcac gtaaacgcaa aaatgcgctt tgcag 55

-continued

<210> SEQ ID NO 41
<211> LENGTH: 49
<212> TYPE: DNA
<213> ORGANISM: Artificial Sequence
<220> FEATURE:
<223> OTHER INFORMATION: fnbpA-F primer

<400> SEQUENCE: 41
ctttaagaag gagatatacc atggtagcgg aagctaagga agctagtaa 49

<210> SEQ ID NO 42
<211> LENGTH: 46
<212> TYPE: DNA
<213> ORGANISM: Artificial Sequence
<220> FEATURE:
<223> OTHER INFORMATION: fnbpA-R primer

<400> SEQUENCE: 42
cagtggtggt ggtggtggtg agctgtgtgg taatcaatgt caagag 46

<210> SEQ ID NO 43
<211> LENGTH: 46
<212> TYPE: DNA
<213> ORGANISM: Artificial Sequence
<220> FEATURE:
<223> OTHER INFORMATION: fnbpB-F primer

<400> SEQUENCE: 43
taagaaggag atataccatg atgaaaagat caactgacgt tacagc 46

<210> SEQ ID NO 44
<211> LENGTH: 41
<212> TYPE: DNA
<213> ORGANISM: Artificial Sequence
<220> FEATURE:
<223> OTHER INFORMATION: fnbpB-R primer

<400> SEQUENCE: 44
cagtggtggt ggtggtggtg cactggcggc tctgatttaa a 41

<210> SEQ ID NO 45
<211> LENGTH: 26
<212> TYPE: DNA
<213> ORGANISM: Artificial Sequence
<220> FEATURE:
<223> OTHER INFORMATION: pET28a-C-fragment1-F primer

<400> SEQUENCE: 45
gcatcctctc tcgtttcatc ggtatc 26

<210> SEQ ID NO 46
<211> LENGTH: 25
<212> TYPE: DNA
<213> ORGANISM: Artificial Sequence
<220> FEATURE:
<223> OTHER INFORMATION: pET28a-C-fragment1-R primer

<400> SEQUENCE: 46
caccaccacc accaccactg agatc 25

<210> SEQ ID NO 47
<211> LENGTH: 29
<212> TYPE: DNA
<213> ORGANISM: Artificial Sequence
<220> FEATURE:
<223> OTHER INFORMATION: pET28a-C-fragment2-F primer

<400> SEQUENCE: 47
catggtatat ctccttctta aagttaaac 29

<210> SEQ ID NO 48
<211> LENGTH: 26
<212> TYPE: DNA
<213> ORGANISM: Artificial Sequence
<220> FEATURE:
<223> OTHER INFORMATION: pET28a-C-fragment2-R primer

<400> SEQUENCE: 48
gaaacgagag aggatgctca cgatac 26

<210> SEQ ID NO 49
<211> LENGTH: 26
<212> TYPE: DNA
<213> ORGANISM: Artificial Sequence
<220> FEATURE:
<223> OTHER INFORMATION: pET28a-N-fragment1-F primer

<400> SEQUENCE: 49
gcatcctctc tcgtttcatc ggtatc 26

<210> SEQ ID NO 50
<211> LENGTH: 23
<212> TYPE: DNA
<213> ORGANISM: Artificial Sequence
<220> FEATURE:
<223> OTHER INFORMATION: pET28a-N-fragment1-R primer

<400> SEQUENCE: 50
tgagatccgg ctgctaacaa agc 23

<210> SEQ ID NO 51
<211> LENGTH: 23
<212> TYPE: DNA
<213> ORGANISM: Artificial Sequence
<220> FEATURE:
<223> OTHER INFORMATION: pET28a-N-fragment2-F primer

<400> SEQUENCE: 51
gtgatgatga tgatgatggc tgc 23

<210> SEQ ID NO 52
<211> LENGTH: 26
<212> TYPE: DNA
<213> ORGANISM: Artificial Sequence
<220> FEATURE:
<223> OTHER INFORMATION: pET28a-N-fragment2-R primer

<400> SEQUENCE: 52
gaaacgagag aggatgctca cgatac 26

<210> SEQ ID NO 53
<211> LENGTH: 23
<212> TYPE: DNA
<213> ORGANISM: Artificial Sequence
<220> FEATURE:
<223> OTHER INFORMATION: T7 promoter

<400> SEQUENCE: 53
aaattaatac gactcactat agg 23

<210> SEQ ID NO 54
<211> LENGTH: 21

-continued

```
<212> TYPE: DNA
<213> ORGANISM: Artificial Sequence
<220> FEATURE:
<223> OTHER INFORMATION: T7 terminator

<400> SEQUENCE: 54

atgctagtta ttgctcagcg g                                                21
```

COMPOSITION FOR PREVENTION OR TREATMENT OF *STAPHYLOCOCCUS AUREUS* INFECTIOUS DISEASE

CROSS REFERENCE TO RELATED APPLICATIONS

This application is a National Stage of International Application No. PCT/KR2021/012222, filed Sep. 8, 2021, claiming priority to Korean Patent Application No. 10-2020-0114435, filed Sep. 8, 2020.

SEQUENCE LISTING

The content of the electronically submitted sequence listing, file name: Q284898_Sequence_Listing_As_Filed.TXT; size: 11,608 bytes; and date of creation: Mar. 3, 2023, is hereby incorporated by reference in their entirety.

TECHNICAL FIELD

The present invention relates to a composition for preventing or treating *Staphylococcus aureus* infectious disease containing, as an active ingredient, a specific combination of toxins derived from *Staphylococcus aureus*.

BACKGROUND ART

*Staphylococcus aureus* is a gram-positive bacterium that causes severe infections in human skin, soft tissue and blood flow, and may evolve into methicillin-resistant *S. aureus* (MRSA), which is resistant to the beta-lactam antibiotic methicillin, through various pathways. Infections with MRSA are difficult to treat and have a poor prognosis, causing huge social costs.

*S. aureus* bi-component leukocidins (BCLs) are important virulence factors belonging to the pore-forming toxin (PFT) family. Each BCL has two subunits that are classified as the host cell-targeting S-component (for slow migration in chromatography columns: LukS-PV, LukE, HlgA, HlgC and LukA) and the polymerization F-component (for fast migration in chromatography columns: LukF-PV, LukD, HlgB and LukB). On the other hand, LukAB is secreted as a pre-assembled soluble heterodimer, and *S. aureus* α-toxin (Hla) is a single component forming β-barrel PFT.

*S. aureus* BCL toxins and Hla induce lysis of host cells such as neutrophils, monocytes/macrophages, and red blood cells (RBCs) by binding to receptors specifically expressed on the host cell surface. LukSF-PV and HlgCB use C5aR1 and C5aR2 as receptors, LukED uses CCR5, CXCR1 and CXCR2 as receptors, and HlgAB and LukED use CXCR1 and CXCR2 as receptors, but may also use CCR2 and DARC (Duffy receptor for chemokines) receptors, while LukAB binds to CD11b. Hla recognizes the ADAM10 protein expressed in cell membranes of RBCs, epithelial cells, endothelial cells, and immune cells such as neutrophils, monocytes/macrophages, and T cells.

Until now, all human clinical trials of vaccines developed for the purpose of preventing invasive *S. aureus* infection have failed. Although most vaccines produced high-titer opsonic antibodies against *S. aureus* surface antigens, they were not ultimately developed as effective vaccines, due to an incomplete understanding of the host immune mechanism and *S. aureus* infection mechanisms and the absence of means enabling the induction of sustainable long-term immunity against *S. aureus* in humans.

Recently, two new approaches have been taken to develop *S. aureus* vaccines. The first approach is to use the *S. aureus* surface antigen to induce opsonophagocytosis through antibodies generated by immunization. The generated antibodies were expected to bind to bacterial surfaces and kill the bacteria, but these opsonic antibody-based vaccine candidates were not effective in clinical trials, and some candidates showed detrimental results when actual *S. aureus* infection occurred (Fowler V G, et al., 2013, *Jama* 309: 1368-78). The other approach is to use *S. aureus* toxoids as vaccine candidates, and this strategy is to induce neutralizing antibodies through immunization with multiple toxoid antigens.

It was reported that a total of 11 components, including five *S. aureus* BCLs and Hla (α-toxin), specifically recognize five different receptor families, that is, chemokine receptor, complement receptor, CD11b receptor, DARC receptor, and ADAM 10 receptor, which are expressed in host cells and RBCs, respectively (Wilke G A et al., 2010, *Proc Natl Acad Sci USA* 107:13473-8). In immunization using active toxin components, these components are difficult to use as vaccines due to their toxicity, and immunization with all 11 toxoid proteins involves difficulty in production.

Accordingly, the present inventors have attempted to discover the most efficient combination of toxin candidates for broadly blocking 11-toxin-mediated cytotoxicity with antibodies generated by immunization. In addition, the present inventors have attempted to develop a practical preventive vaccine or therapeutic agent that can comprehensively remove or alleviate comprehensive pathological conditions caused by infection, away from piecemeal amelioration of individual symptoms caused by *S. aureus* infection, by exploring protein fragments and combinations thereof that can best induce opsonophagocytosis and most effectively control blood coagulation in infected subjects.

Through the specification, a number of publications and patent documents are referred to and cited. The disclosure of the cited publications and patent documents is incorporated herein by reference in its entirety to more clearly describe the state of the related art and the present invention.

DISCLOSURE

Technical Problem

The present inventors have made extensive research efforts to develop a composition for preventing or treating *Staphylococcus aureus* infectious disease, which is able to effectively block lysis of host cells by significantly neutralizing cytotoxicity caused by *Staphylococcus aureus* infection. To this end, the present inventors have investigated the cross-reactivity of antibodies with each toxin derived from *Staphylococcus aureus* and, based on the investigation results, explored an optimal combination that exhibit the broadest neutralization activity. As a result, the present inventors have found that, when three or more of Hla, LukS, LukAB and HlgA single toxins, more specifically, all the four toxins are combined, antibodies generated in a subject by immunization with these toxins can thoroughly block all *Staphylococcus aureus* toxin-mediated cytolytic activity and significantly inhibit blood hemolytic activity, thereby completing the present invention.

Therefore, an object of the present invention is to provide a composition for preventing or treating *Staphylococcus aureus* infectious disease.

Another object of the present invention is to provide a composition for preventing or treating a thrombotic disorder caused by *Staphylococcus aureus* infection.

Other objects and advantages of the present invention will become more apparent from the following detailed description of the invention, the appended claims and the accompanying drawings.

Technical Solution

In accordance with one aspect of the present invention, the present invention provides a composition for preventing or treating *Staphylococcus aureus* infectious disease comprising, as an active ingredient, at least three *Staphylococcus aureus*-derived toxins selected from the group consisting of alpha-hemolysin (Hla), Leukocidal toxin S (LukS), Leukocidal toxin AB (LukAB) and gamma-hemolysin (HlgA), or antibodies or antigen-binding fragments thereof that specifically recognize the toxins, or nucleotides encoding the toxins.

The present inventors have made extensive research efforts to develop a composition for preventing or treating *Staphylococcus aureus* infectious disease, which is able to effectively block lysis of host cells by significantly neutralizing cytotoxicity caused by *Staphylococcus aureus* infection. To this end, the present inventors have investigated the cross-reactivity of antibodies with each toxin derived from *Staphylococcus aureus* and, based on the investigation results, explored an optimal combination that exhibit the broadest neutralization activity. As a result, the present inventors have found that, when three or more of Hla, LukS, LukAB and HlgA toxins, more specifically, all the four toxins are combined, antibodies generated in a subject by immunization with these toxins can thoroughly block all *Staphylococcus aureus* toxin-mediated cytolytic activity and significantly inhibit blood hemolytic activity.

The composition of the present invention may be in the form of a vaccine comprising each toxin protein or a nucleotides encoding the same, which is administered to a subject to generate an antibody against each toxin in the subject, and it may also be used in the form of an antibody therapeutic agent containing an isolated/purified antibody against each toxin as a pharmacological ingredient. Accordingly, in the former case, the term "composition for preventing or treating *Staphylococcus aureus* infectious disease" has the same meaning as "*Staphylococcus aureus* vaccine composition".

As used herein, the term "antibody" refers to an immunoglobulin protein generated by the mammalian immune system, in which the immunoglobulin protein comprises one or more variable domains binding to an epitope of an antigen, and specifically recognizes the antigen. As the antibody that specifically recognizes each *Staphylococcus aureus* toxin in the present invention, a polyclonal or monoclonal antibody may be used, and specifically, a polyclonal antibody having cross-reactivity may be used.

The antibodies of the present invention may be produced by methods that are commonly used in the art, for example, a fusion method (Kohler and Milstein, *European Journal of Immunology,* 6:511-519 (1976)), a recombinant DNA method (U.S. Pat. No. 4,816,567), a phage antibody library method (Clackson et al, *Nature,* 352:624-628(1991), or the method reported in Marks et al, *J. Mol. Biol.,* 222:58, 1-597(1991)). General procedures for antibody production are described in detail in Harlow, E. and Lane, D., *Using Antibodies: A Laboratory Manual*, Cold Spring Harbor Press, New York, 1999; and Zola, H., *Monoclonal Antibodies: A Manual of Techniques*, CRC Press, Inc., Boca Raton, Florida, 1984.

As used herein, the term "antigen binding fragment" refers to a fragment of the whole immunoglobulin structure which possesses a part of a polypeptide responsible for binding to antigen. Examples of the antigen binding fragment include, but are not limited to, F(ab')2, Fab', Fab, Fv and scFv.

As used herein, the term "specifically binding" has the same meaning as "specifically recognizing", and means that an antigen and an antibody (or a fragment thereof) specifically interact through an immunological reaction.

The present invention may also be used in the form of a DNA vaccine or mRNA vaccine containing, as an active ingredient, nucleotides encoding the amino acids of the above-described four toxins.

As used herein, the term "nucleotide" refers to a deoxyribonucleotide or ribonucleotide polymer in single-stranded or double-stranded form, including analogs of natural nucleotides unless otherwise specified (Scheit, *Nucleotide Analogs*, John Wiley, New York (1980); Uhlman and Peyman, *Chemical Reviews,* 90:543-584(1990)). When the present invention is used in the form of a DNA vaccine or mRNA vaccine, the three or four toxin genes of the present invention may be contained in each gene delivery system, or a plurality of toxin antigen genes may be simultaneously inserted into one gene delivery system and expressed in a subject.

As used herein, the term "express" means allowing a subject to express an exogenous gene or artificially introducing an endogenous gene using a gene delivery system to increase the natural expression level of the endogenous gene, thereby making the gene replicable as an extrachromosomal factor by chromosomal integration in the subject's cell. Accordingly, the term "expression" is synonymous with "transformation", "transfection" or "transduction".

As used herein, the term "gene delivery system" refers to a vehicle for introducing a desired target gene into a target cell to express the target gene. An ideal gene delivery system should be nontoxic to the human body, easily mass-produced, and efficiently deliver a gene.

As used herein, the term "gene delivery" means delivering the gene into cells, and has the same meaning as cellular transduction of the gene. At the tissue level, the term "gene delivery has the same meaning as spread of the gene. Thus, the gene delivery system of the present invention may be referred to as a gene transduction system and a gene spread system.

To construct the gene delivery system of the present invention, the nucleotide sequence of the present invention is preferably present within a suitable expression construct and operatively linked to an expression regulatory sequence (e.g., a promoter, a signal sequence, or an array of transcription regulation factor binding sites). As used herein, the term "operatively linked" refers to a functional linkage between a nucleic acid expression regulatory sequence and another nucleic acid sequence, and through the linkage, the regulatory sequence regulates the transcription and/or translation of the other nucleic acid sequence.

The gene delivery system of the present invention may be constructed in various forms. Specifically, the gene delivery system may be constructed in a form of: (i) naked recombinant DNA molecule, (ii) plasmid, (iii) viral vector, (iv) liposome or niosome including the naked recombinant DNA molecule or plasmid, or (v) liposome including mRNA.

According to a specific embodiment of the present invention, the Hla is a variant in which the amino acid residue at position 35 of the amino acid sequence of Hla (alpha-hemolysin) protein is substituted. More specifically, the amino acid residue His at position 35 is substituted with Leu.

According to a specific embodiment of the present invention, the LukAB is a variant in which the amino acid residue Glu at position 323 of the amino acid sequence of the LukAB (Leukocidin AB) protein is substituted. More specifically, the amino acid residue Glu at position 323 is substituted with Ala.

As used herein, the term "prevention" means inhibiting the occurrence of a disorder or a disease in a subject who has never been diagnosed as having the disorder or disease, but is likely to suffer from such disorder or disease.

As used herein, the term "treatment" means (a) inhibiting the progress of a disorder, disease or symptom; (b) alleviating the disorder, disease or symptom; or (c) eliminating the disorder, disease or symptom. When the composition of the present invention is administered to a subject, it functions to inhibit the progress of symptoms caused by *Staphylococcus aureus* infection, or to eliminate or alleviate the symptoms by effectively inhibiting a wide spectrum of cytolytic activity mediated by 11 toxins derived from *Staphylococcus aureus*. Thus, the composition of the present invention may serve as a therapeutic composition for the disease alone, or may be administered in combination with other pharmacological ingredients and applied as a therapeutic aid for the disease. Accordingly, as herein used, the term "treatment" or "therapeutic agent" encompasses "treatment aid" or "therapeutic aid agent".

As used herein, the term "administration" or "administering" means administering a therapeutically effective amount of the composition of the present invention directly to a subject so that the same amount is formed in the subject's body.

As used herein, the term "therapeutically effective amount" refers to an amount of the composition containing a pharmacological ingredient sufficient to provide a therapeutic or prophylactic effect to a subject to whom the pharmaceutical composition of the present invention is to be administered. Accordingly, the term "therapeutically effective amount" encompasses a "prophylactically effective amount".

As used herein, the term "subject" includes, without limitation, humans, mice, rats, guinea pigs, dogs, cats, horses, cows, pigs, monkeys, chimpanzees, baboons or rhesus monkeys. Specifically, the subject of the present invention is a human.

According to a specific embodiment of the present invention, the *Staphylococcus aureus* may be methicillin-resistant *Staphylococcus aureus* (MRSA), methicillin-sensitive *Staphylococcus aureus* (MSSA), or pathogenic *Staphylococcus aureus*, and more specifically, is methicillin-resistant *Staphylococcus aureus*.

Examples of *Staphylococcus aureus* infectious diseases include, but are not limited to, soft tissue infection, suppurative arthritis, suppurative osteomyelitis, otitis media, pneumonia, sepsis, acute respiratory tract infection, infection due to the use of a catheter, post-surgery wound infection, bacteremia, endocarditis, and food poisoning.

According to a specific embodiment of the present invention, the composition of the present invention may additionally contain a glycopeptide-based antibiotic in addition to the above-described *Staphylococcus aureus*-derived toxins as an active ingredient.

As used herein, the term "glycopeptide-based antibiotic" refers to a hydrophilic antibiotic having a molecular weight of about 1,400 Da or more and having a glycopeptide core, which is a fused ring structure to which monosaccharides are bound. The glycopeptide-based antibiotic inhibits bacterial peptidoglycan synthesis, and examples thereof include, but are not limited to, ramoplanin, dalbavancin, oritavancin, telavancin, vancomycin, and teicoplanin. Any glycopeptide-based antibiotic known in the art may be used.

Specifically, the glycopeptide-based antibiotic used in the present invention is selected from the group consisting of vancomycin, teicoplanin, and a combination thereof.

As shown in Examples to be described later, it was confirmed that, when a combination of toxins discovered in the present invention or an isolated/purified antibody against these toxins was co-administered with a glycopeptide-based antibiotic such as vancomycin or teicoplanin, it could completely eliminate even residual bacteria in the kidneys and further improve the survival rate of the infected individual, thereby exhibiting a multifaceted and synergistic protective effect on the patient.

The co-administration may be performed using a single formulation containing all the toxins of the present invention and the glycopeptide-based antibiotic, or may be performed by administering separate formulations containing the toxins and the glycopeptide-based antibiotic, respectively, simultaneously or sequentially with appropriate time delays in any order. In the case of sequential administration, for example, the toxins of the present invention or an isolated/purified antibody against the toxins may be administered first, and then the glycopeptide-based antibiotic may be administered.

According to another aspect of the present invention, the present invention provides a method for preventing or treating *Staphylococcus aureus* infectious disease, the method comprising a step of administering the above-described composition of the present invention to a subject.

According to still another aspect of the present invention, the present invention provides a composition for preventing or treating *Staphylococcus aureus* infectious disease comprising, as an active ingredient, at least one protein selected from the group consisting of clumping factor A (ClfA), fibrinectin-binding protein A (FnbpA), fibrinectin-binding protein B (FnbpB), and functional portions thereof, or an antibody or antigen-binding fragment thereof that specifically recognizes the protein, or a nucleotide encoding the protein.

Since the antibody or antigen-binding fragment thereof and nucleotide that are used in the present invention and the *Staphylococcus aureus* infectious disease to be prevented or treated with the composition of the present invention have already been described in detail, description thereof will be omitted to avoid excessive overlapping.

The present inventors also have made extensive research efforts to explore compositions that prevent or treat *Staphylococcus aureus* infectious disease by neutralizing the host immune system evasion system unique to *Staphylococcus aureus*, or compositions that improve the therapeutic sensitivity of *Staphylococcus aureus* therapeutic compositions, including vaccines. As a result, the present inventors have found that, when a combination of one or more selected from the group consisting of ClfA, FnbpA, FnbpB, and functional portions thereof, which are proteins belonging to MSCRAMM (microbial surface components recognizing adhesive matrix molecules), is administered to a subject, these proteins competitively bind to factor H (human complement factor H, FH) in host serum instead of MSCRAMM on the surface of live bacterial cells, thereby blocking the hydrolysis of complement C3b to iC3b, and bacterial opsonophagocytosis is promoted by C3b with retained activity.

As used herein, the term "functional portion" is meant to encompass a partial fragment of any length that retains the biological activity of the ClfA, FnbpA or FnbpB protein. Thus, the term "functional portion of the ClfA, FnbpA or FnbpB protein" refers to a partial fragment of each protein that is capable of specifically interacting with serum FH or capable of functioning as an antigen that induces the generation of an antibody capable of binding specifically to MSCRAMM on the surface of live bacterial cells.

According to a specific embodiment of the present invention, the functional portion is a fragment comprising the N2-N3 domain of the protein, more specifically, the N2-N3 domain ($ClfA^{N2N3}$, $FnbpA^{N2N3}$ or $FnbpB^{N2N3}$) of the protein. The interactions of $ClfA^{N2N3}$, $FnbpA^{N2N3}$ and $FnbpB^{N2N3}$ with FH are unknown, and the present inventors have found first that these fragments can competitively bind to FH, or antibodies against these fragments can competitively bind to MSCRAMM on the surface of live bacterial cells, thereby effectively blocking the interaction between FH in host serum and MSCRAMM on the surface of live bacterial cells.

According to a specific embodiment of the present invention, the composition of the present invention contains, as an active ingredient, a partial fragment comprising the N2-N3 domain of ClfA and a partial fragment comprising the N2-N3 domain of FnbpB, or antibodies or antigen-binding fragments thereof that specifically recognize the fragments, or nucleotides encoding the fragments.

When the composition of the present invention is prepared as a pharmaceutical composition, the pharmaceutical composition of the present invention contains a pharmaceutically acceptable carrier.

Examples of the pharmaceutically acceptable carrier that is contained in the pharmaceutical composition of the present invention include, but are not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, and mineral oil, which are commonly used in formulation. The pharmaceutical composition of the present invention may further contain a lubricant, a wetting agent, a sweetening agent, a flavoring agent, an emulsifying agent, a suspending agent, a preservative, and the like, in addition to the above-described components. Suitable pharmaceutically acceptable carriers and agents are described in detail in Remington's Pharmaceutical Sciences ($19^{th}$ ed., 1995).

The pharmaceutical composition of the present invention may be administered orally or parenterally. Specifically, it may be administered intravenously, subcutaneously or intraperitoneally.

An appropriate dosage of the pharmaceutical composition of the present invention may vary depending on various factors such as formulation method, administration mode, patient's age, weight, sex, pathological condition, diet, administration time, administration route, excretion rate, and reaction sensitivity. A preferred dosage of the pharmaceutical composition of the present invention is within the range of 0.001 to 100 mg/kg for an adult.

The pharmaceutical composition of the present invention may be prepared in a unit dose form or prepared to be contained in a multi-dose container by formulating with a pharmaceutically acceptable carrier and/or excipient, according to a method that may be easily carried out by a person skilled in the art to which the present invention pertains. Here, the formulation of the pharmaceutical composition may be a solution, suspension, syrup or emulsion of the pharmaceutical composition in oil or aqueous medium, or an extract, powder, granule, tablet or capsule containing the pharmaceutical composition, and may further contain a dispersing agent or a stabilizer.

When the pharmaceutical composition of the present invention is prepared as a vaccine composition, a plurality of antigens of the present invention, and optionally combined suitable adjuvants in various forms, may be packaged in one vial or prefilled syringe, or each antigen and adjuvant may be packaged in separate vials and mixed immediately prior to use (bedside mixing).

According to yet another aspect of the present invention, the present invention provides a method for preventing or treating *Staphylococcus aureus* infectious disease, the method comprising a step of administering the above-described composition of the present invention to a subject.

According to still yet another aspect of the present invention, the present invention provides a composition for preventing or treating a thrombotic disorder caused by *Staphylococcus aureus* infection comprising, as an active ingredient, at least one protein selected from the group consisting of coagulase (Coa), von Willebrand factor binding protein (vWbp), and functional portions thereof, or an antibody or antigen-binding fragment thereof that specifically recognizes the protein, or a nucleotide encoding the protein.

The present inventors have made extensive research efforts to develop a method of minimizing systemic damage to patients, which is caused by blood coagulation during infection, and further improving the survival of patients, by efficiently blocking the host immune system evasion mechanism unique to *Staphylococcus aureus* that induces fibrin coagulation in host blood vessels. As a result, the present inventors have found that, when coagulase (Coa) and von Willebrand factor binding protein (vWbp), specifically, specific functional fragments thereof, which are known as the main virulence factors of *Staphylococcus aureus*, are used, blood coagulation is significantly inhibited by antibodies generated by immunization therewith.

The term "functional portion" used herein while referring to Coa or vWbp protein is meant to encompass any partial fragment of any length that retains the biological activity of the Coa or vWbp protein. Thus, term "functional portion" refers to a partial fragment of each protein that may function as an antigen that induces the generation of an antibody which is recognized by *Staphylococcus aureus* surface protein (e.g., Fnbp) or significantly inhibits blood coagulation caused by *Staphylococcus aureus* infection.

According to a specific embodiment of the present invention, the functional portion of Coa is an N-terminal fragment of Coa protein, more specifically, a fragment comprising 284 consecutive amino acid residues from the N-terminus.

According to a specific embodiment of the present invention, the functional portion of vWbp is an N-terminal fragment of vWbp protein, more specifically, a fragment comprising 253 consecutive amino acid residues from the N-terminus of vWbp protein.

As used herein, the term "thrombotic disorder" refers to a systemic disease in which blood flow is reduced or blocked due to blood clots generated by platelet coagulation or fibrin protein aggregation in the vascular microcirculatory system, causing ischemic injury in each organ such as the kidney, heart, or brain.

Specifically, the thrombotic disorder caused by *Staphylococcus aureus* infection, which is to be prevented or treated with the composition of the present invention, is at least one disorder selected from the group consisting of stroke, cerebral infarction, cerebral thrombosis, cerebral embolism, lacunar cerebral infarction, acute coronary syndrome, angina pectoris, aortic stenosis, myocardial infarction, bundle-branch block, cerebral ischemia, acute ischemic arteriovascular event, thrombophlebitis, venous thromboembolism, deep vein thrombosis, pulmonary embolism, peripheral vascular disease, atherosclerosis, vasospasm, and restenosis, which are caused by *Staphylococcus aureus* infection.

According to another aspect of the present invention, the present invention provides a method for preventing or treating a thrombotic disorder caused by *Staphylococcus aureus* infection, the method comprising a step of administering the above-described composition of the present invention to a subject.

Advantageous Effects

The features and advantages of the present invention are summarized as follows:

(a) The present invention provides a composition for preventing or treating *Staphylococcus aureus* infectious disease and a composition for preventing or treating a thrombotic disorder caused by *Staphylococcus aureus* infection.

(b) According to the present invention, cell lysis by 11 toxins of *Staphylococcus aureus* can be thoroughly inhibited by using the cross-reactivity of antibodies against *Staphylococcus aureus* toxins, even with a minimal combination of toxin antigens.

(c) The present invention can also be usefully used as an effective therapeutic composition that can comprehensively remove or alleviate comprehensive pathological conditions caused by infection, away from piecemeal amelioration of individual symptoms caused by *Staphylococcus aureus* infection, by inducing opsonophagocytosis and effectively controlling blood coagulation in infected subjects.

BRIEF DESCRIPTION OF DRAWINGS

FIG. 1*a*, cloned seven single component genes; FIG. 1*b*, cloned gene containing LukAB dimer gene; FIG. 1*c*, Hla gene; FIG. 1*d*, $Hla_{H35L}$; FIG. 1*e*, $LukS_{T244A}$; and FIG. 1*f*, $LukA_{E323A}B$.

FIG. 2 is a schematic view of constructed *S. aureus* recombinant wild type and toxoid BCL toxins in the present invention.

FIG. 3 shows the results of purifying recombinant BCLs, toxoids, toxin and the results of measuring cytolytic activities thereof. FIG. 3*a* shows the results of loading 5 μg of each protein on 15% SDS-PAGE under reducing conditions. FIG. 3*b* shows the SDS-PAGE pattern of 5 μg of toxoid proteins. FIG. 3*c* shows the results of co-culturing human PMNs ($2\times10^6$ cells) with 0.125 μg of purified BCLs and toxoids for 1 hour. Columns 1, no-toxin; 2, $LukS_{T244A}$-PV+LukF-PV; 3, $LukA_{E323A}B$; 4, LukS-PV+LukF-PV; 5, LukE+LukD; 6, HlgC+HlgB; 7, HlgA+HlgB; 8, LukAB. FIG. 3*d* shows the results of co-culturing 2% rabbit RBCs with $Hla_{WT}$ (0.25 μg) and $Hla_{H35L}$ (0.25 μg) toxoid for 1 hour at 37° C. Columns: 1, PBS; 2, $Hla_{WT}$; 3, $Hla_{H35L}$.

FIG. 4 shows elution patterns of rabbit anti-BCL recognizing IgGs purified from BCL-immunized rabbit sera. First, rabbit sera (120 mg) was loaded on protein-A Sepharose column (Sigma-Aldrich) and bound total IgGs were eluted with 0.15 M glycine buffer (pH 2.2) (data not shown). After concentration, collected IgGs were loaded on each toxin and toxoid-conjugated Sepharose columns and then eluted with 0.15 M glycine buffer (pH 2.2).

FIG. 5 shows recognition patterns against rabbit single BCLs by anti-BCL IgGs on immuno-dot blot assay. Each purified single BCL component (1 μg) was spotted on the PVDF strip which was then incubated with each cognate anti-BCL-IgG for 1 hour at room temperature. After washing, each strip was incubated with HRP-conjugated goat anti-rabbit-IgG.

FIG. 10 shows

column 3, LukE+LukD (yellowish green); column 4, LukS-PV+LukF-PV (blue); column 5, HlgC+HlgB (yellow); column 6, LukAB (orange).

Figure 11A:
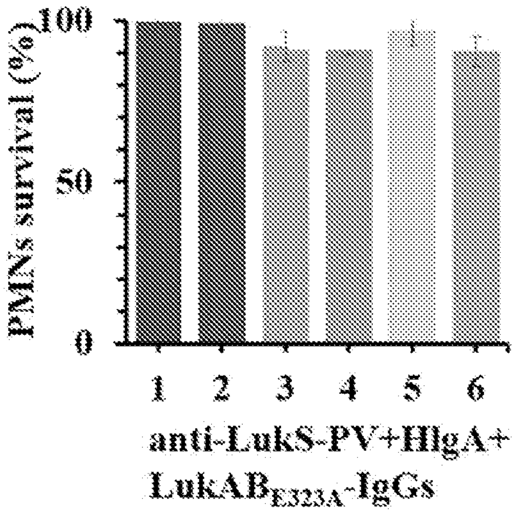
Figure 11B:
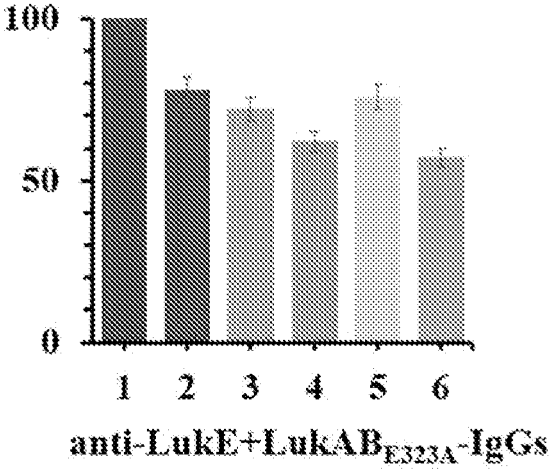
Figure 11C:
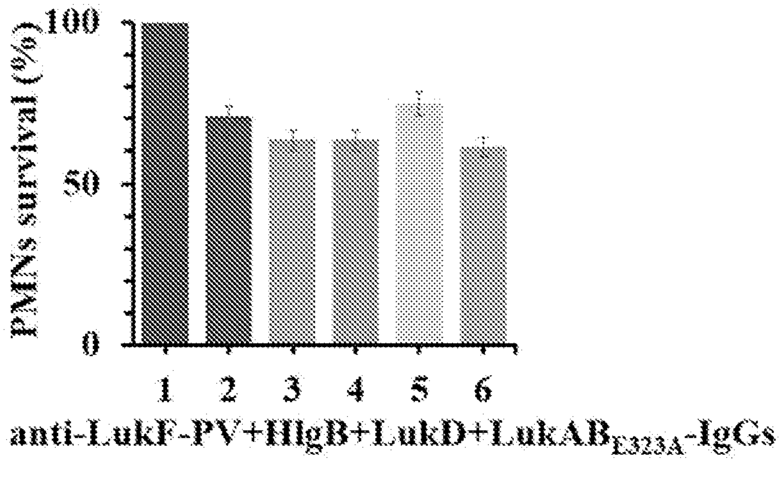

FIGS. 11*a* to 11*c* show human PMN survival rates upon co-incubation of PMNs ($2\times10^6$ cells) with the mixture of cognate S-component (0.25 μg/ml) and F-component (0.25 μg/ml) of BCLs in the presence of each purified anti-LukS-PV+HlgA+$LukAB_{E323A}$-IgGs (FIG. 11*a*), anti-LukE+$LukAB_{E323A}$-IgGs (FIG. 11*b*), and anti-LukF-PV+HlgB+LukD+$LukAB_{E323A}$-IgGs (FIG. 11*c*). Column 1, no toxin (green); column 2, HlgA+HlgB (brown); column 3, LukE+LukD (yellowish green); column 4, LukS-PV+LukF-PV (blue); column 5, HlgC+HlgB (yellow); column 6, LukAB (orange).

FIG. 12 shows expression patters of cognate BCLs and Hla at different time points. In lane 1, the mixture of purified recombinant single S-component (0.2 μg) and F-component (0.2 μg) were loaded on the gel. The culture media (60 μg protein amounts) obtained from *S. aureus* USA300 LAC cell culture at 0 h (lane 2), 1, 5 h (lane 3), 4 h (lane 4), 5 h (lane 6) and 9 h (lane 6) were purified and loaded on 15% SDS-PAGE gel. Thereafter, Western blot analysis was carried out using the mixture of affinity-purified anti-single S- and F-component-IgG (each 6 μg).

Figure 13A:
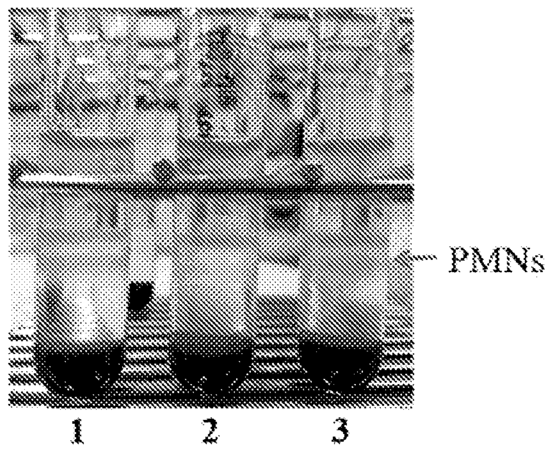
Figure 13B:
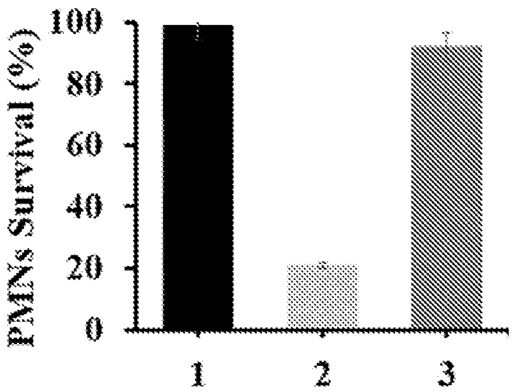
Figure 13C:
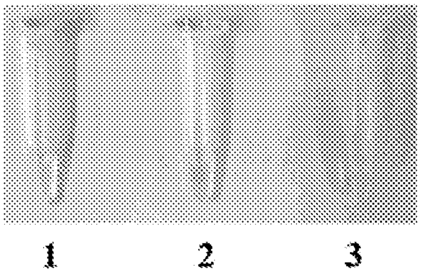
Figure 13D:
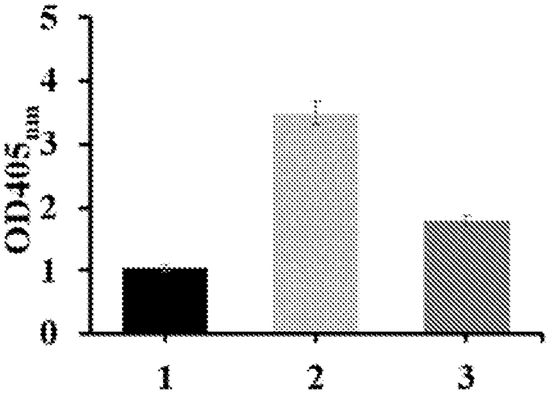

FIGS. 13*a* to 13*d* show the effects of selected 4 IgGs against six-toxin-mediated human PMN cytolytic activity (FIG. 13*a*), the results of counting the number of survived PMN cells (FIG. 13*b*), images of six-toxin-treated rabbit RBCs (FIG. 13*c*), and their absorbance measurement results at 405 nm (FIG. 13*d*).

Figure 14A:
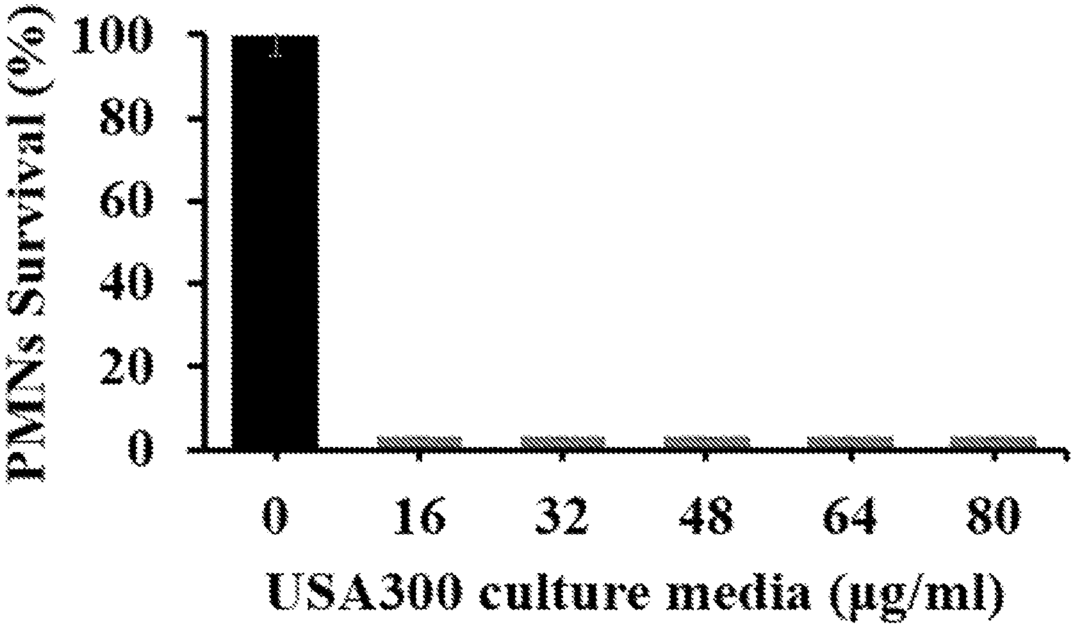

FIGS. 14*a* and 14*b* show the results of measuring human PMN survival by treatments of USA300 culture medium (FIG. 14*a*) and by treatments of culture medium and selected four toxin and toxoid IgGs (FIG. 14*b*).

FIG. 15 shows the results of CFU estimation after co-incubation of *S. aureus* USA300 LAC cells with human whole blood, PBS, rabbit naïve serum or four selected toxin and toxoid IgGs. In column 1, human whole blood (2 ml) was co-incubated with bacteria ($2\times10^6$ cells) with PBS (20 μl) for 3 hours at 37° C. In column 2, instead of PBS, naïve rabbit serum (40 μg of protein) was added. In column 3, selected four toxin and toxoid IgGs were added.

FIG. 16 shows domain structures of *S. aureus* CWAP proteins (FIG. 16*a*), cloned $CWAP^{N2N3}$ domains in the present invention (FIG. 16*b*), and the results of SDS-PAGE analysis of purified seven $CWAP^{N2N3}$ domains (FIG. 16*c*). The primary translation products of *S. aureus* CWAP proteins contain signal sequences (S) at the N-terminus and three separately folded domains called N1, N2 and N3. The C-terminus has a wall-spanning region (W) and sorting signal (SS).

FIG. 17 shows $CWAP^{N2N3}$ immuno-dot blot analyses and conversion of C3b to iC3b in the presence of $CWAP^{N2N3}$/FH/FI. FIG. 17*a* shows the results of dot blot immune assay in which seven $CWAP^{N2N3}$ domains ($ClfA^{N2N3}$, $ClfB^{N2N3}$, $SdrC^{N2N3}$, $SdrD^{N2N3}$, $FnbpA^{N2N3}$, and $FnbpB^{N2N3}$) and BSA were spotted on five strips of PVDF membranes. FIG. 17*b* shows cleavage of C3b into iC3b via human FH/FI/$CWAP^{N2N3}$ domains on the immobilized plate.

FIG. 18 shows that $CWAP^{N2N3}$ proteins captured FH and inhibited conversion of C3 to iC3b. FIG. 18*a* shows the results of SDS-PAGE gel electrophoresis in which 5 μg of $CWAP^{N2N3}$ domain proteins and 0.5 μg of FH were added to *S. aureus* USA300 LAC cells ($1\times10^5$ CFUs) suspended in 100 μl of PBS. FIG. 18*b* shows the results of SDS-PAGE gel electrophoresis in which 10 μg of $CWAP^{N2N3}$ domains and 0.1 μg of human FH were added to 100 μl of $GVB^{++}$ containing *S. aureus* USA300 LAC cells ($1\times10^5$ CFUs).

FIG. 19 shows flow cytometry results indicating that binding of FH to live *S. aureus* USA300 cells was inhibited by treatment with anti-FH-binding CWAP-Fab'2 fragments (FIG. 19*a*), and shows the results of quantifying such inhibitory effects through deposited FH amounts on the bacterial surface (FIG. 19*b*). *, p≤0.05; , p≤0.01; *, p≤0.001; NS: statically non-significant.

FIG. 20 shows Western blot analysis results indicating the binding specificity of purified rabbit (FIG. 20*a*) and human (FIG. 20*b*) anti-CWAP-IgG against seven $CWAP^{N2N3}$ domains ($ClfA^{N2N3}$, $ClfB^{N2N3}$, $SdrC^{N2N3}$, $SdrD^{N2N3}$, $SdrE^{N2N3}$, $FnbpA^{N2N3}$ and $FnbpB^{N2N3}$).

FIG. 21 shows bactericidal activities of *S. aureus* by $CWAP^{N2N3}$ domain and by purified human or rabbit $CWAP^{N2N3}$ recognizing IgGs. FIG. 21*a* shows the results of measuring CFU after adding 5 μg of each of purified $CWAP^{N2N3}$ domains to 100 μl of *S. aureus* USA300 LAC cells ($1\times10^5$ cells/well). Statistical analysis was performed using unpaired student's t-test. *, p≤0.05; NS: statically non-significant. Also, it shows the results of measuring CFU after adding purified human (FIG. 21*b*) and rabbit (FIG. 21*c*) IgG to 100 μl of *S. aureus* USA300 LAC cells ($1\times10^5$ cells/well). Statistical analysis was performed using unpaired student's t-test. *, p≤0.05; , p≤0.01; *, p≤0.001; ***, p≤0.0001; NS: statically non-significant.

FIG. 22 is a schematic view showing the mechanism of action of the composition of the present invention. Most of *S. aureus* strains are known to express CWAP on their surfaces. When bacteria invade host, serum complement FH will bind $CWAP^{N2N3}$ domains by DLL mechanism (14, 15). Simultaneously, human complement activation will deposit C3b on their surface upon bacteria recognition. Subsequently, FH will recruit FI to convert deposited C3b to iC3b, leading to the decrease of C3b-mediated opsonophagocytosis by host neutrophils (middle figure). By binding of anti-$CWAP^{N2N3}$-IgGs to native proteins expressed on bacteria surface, there is no chance for FH to binding these $CWAP^{N2N3}$ domains. By inhibition of FH recruitment on bacteria, FI-mediated C3b inactivation will be also decreased. Higher amounts of C3b will induce higher chance of C3b-mediated opsonophagocytosis (left figure). By addition of $CWAP^{N2N3}$ domains into *S. aureus* infected sites, these proteins will capture serum FH and give higher chance of C3b deposition on the bacterial surface, leading to enhanced C3b-mediated opsonophagocytosis (right figure).

FIG. 23 shows the results of confirming cloned *S. aureus* $CWAP^{N2N3}$ domain genes.

FIG. 24*a* shows SDS-APGE patterns of purified anti-FH-IgG and anti-FH-Fab'2 under-reducing (left) and non-reducing (right) conditions. Lane 1, goat anti-human factor H IgG; lane 2, pepsin-treated goat anti-human factor H IgG; lane 3, pass-through fraction of protein A column; lane 4, fraction of pepsin-treated goat anti-human factor H on protein A column. FIG. 24*b* shows the binding specificity of anti-FH-IgG and anti-FH-Fab'2 fragments against six proteins. FIG. 24*c* shows the binding specificity of five anti-CWAP-Fab'2 fragments against seven different $CWAP^{N2N3}$ domains.

FIG. 25 shows elution patterns of four human (FIG. 25*a*) and rabbit (FIG. 25*b*) anti-CWAP-IgGs.

FIG. 26 shows the results of SDS-PAGE analysis of purified human (FIG. 26*a*) and rabbit (FIG. 26*b*) anti-CWAP-IgGs. SH(+) and SH(−) indicate reducing and non-reducing conditions, respectively. Lanes 1 to 5 were loaded with ClfA-IgG, SdrC-IgG, SdrE-IgG, FnbpA-IgG, and FnboB-IgG, respectively. Each lane was loaded with 3 μg of purified IgGs.

FIG. 27 shows the scheme of domain components of *S. aureus* coagulase (Coa) and vWF-binding domain proteins (vWbp), and shows constructed domains of the recombinant Coa (FIG. 27*a*) and vWbp (FIG. 27*b*). The numbers indicate the amino acids positions based on genome sequences of *S. aureus* USA300 LAC strain.

FIG. 28 shows the results of SDS-PAGE analysis (15%) of the purified recombinant Coa and vWbp domain proteins. Lane 1, $Coa^{whole}$; lane 2, $Coa^{N}$; lane 3, $Coa^{C}$; lane 4, $vWbp^{whole}$; lane 5, $vWbp^{N}$; lane 6, $vWbp^{C}$.

FIG. 29 shows the results of examining antibody-specificity against different domain proteins of Coa (FIG. 29*a*) and vWbp (FIG. 29*b*) by dot blot analyses. Lane 1, BSA (3 μg); lane 2, $Coa^{whole}$ (3 μg); lane 3, $Coa^{N}$ (3 μg); lane 4, $Coa^{C}$ (3 μg); lane 5, BSA (3 μg); lane 6, $vWbp^{whole}$ (3 μg); lane 7, $vWbp^{N}$ (3 μg); lane 8, $vWbp^{C}$ (3 μg).

FIG. 30 shows expression patterns of Coa (FIG. 30*a*) and vWbp (FIG. 30*b*) proteins during *S. aureus* USA300 culture, and shows the results of performing Western blot analysis using anti-$Coa^{whole}$-IgG (FIG. 30*a*) and anti-vWbp-IgG (FIG. 30*b*). The left-side gels indicate the SDS-PAGE patterns of purified $Coa^{whole}$ and $vWbp^{whole}$.

FIG. 31 shows the results of identifying Coa (FIG. 31*a*) and vWbp (FIG. 31*b*)-recognition proteins expressed on the *S. aureus* cell surface by dot blot analysis. Seven N2-N3 domains of cell wall-associated proteins (CWAPs) (3 μg) were spotted on the seven PVDF membrane strips. Lane 1, BSA; lane 2, $ClfA^{N2N3}$; lane 3, $ClfB^{N2N3}$, lane 4, $SdrC^{N2N3}$; lane 5, $SdrD^{N2N3}$; lane 6, $SdrE^{N2N3}$; Lane 7, $FnbpA^{N2N}$; lane 8, $FnbpB^{N2N}$.

FIG. 32 shows the results of confirming the binding specificity between Coa and Fnbp proteins using anti-Fnbp-F(ab')2 fragments. *S. aureus* USA300 LAC cells ($1\times10^5$ cells) were incubated with $Coa^{C}$ for 1 hour and then obtained bacterial pellet (lane 1), showing added Coa protein was recruited on bacterial surface. As control, although bacteria cells were co-incubated with $Coa^{C}$ and anti-SdrC-F(ab)2' fragment, $Coa^{C}$ was recruited on the bacterial surface (lane 2). However, when bacteria cells were co-incubated with $Coa^{C}$ and anti-Fnbp-F(ab')2 fragments, added $Coa^{C}$ amounts were highly decreased on the bacterial surface (lanes 3 and 4). This suggests that Fnbp has the ability to selectively bind to secreted $Coa^{C}$.

FIG. 33 shows induction of blood coagulation by different dose of purified $Coa^{whole}$ or $vWbp^{whole}$ (FIG. 33*a*) and inhibitory effects of blood coagulation by different doses of anti-$Coa^{whole}$-IgG and $vWbp^{whole}$-IgGs (FIG. 33*b*).

FIG. 34 shows that secreted Coa and vWbp-mediated blood coagulation was inhibited by anti-$Coa^{whole}$ IgG or anti-$vWbp^{whole}$ IgG. Tube 1, RPMI (100 ul) plus human blood (200 μl) incubated for 1.5 h; tube 2, blood (200 μl) incubated with 1 μg of $Coa^{whole}$ for 1.5 h; tube 3, 5 μg of vWbp added to 200 μl of blood; tube 5, USA300 culture media (100 μl) plus blood; tube 6, anti-$Coa^{whole}$ IgG (80 μg) added to USA300 culture medium (100 μl) plus blood; tube 7, anti-$vWbp^{whole}$ IgG (80 μg) plus culture medium and blood; tube 8, USA300 culture medium (100 μl) plus anti-$coagulase^{whole}$ IgG (40 μg) and anti-$vWbp^{whole}$ IgG (40 μg); tube 9, USA300 culture medium (100 μl) plus anti-$Coa^{whole}$ IgG (80 μg)+anti-$vWbp^{whole}$ IgG (80 μg) plus blood.

FIG. 35 shows that only $Coa^{N}$ and $vWbp^{N}$ induced human blood coagulation, but $Coa^{C}$ and $vWbp^{C}$ did not induce blood coagulation. Tube 1, blood 200 μl plus RPMI medium (100 μl) incubated at room temperature for 1.5 h; tube 2, USA300 culture medium (100 μl) plus human blood; tube 3, blood plus $vWbp^{N}$ (5 μg); tube 4, blood plus $vWbp^{C}$ (5 μg); tube 5, blood plus $Coa^{N}$ (1 μg); tube 6, blood plus $Coa^{C}$ (1 μg).

FIG. 36 shows that blood coagulation by Coa or vWbp contained in USA300 culture medium (FIG. 36*a*) and $Coa^{N}$ and $vWbp^{N}$-mediated coagulation (FIG. 36*b*) were inhibited by anti-$Coa^{N}$-IgG and anti-$vWbp^{N}$-IgG, but not anti-$Coa^{C}$ and anti-$vWbp^{C}$ IgGs. In FIG. 36*a*, tube 1, blood 200 μl plus RPMI medium (100 μl) incubated at room temperature for 2.5 h; tube 2, blood plus culture medium (100 μl); tube 3, blood plus culture medium plus $Coa^{N}$-Ab (60 μg); tube 4, blood plus culture medium plus $vWbp^{N}$-Ab (60 μg); tube 5, blood plus culture medium plus $Coa^{C}$-Ab; tube 6, blood plus culture medium plus $vWbp^{C}$-Ab (60 μg); in FIG. 36*b*, tube 1, blood (200 μl) plus RPMT (100 μl); tube 2, blood plus $Coa^{N}$ (5 μg); tube 3, blood plus $vWbp^{N}$ (5 μg); tube 4, blood plus $Coa^{N}$ (5 μg) plus anti-$Coa^{N}$-Ab (80 μg); tube 5, blood plus $vWbp^{N}$ (5 μg) plus anti-$vWbp^{N}$-Ab (80 μg).

FIG. 37 is a schematic diagram of a rabbit immunization experiment to confirm the blood coagulation effect of anti-$Coa^{whole}$-IgG and $vWbp^{whole}$-IgG in vivo.

FIG. 38 is a graph showing the results of measuring body weight changes for up to 167 hours for each rabbit belonging to the PBS-administered control group and the anti-$Coa^{whole}$-IgG and $vWbp^{whole}$-IgG-administered groups.

FIG. 39 shows the result of calculating the survival rates of the PBS-administered control group and the anti-$Coa^{whole}$-IgG and $vWbp^{whole}$-IgG-administered groups over time (FIG. 39*a*) and daily (FIG. 39*b*).

FIG. 40 shows the protective effect against USA300 MRSA infection in each of a group (group 2, G2) pretreated by intravenous injection of purified antibodies against the four antigens discovered in the present invention, and a rabbit group obtained by pretreating group 2 (G2) with vancomycin, and shows the survival rate of each group (FIG. 40*a*) and the results of observing the kidneys of group 2 and group 4 rabbits (FIG. 40*b*).

FIG. 41 shows the protective effect against USA300 MRSA infection in each of a group (group 2, G2) obtained by infecting rabbits, immunized with four antigens three times, with the USA300 MRSA strain, a group (group 4, G4) obtained by intramuscular injection of teicoplanin into G2 3 hours after USA300 MRSA infection, a group (group 3, G3) treated with teicoplanin alone, and a group (group 1, G1) treated with saline alone. Specifically, FIG. 41 shows the results of ELISA performed to measure the antibody titer against each antigen after immunization (FIG. 41*a*), the survival rate of each group (FIG. 41*b*), the results of quantifying residual bacteria (CFU) in each kidney (FIG. 41*c*), and the results of observing the kidneys of the rabbits of each group (FIG. 41*d*).

MODE FOR INVENTION

Hereinafter, the present invention will be described in more detail with reference to examples. These examples are only for explaining the present invention in more detail, and it will be apparent to those skilled in the art that the scope of the present invention according to the subject matter of the present invention is not limited by these examples.

EXAMPLES

Example 1: Selection of *Staphylococcus aureus* Toxins

Experimental Methods

Ethics Statement

Human blood was obtained from four healthy volunteers. The IRB of Pusan National University approved this study protocol (PNU IRB/2019_59_BR). Written informed consents were provided by study participants.

Bacteria

*S. aureus* strain USA300 LAC strain was grown to mid-logarithmic phase ($OD_{600}$ 0.8-1.5) in tryptic soy broth (TSB) at 37° C. with shaking. *Escherichia coli* DH5α strains were grown at 37° C. with shaking in Luria Broth (LB) supplemented with 10 μg/ml of kanamycin (Km).

Purification of Recombinant BCL Toxins and Toxoids Production

Polyhistidine-tagged recombinent toxins were cloned and expressed using an *E. coil* expression system. LukS-PV, LukF-PV, LukE, LukD, HlgA, HlgB, HlgC, LukAB, Hla, $Hla_{H35L}$, $LUkS_{T244A}$-PV, $LUkA_{E323A}B$ of target genes were amplified by PCR from USA300 genome sequences using Q5 High Fidelity DNA polymerase (Thermo Fisher Scientific). The PCR product was cloned into pET28a-vector, resulting in expression of proteins with an N-terminal or C-terminal 6×His-tag. For purification of LukAB and $LukA_{E323A}B$, the present inventors inserted 6×His-tag into both N- and C-terminal regions. Obtained clones were sequenced to verify the correct construction. The recombinant proteins were expressed in BL21 pLysS *E. coli* using 0.2 mM isopropy-lβ-D-1-thiogalactopyranoside (IPTG, 0.2 mM concentration) for induction. The expressed proteins were purified using Ni-Sepharose 6 fast flow resin (GE healthcare, 17-5318-01, 5 ml) with loading buffer (20 mM sodium phosphate, 0.1% triton X-100, 150 mM NaCl, 5 mM imidazole, pH 7.4), washing buffer (20 mM sodium phosphate, 150 mM NaCl, 5 mM imidazole, pH 7.4) and elution buffer (20 mM sodium phosphate, 150 mM NaCl, 500 mM imidazole, pH 7.4). Primer sequences used in Example 1 are shown in Table 1 below.

TABLE 1

| SEQ ID NO | Primer | Sequence |
|---|---|---|
| | C-term His tag | |
| SEQ ID NO: 1 | Vector-pET28a-F | CATGGTATATCTCCTTCTTAAAGTTAAAC |
| SEQ ID NO: 2 | Vector-pET28a-R | CACCACCACCACCACCACTGAGATC |
| SEQ ID NO: 3 | pET28a-6 His-LukS-R | GTGGTGGTGGTCGTCATTATGTCCTTTCACTTTAATTTCATGAGTTTTC |
| SEQ ID NO: 4 | pET28a-6 His-LukS-F | CTTTAAGAAGGAGATATACCATCGATAACAATATTGAGAATATTCGTGATGGCG |
| SEQ ID NO: 5 | pET28a-6 His-$LukS_{T244A}$-R | CATGCTATATCTCCTTCTTAAAGTTAAAC |
| SEQ ID NO: 6 | pET28a-6 His-$LukS_{T244A}$-F | CTATTGCCATACTGTGCTGTTCTTCTACTAGCATGAG |
| SEQ ID NO: 7 | pET28a-6 His-LukF-R | GTGGTCGTGGTGGTGGCTCATAGGATTTTTTTCCTTAGATTGAG |
| SEQ ID NO: 8 | pET28a-6 His-LukF-F | CTTTAAGAAGGAGATATACCATGGCTCAACATATCACACCTGTAAGTGAG |
| SEQ ID NO: 9 | pET28a-6 His-HlgA-R | GTGGTGGTGGTGGTGCTTAGGTGTGATGCTTTTAATTTTTACTTC |
| SEQ ID NO: 10 | pET28a-6 His-HlgA-F | CTTTAAGAAGGAGATATACCATGGAAAATAAGATAGAAGATATCCGCCAAGGTGC |
| SEQ ID NO: 11 | pET28a-6 His-HlgC-R | GTGGTGGTGGTGGTGATTCTGTCCTTTCACCTTGATTTCATG |
| SEQ ID NO: 12 | pET28a-6 His-HlgC-F | CTTTAAGAAGGADATATACCATGCTAACCATACTGAAGACATCGGTAAACG |
| SEQ ID NO: 13 | pET28a-6 His-LukE-R | GTGGTGGTGGTGGTGTTATGTCCTTTCACTTTAATTTCGTGTGTTTTC |
| SEQ ID NO: 14 | pET28a-6 His-LukE-F | CTTTAAGAAGGAGATATACCATGAATACTAATATTGAAAATATTGCT-GATGGTCCTG |
| SEQ ID NO: 15 | pET28a-6 His-LukD-R | GTGCTGGTCGTGGTGTACTCCAGGATTAGTTTCTTTAGAATCCG |
| SEQ ID NO: 16 | pET28a-6 His-LukD-F | CTTTAAGAAGGAGATATACCATGGCTCAACATATCACACCTGTAAGCG |
| SEQ ID NO: 17 | pET28a-6 His-Hla-R | CAGTGGTGCTCGTCGTCGTGATTTGTCATTTCTTCTTTTTCCCAAT |
| SEQ ID NO: 18 | pET28a-6 His-Hla-F | AAGAAGGAGATATACCATGGCAGATTCTGATATTAATATTAAAACCCG |
| SEQ ID NO: 19 | pET28a-6 His-$Hla_{H35L}$-R | GAAGAACCATCTATCCATTTATGTTTAGTATTGGTAC |
| SEQ ID NO: 20 | pET28a-6 His-$Hla_{H35L}$-F | GATAAAGAAAATGGCATGCTCAAAAAAGTATTTTATAGTTTTATCG |
| | N-term His tag | |
| SEQ ID NO: 21 | Vector-pET28a-R | GTGATGATGATGATGATGGCTG |
| SEQ ID NO: 22 | Vector-pET28a-F | CACCACCACCACCACCACTGAGATC |
| SEQ ID NO: 23 | pET28a-6 His-HlgB-R | TTGTTAGCAGCCGGATCTCATTTATTGTTTTCAGTTTCTTTTGTATCTAACAAT |
| SEQ ID NO: 24 | pET28a-6 His-HlgB-F | ATGGGCAGCAGCCATCATCATCATCATCACGAAGGTAAAATAACACC |
| | N-term and C-term His tag | |
| SEQ ID NO: 25 | pET28a-6 His-LukA-R | ATGGCCAGCAGCCATCATCATCATCATCACAATTCAGCTCATAAAGACTCTCAA-GAC |
| SEQ ID NO: 26 | pET28a-6 His-LukA-F | TAGTAATCCGCCCTTTCAATATTATCCTTCTTTATAAGGTTTATTCTCATCAG |
| SEQ ID NO: 27 | pET28a-6 His-LukB-R | CAGTGGTGGTGGTGGTGGTGTTATTTCTTTTCATTATCATTAAGTACTTTTACAAA |
| SEQ ID NO: 28 | pET28a-6 His-LukB-F | TATTGAAAGGGCGCATTACTAATGAAGATTAATTCTGAAATCAAACAAGTTTC |
| SEQ ID NO: 29 | pET28a-6 His-LukAE323A-F | TAGTAATCCCCCCTTTCAATATTATCCTCCTTTATAAGCTTTATTCTCATCAG |
| SEQ ID NO: 30 | pET28a-6 His-LukAE323A-R | ATCGGCAGCAGCCATCATCATCATCATCACAATTCACCTCATAAAGACTCTCAA-GAC |

Rabbit Immunization for Obtaining Toxin Antibody

500 μg of purified single components of six *S. aureus* toxins and their toxoid proteins dissolved in 500 μl of PBS were mixed with 500 μl of Complete Freund's Adjuvant (Sigma-Aldrich) and mixed to make emulsions. Each emulsion was injected subcutaneously into a rabbit, and two weeks later, the same amounts of antigens were mixed with 500 μl of Incomplete Freund's Adjuvant (Sigma-Aldrich) and injected via subcutaneous route. Two week later, 500 μl microliters of blood were taken from the rabbit ear vein and the generation of IgGs of each antigen was confirmed via Western blot analysis. If antibodies were produced, rabbit whole bloods were collected and sera were obtained therefrom. Rabbit sera were stored at −80° C. until use.

Coupling of Purified Proteins to CNBr-Activated Sepharose Beads

The coupling between recombinant single component toxins and CNBr-activated Sepharose beads was performed according to the method provided by the manufacture (GE Health Care). Briefly, one gram of CNBr-activated Sepharose beads were washed 3 times with coupling buffer (3 ml/one time, 0.1 M $NaHCO_3$, pH 8.5). Five mg of recombinant proteins dissolved in 1 ml of coupling buffer were added to washed CNBr-activated beads that were then suspended in 4 ml of coupling buffer. After incubation for 2 hours at RT, beads were washed 3 times with coupling buffer. Then, beads were incubated with 4 ml of 1M ethanolamine (pH 8.0) for 4 hours at RT. After incubation, beads were washed with 0.1M sodium phosphate (pH 7.4) until showing no UV absorbance at 280 nm and stored at 4° C. until use.

Purification of Rabbit Anti-Single Component Recognizing IgGs from Rabbit Sera

After antigen-coupled Sepharose column was equilibrated with washing buffer (0.1 M sodium phosphate containing 0.1 M NaCl, pH 7.4), antigen-immunized rabbit sera (1 ml, 60 mg of protein) were loaded onto the column which was then intensively washed with washing buffer, and then the bound IgGs were eluted with elution buffer (0.15 M glycine/HCl, pH 2.2). The collected IgGs were neutralized with neutralizing buffer (1 M Tris/HCl buffer, pH 9.0). After buffer changing with PBS, the collected IgGs were analyzed by SDS-PAGE under reducing and non-reducing conditions.

Dot Blot Immunoassay

The prepared PVDF-membrane strips (Immobilion P, 0.22 μm pore size, Millipore) were activated in methanol for 30 seconds. Then, strips were washed with $H_2O$ for 5 min with gentle shaking. After washing, one μg of recombinant single component toxin (LukS-PV, LukF-PV, HlgA, HlgB, HlgC, LukE, LukD and LukAB) was loaded onto strips. Each single component and LukAB proteins (each 1 μg) and, *S. aureus* $FnbpA^{N2N3}$ (N2-N3 domain of fibronection-binding protein) as a negative protein were spotted. After drying strips for 2 hours at RT, spotted proteins were fixed with methanol for 15 sec and then washed with $H_2O$ 3 times and with 1×TBS (50 mM Tris-HCl, pH 7.5, 150 mM NaCl) 3 times. Then, strips were blocked with 5% skim milk for 2 hours and then incubated with single component-toxin immunized IgGs (1:1600 dilution with 5% skim milk) for 1 hour at 4° C. After incubating, membranes were washed 3 times with 1×TBST (50 mM Tris-HCl, pH 7.5, 150 mM NaCl, 0.2% Tween 20). Mouse anti-Rabbit IgG-HRP (1:3000 dilution, Santacruz) were added to membranes and incubated for 1 hour at 4° C. Then, membranes were washed 3 times with 1×TBST and then developed using Pico EPD Western blot detection kit [ELPIS-Biotech].

Isolation of Human PMNs

The polymorphonuclear cells (PMNs) were isolated using collected whole blood (2 ml) and Polymorphprep™ (2 ml, Axis-shield,) in 5 ml round-bottom tube at RT. The samples were centrifuged at 450×g for 30 min at 20° C. After removing the supernatant, two leucocyte bands containing mononuclear cells of upper band and PMNs of lower band were obtained. Then, collected PMNs were washed 2 times with RPMI (Gibco), and then collected after centrifugation at 400×g for 10 min at 20° C. The collected cells were gently resuspended in 2 ml RPMI+0.02% HSA buffer and then counted with hematocytometer (EKDS, Tokyo).

Isolation of Rabbit RBCs

One ml of rabbit blood was collected into hirudin-coated Vacutainer tubes (BD, Becton Drive) to prevent coagulation via ear vein. Then, tubes were centrifuged at 9,100×g for 10 min at 4° C. and red blood cells (RBCs) were obtained. RBCs were washed 2 times with PBS containing 0.02% BSA and then collected by centrifugation at 500×g for 5 min at 4° C. Then, stock RBC was prepared by dilution to 2% RBCs with PBS containing 0.02% BSA.

Cytolytic and Hemolytic Assays

To evaluate the viability of primary human PMNs in the presence or absence of *S. aureus* BCLs or Hla in vitro, PMNs were seeded at $2\times10^6$ cells per well in 48 well cell culture plate (SPL) and mixed with the same amounts of S- and F-components (each 65 ng) except for LukAB (130 ng). This mixture was incubated for 1 hour at 37° C. with 5% $CO_2$ conditions. Then, survived cells were counted with hematocytometer.

Toxin-Mediated RBCs Hemolysis Assay

To perform the hemolytic assay of rabbit RBCs in the presence or absence of $Hla_{WT}$ toxin in vitro, 2% RBCs were seeded at 100 μl per well in 96 well cell culture plate. Then, 0.25 μg of purified recombinant $Hla_{WT}$ toxin was added to the 96 well plate and incubated for 1 hour at 37° C. with 5% $CO_2$ conditions. After incubation, the supernatant was collected by centrifugation for 5 min at 500×g. Then, the absorbance at 405 nm was measured using spectrophotometer (Eppendorf BioPhotomter).

Western Blot Analysis

Purified BCL toxins, Hla and toxoids were subjected to 15% SDS-PAGE gel electrophoresis and then electro-transferred onto 0.45 μm PVDF membrane using transfer buffer (192 mM Glycin, 25 mM Tris, 0.02% SDS, 20% MtOH) with 100 V, 400 mA for 75 min at 4° C. Then, the membrane was blocked with 5% skim milk for 1 hour. The membrane was incubated with immunized rabbit sera (1:6000) and blocked with 5% skim milk for 1 hour at 4° C. After incubating, the membrane was washed 3 times with 1×TBST (50 mM Tris-HCl, pH 7.5, 150 mM NaCl, 0.2% Tween 20). Mouse anti-Rabbit IgG-HRP (Santacruz) were added and incubated for 1 hour at 4° C. Then, the membrane was washed 3 times with 1×TBST and then developed using Pico EPD Western blot detection kit [ELPIS-Biotech].

Experimental Results

Purified five recombinant *S. aureus* bi-component leukocidins (BCLs) and Hla hydrolyzed human PMNs and RBC, respectively, but not their toxoids.

Figures 1A, 1B, 1C, 1D, 1E, 1F:
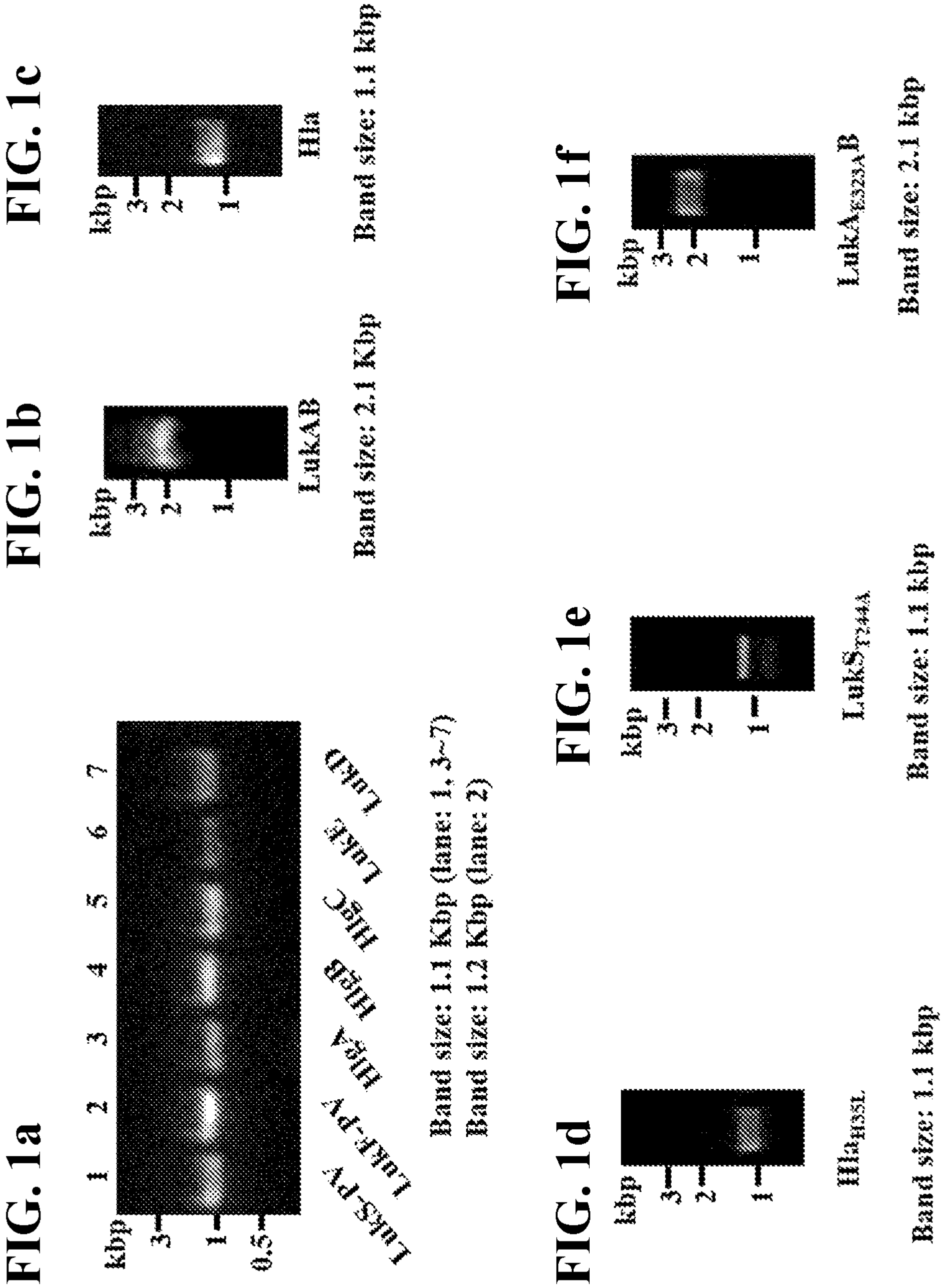
FIGS. 1*a* to 1*f* show agarose electrophoresis patterns of cloned wild-type and toxoids gene products of BCLs, Hla and three toxoids. Expected gene products were obtained.

To study the relationships between *S. aureus* toxins and toxin-mediated host cell cytotoxicity, the present inventors firstly cloned (FIGS. 1A to 1C) and expressed five BCLs and Hla in *Escherichia coli* system. To purify these six expressed recombinant toxins, $His_{6x}$-tags were inserted on the N-terminal or C-terminal sites of targeted toxins (FIG. 2). As shown in FIG. 3, recombinant proteins of four S-components and three F-components of *S. aureus* BCLs were purified to homogeneity, but $LukAB_{WT}$ was cloned and purified as a dimer form since monomer forms of LukAB showed so low yield of expression (FIG. 3*a*). In addition, recombinant $Hla_{WT}$ and $Hla_{H35L}$, $LukS_{T244A}$, and $LukA_{E323A}B$ toxoid were also purified to homogeneity (FIG. 3*b*). Hla toxoid ($Hla_{H35L}$) with a single active amino acid substitution cannot form cytolytic pores since His-35 residue was mutated to Leu, but it was known to retain the ability to bind its receptor on the host target cells (Menzies B E et al., 1994. *Infect Immun* 62:1843-7; Menzies B E et al., 1996. *Infect Immun* 64:1839-41). Since the mutation of Thr-244 residue to Ala of LukS-PV ($LukS_{T244A}$-PV) was known to lead dramatically reduced binding affinities for both human leukocytes and undifferentiated U937 cells expressing the C5a receptor (Laventie B J et al., 2014. *PLoS One* 9:e92094), the present inventors have cloned and purified $LukS_{T244A}$ mutant. Also, $LukA_{E323A}B$ was constructed and used since the Glu-323 residue of LukA was reported to be critical for LukAB cytotoxicity and required for the interaction between LukAB and its cellular target CD11b (DuMont A L et al., 2014. *Infect Immun* 82:1268-76). To confirm whether wild type leukocidins and toxoids can show expected cytolytic activities against human PMNs, the present inventors mixed the same amounts of S component and F-components, resulting in productions of wild-type leukocidins, such as LukSF-PV, LukED, HlgAB, HlgCB, LukAB and of inactive leukocidins, such as $LukS_{T244A}$-PV and $LukA_{E323A}B$.

After S-, F-components of BCLs, Hla and their toxoid proteins were separately expressed and purified, their toxicities were examined by the mixing of each cognate component using human PMNs and RBCs. Upon mixing of the same amounts of S- and F-components (each 0.25 μg/ml) except for LukAB (0.5 μg/ml), all five cognate BCLs, such as LukSF-PV, LukED, LukAB, HlgAB, HlgCB, completely hydrolyzed human polymorphonuclear leukocytes (PMNs, $2\times10^6$ cells) within 30 min, but, the mixture of $LukS_{T244A}$-PV toxoid (0.25 μg/ml) and LukF-PV (0.25 μg/ml) did not show any toxic activity against human PMNs (FIG. 3*c*). Also, $LukA_{E323A}B$ dimer toxoid (0.5 μg/ml) did not show any cytotoxic activity against human PMNs (FIG. 3*c*). In addition, purified $Hla_{WT}$ (2.5 μg/ml) hemolyzed 2% rabbit RBCs within 30 min, but its inactive $Hla_{H35L}$ toxoid did not show any hemolytic activity against rabbit RBCs (FIG. 3*d*). Taken together, these data indicate that purified *S. aureus* BCLs and their toxoid proteins were correctively cloned and purified to homogeneity.

Single S- or F-Component Anti-Rabbit IgGs Have Cross-Reactivity Against Other BCL Components Since *S. aureus* BCLs have high sequence homologies between S-S or F-F single components, single component-immunized rabbit antibodies are expected to bind another single component of *S. aureus* BCL toxins. However, because their recognition patterns by single component-IgG will be important to screen BCL-antibodies that are capable to broadly neutralizing five BCL-mediated cytotoxicity, the present inventors obtained rabbit polyclonal antibodies against eight different single components through affinity purification using single component-conjugated Sepharose columns (FIG. 4). Also, because our recombinant toxins and toxoids of the present invention harbor 6×His-tag on the N- or C-terminal region, His-tag-derived IgGs were removed using 6×His-tagged *S. aureus* fibronectin binding protein A ($FnbpA^{N2-N3}$)-conjugated Sepharose columns (data not shown). Using these purified rabbit single-component-recognizing IgGs, the present inventors examined the cross-reactivity between each BCL single-component and purified BCL-recognizing IgGs by dot-blot immunoassay (FIG. 5). All IgGs used did not bind to $FnbpA^{N2-N3}$, which was used as a negative control protein. Anti-LukS-PV-IgG recognized all four S-components, such as LukS-PV>HlgC>HlgA and >LukE, but not all three F component and LukAB (column a in FIG. 5, red and green boxes indicate cognate and non-cognate antigens, respectively). Anti-LukE-IgG also recognized four S-components, such as bound LukE>LukS>HlgC>HlgA (column fin FIG. 5). Anti-HlgA-IgG recognized Hlg>HlgC>LukF (column c). Anti-HlgC-IgG recognized HlgC≥LukS>HlgA (column e in FIG. 5). In case of F-component-IgG, anti-LukF-PV-IgG has shown given positive signals against LukF>LukD (column b in FIG. 5). Anti-HlgB-IgG recognized three F-components, such as LukF-PV>HlgB>LukD (column d in FIG. 5). Anti-LukD-IgG showed binding ability against LukD>LukF-PV (column g in FIG. 5). As expected, LukAB-IgG only showed binding specificity against its cognate antigen LukAB antigen (column h in FIG. 5). Taken together, these results indicated that LukS-PV and LukE-IgGs showed the broadest binding abilities against four BCL S-components. However, interestingly, although anti-HlgA-IgG is S-component-recognizing IgGs, this IgGs also recognized LukF-PV F-component (columns c and g in FIG. 5). As for anti-HlgB-IgG, it recognized three F-components, HlgB, LukD and LukF, but other two F-components (LukF-PV and LukD) only recognized their cognate F-components and one more non-cognate F-components. Taken together, these results showed that BCL S- and F-components showed the differential recognition patterns against their cognate and non-cognate antigens.

Figure 6A:
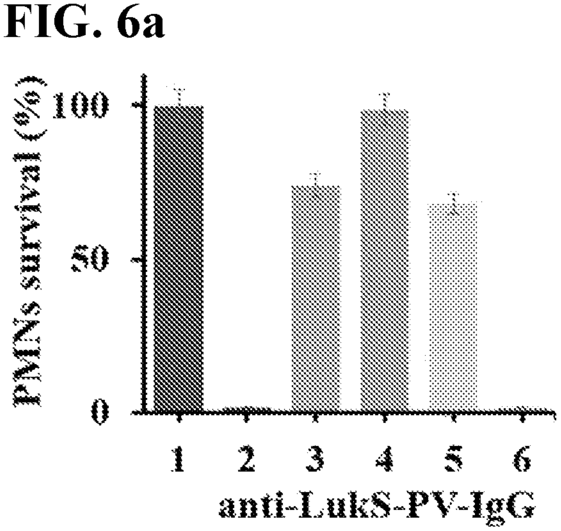
FIGS. 6*a* to 6*d* show human PMN survival rates upon co-incubation of PMNs ($2\times10^6$ cells) with the mixture of cognate S-component (0.25 μg/ml) and F-component (0.25 μg/ml) of BCLs in the presence of each purified anti-LukS-PV-IgG (FIG. 6*a*), anti-HlgA-IgG (FIG. 6*b*), anti-HlgC-IgG (FIG. 6*c*) and anti-LukE-IgG (FIG. 6*d*). Column 1, no toxin (green); column 2, HlgA+HlgB (brown); column 3, LukE+LukD (yellowish green); column 4, LukS-PV+LukF-PV (blue); column 5, HlgC+HlgB (yellow); column 6, LukAB (orange).
Figure 6B:
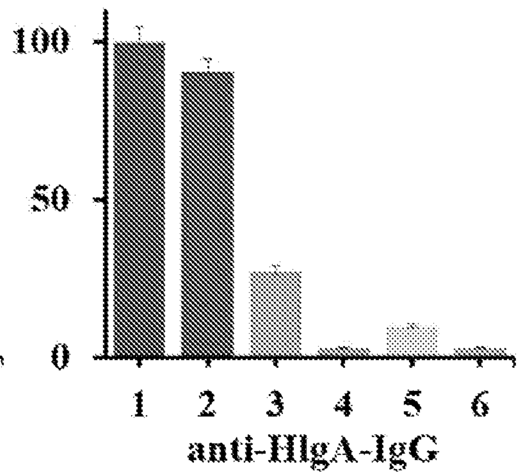
Figure 6C:
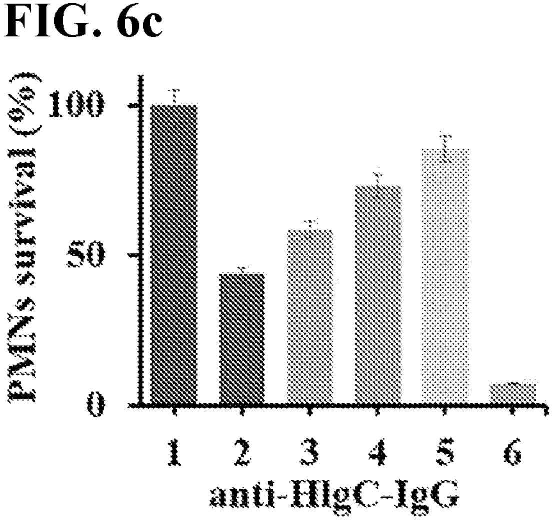
Figure 6D:
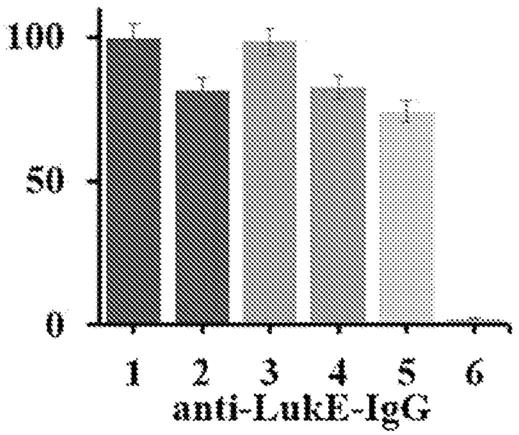

Four Anti-S-Component-IgGs Showed Partial Neutralizing Effects Against Four BCL-Mediated PMNs Cytolytic Activity The present inventors examined how much the BCL-mediated neutrophil cytolytic activity will be neutralized by addition of anti-S- or F-component-IgG in vitro. When human PMNs were co-incubated with each BCL and anti-LukS-PV-IgG (FIG. 6*a*), anti-LukS-PV-IgGs inhibited LukSF-PV-(98.5±0.5%), LukED-(74±1%), and HlgCB-(68.1±1%)-mediated PMN cytolytic activity, but HlgAB- and LukAB-derived PMN cytolytic activity were not completely neutralized by anti-LukS-PV-IgG. In contrast, anti-HlgA-IgG only neutralized HlgAB-derived (90.3±3%) and LukED-mediated PMN lysis (27.5±4%), but LukSF-PV, HlgCB and LukAB-mediated PMN cytotoxicity was almost not blocked (FIG. 6*b*). Anti-HlgC-IgG inhibited HlgAB-(43.9±0.5%), LukED-(58.5±1%), and LukSF-PV-(73.2±0.5%), HlgCB-(85.4±1%) and LukAB-(0%)-mediated PMN lysis (FIG. 6*c*). As expected, anti-LukE-IgG inhibited four-BCL-mediated PMN lysis by more 70%, but did not completely inhibit LukAB-derived lysis (FIG. 6*d*). In dot-blot experiment (FIG. 5), anti-LukE-IgG strongly recognized LukE>LukS-PV, but HlgC>HlgA weakly. However, four-BCL-mediated PMN lysis was blocked by 75±3% by anti-LukE-IgG, suggesting that there are some differences between dot blot immunoassay and neutralization abilities of single S-component IgGs in BCL-mediated human PMN cytolytic activities.

Three Anti-F-Component-IgGs Neutralized HlgCB-Mediated PMN Cytolytic Activity

Figure 7A:
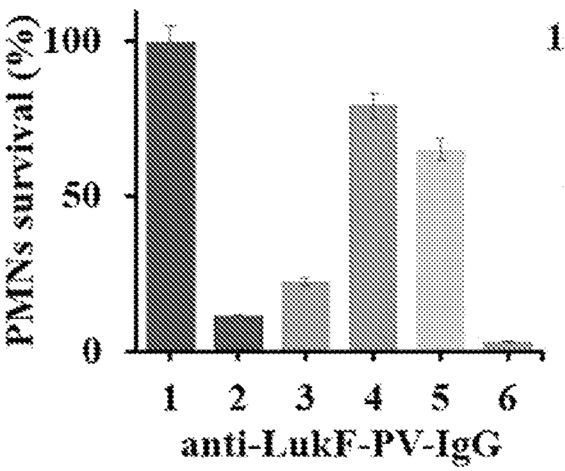
FIGS. 7*a* to 7*c* show human PMN survival rates upon co-incubation of PMNs ($2\times10^6$ cells) with the mixture of cognate S-component (0.25 μg/ml) and F-component (0.25 μg/ml) of BCLs in the presence of each purified anti-LukF-PV-IgG (FIG. 7*a*), anti-HlgB-IgG (FIG. 7*b*), and anti-LukD-IgG (FIG. 7*c*). Column 1, no toxin (green); column 2, HlgA+HlgB (brown); column 3, LukE+LukD (yellowish green); column 4, LukS-PV+LukF-PV (blue); column 5, HlgC+HlgB (yellow); column 6, LukAB (orange).
Figure 7B:
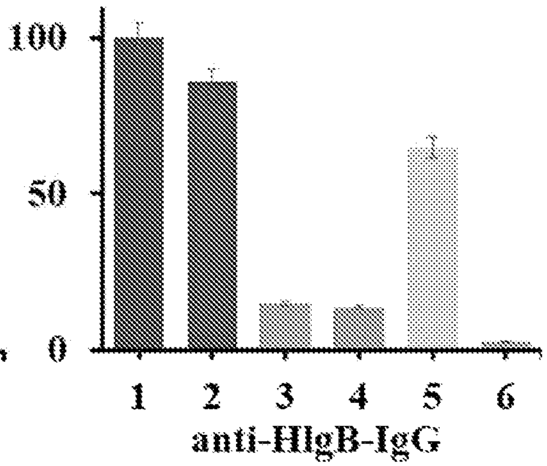
Figure 7C:
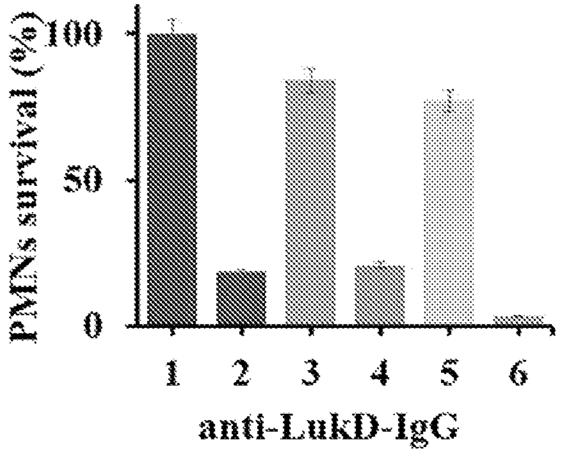

As shown in FIG. 7, when anti-F-component-IgGs were co-incubated with human PMNs and BCLs, anti-LukF-PV IgG blocked LukSF-PV-mediated PMN lysis activity (85±0.5%) and HlgCB-derived PMN lysis activity (74±1%), but HlgAB, LukED and LukAB-mediated PMNs cytolytic activities were almost not neutralized by anti-LukF-IgG (FIG. 7*a*). Also, anti-HlgB-IgG also inhibited HlgAB-mediated PMN lytic activity (85.8±1%) and HlgCB-mediated PMN lytic activity (65±0.5%), but poorly inhibited LukED-(10±0.5%), LukSF-PV-(10±1%), and LukAB-(2±1%) mediated lytic activities (FIG. 7*b*). In case of anti-LukD-IgGs, it also neutralized LukED-(84±4%) and HlgCB (77±1%)-mediated PMN lysis activities, but, HlgAB-(18.4±3%), LukSF-(20.8±0.2%) and LukAB (3±0.1%)-mediated lytic activities were poorly neutralized by LukD-IgGs (FIG. 7*c*). Taken together, although in the dot blot immunoassay (FIG. 5), two F-component-IgGs, such as anti-LukF-IgG and anti-LukD-IgG, did not recognize HlgB, these two F-components IgGs commonly neutralized HlgCB-mediated PMN lytic activity, indicating that these two F-component-IgGs may recognize a specific sequence of non-cognate HlgB, leading to inhibition of oligomerization of HlgCB BCL.

Figure 8A:
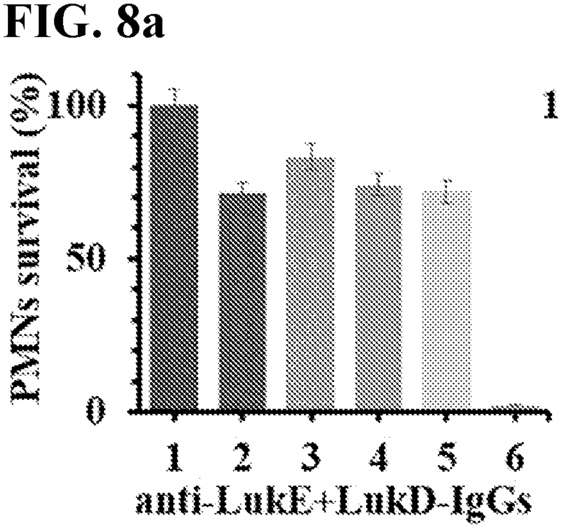
FIGS. 8*a* to 8*e* show human PMN survival rates upon co-incubation of PMNs ($2\times10^6$ cells) with the mixture of cognate S-component (0.25 μg/ml) and F-component (0.25 μg/ml) of BCLs in the presence of each purified anti-LukE+LukD-IgG (FIG. 8*a*), anti-HlgA+HlgB-IgG (FIG. 8*b*), anti-HlgC+HlgB-IgG (FIG. 8*c*), anti-LukS+LukF-IgG (FIG. 8*d*), and anti-LukAB-IgG (FIG. 8*e*). Column 1, no toxin (green); column 2, HlgA+HlgB (brown); column 3, LukE+LukD (yellowish green); column 4, LukS-PV+LukF-PV (blue); column 5, HlgC+HlgB (yellow); column 6, LukAB (orange).
Figure 8B:
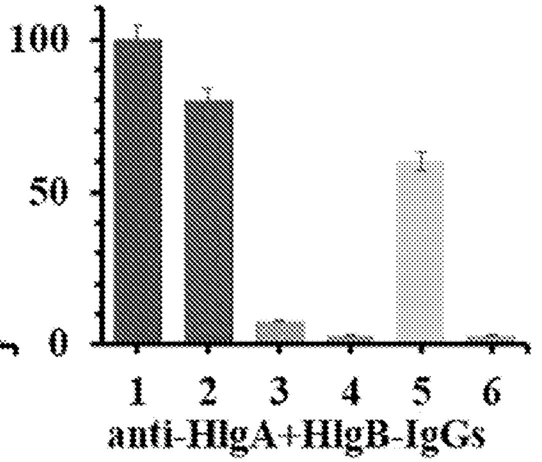

Different Combination of Anti-BCL-Component-IgG Showed Diverse Neutralization Abilities Against BCL-Mediated Cytotoxicity The present inventors hypothesized that if we can screen minimal numbers of BCL's anti-S- or anti-F-component IgGs that can neutralize five-BCL-mediated cytotoxicity broadly, they will be useful information for designing a novel therapeutic tool against *S. aureus* infection. It was reported that LukSF-PV and HlgCB commonly recognize C5aR1 and C5aR2 receptors expressed on the host cells (7). But, LukED utilizes CCR5, CXCR1, and CXCR2 (Spaan A N et al., 2013. *Cell Host Microbe* 13:584-594). However, LukED recognizes CCR5, CXCR1, and CXCR2 (Alonzo F, et al., 2013. *Nature* 493:51-5), and HlgAB and LukED are known to share CXCR1 and CXCR2 as receptors but can also utilize CCR2 (Spaan A N et al., 2017. *Nat Rev Microbiol* 15:435-447), whereas LukAB binds to CD11b (DuMont A L et al., 2014. *Infect Immun* 82:1268-76). Based on the experimental results in FIGS. 6*a* to 7*c*, the present inventors further examined which different combination of anti-single-component-IgG or anti-toxoid-IgGs can efficiently neutralize cytotoxicities derived from five BCLs. As shown in FIGS. 8*a* to 8*e*, when the mixture of anti-LukE-IgG (5 μg) and anti-LukD-IgG (5 μg) was co-incubated with human PMNs and five BCLs for 60 min, four BCL-mediated PMNs cytotoxicities, except for LukAB, were neutralized more than 70% by these two IgGs (FIG. 8*a*). However. the mixture of anti-HlgA- and HlgB-IgGs only neutralized HlgAB-(79.8±5%) and HlgCB-(60±1%)-mediated cytotoxicity (FIG. 8*b*), but this IgG mixture showed no inhibitory effects against LukED, LukSF-PV and LukAB. These results showed that, although HlgAB and LukED are reported to bind CXCR1, CXCR2 and CCR2 as receptors, the IgG mixture of HlgA and HlgB almost did not neutralize LukED-mediated cytotoxicity. Unexpectedly, the anti-HlgA-IgG and anti-HlgB-IgG mixture inhibited C5aR-recognizing HlgCB cytolytic activity.

Figure 8C:
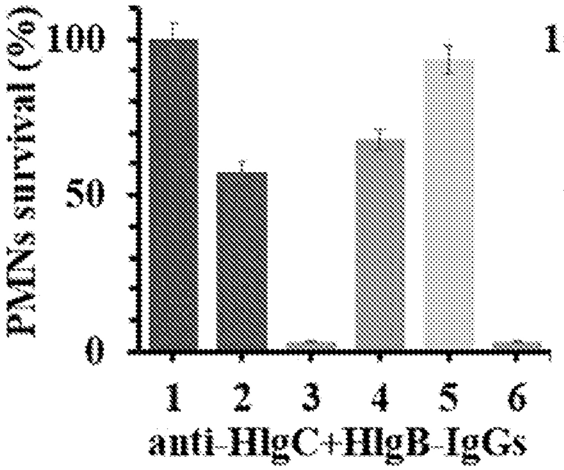
Figure 8D:
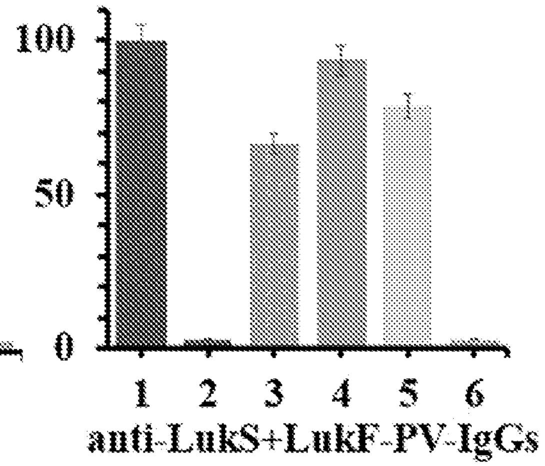
Figure 8E:
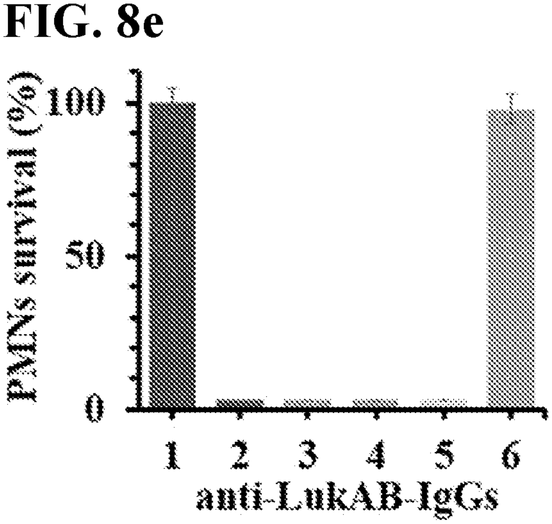
Figure 9A:
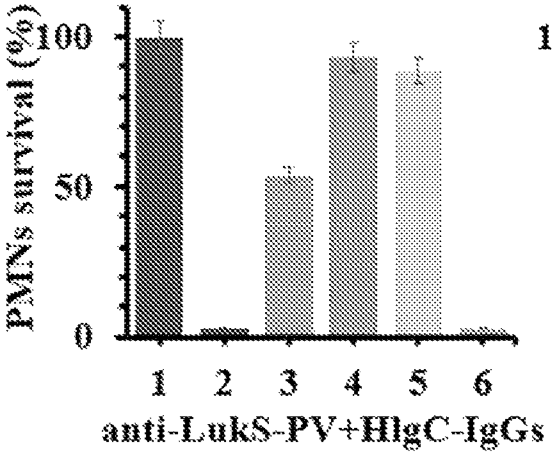
FIGS. 9*a* to 9*f* show human PMN survival rates upon co-incubation of PMNs ($2\times10^6$ cells) with the mixture of cognate S-component (0.25 μg/ml) and F-component (0.25 μg/ml) of BCLs in the presence of each purified anti-LukS-PV+HlgC-IgGs (FIG. 9*a*), anti-LukS-PV+HlgA-IgGs (FIG. 9*b*), anti-LukS-PV+LukE-IgGs (FIG. 9*c*), anti-HlgA+LukE-IgGs (FIG. 9*d*), anti-HlgA+HlgC-IgGs (FIG. 9*e*), and anti-HlgC+LukE-IgGs (FIG. 9*f*). Column 1, no toxin (green); column 2, HlgA+HlgB (brown); column 3, LukE+LukD (yellowish green); column 4, LukS-PV+LukF-PV (blue); column 5, HlgC+HlgB (yellow); column 6, LukAB (orange).
Figure 9B:
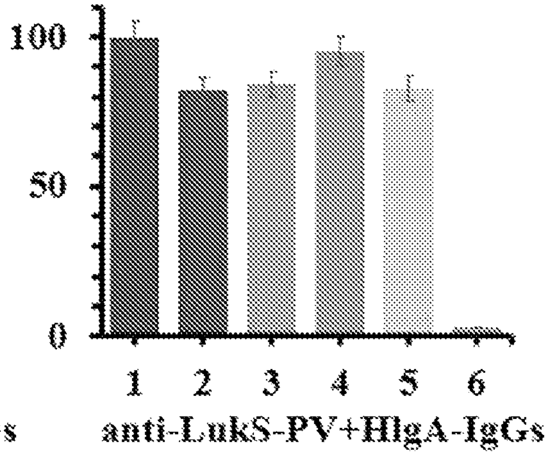
Figure 9C:
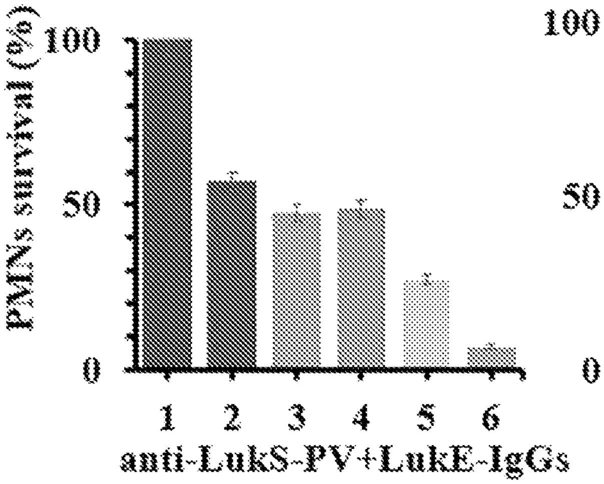
Figure 9D:
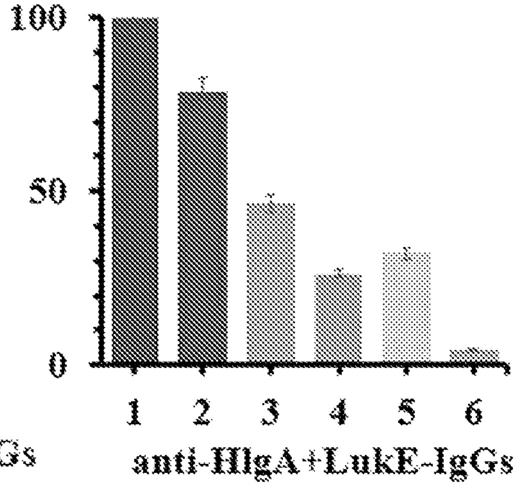
Figure 9E:
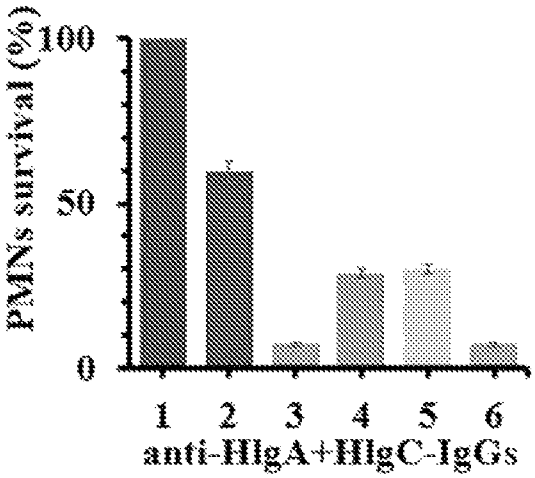
Figure 9F:
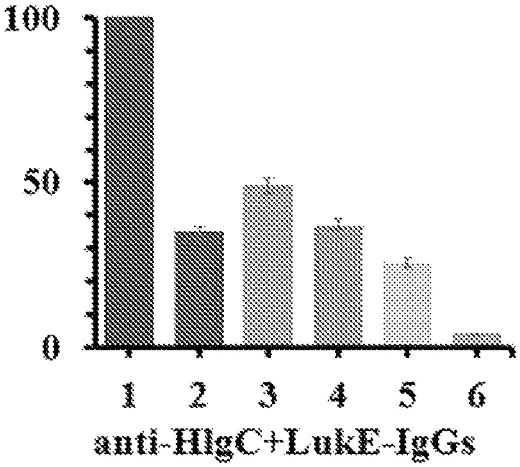

The mixture of anti-HlgC-IgG and anti-HlgB-IgG neutralized lytic activities of HlgCB (93.4±0.5%)>LukSF-PV (70±1%)>HlgAB (57.8±1%), indicating that this C5aR-recognizing BCL-rabbit polyclonal IgG mixture also inhibited cytotoxicity of chemokine-receptor-recognizing HlgAB (FIG. 8*c*). However, the mixture of anti-LukS-PV-IgG and anti-LukF-PV-IgG neutralized LukSF-PV-(93.5±1%) and HlgCB-(78.7±1%) mediated lytic activity and also inhibited LukED (68±0.5%)-derived PMN lytic activity (FIG. 8*d*). Together, as expected, anti-LukAB-IgG only neutralized LukAB cytotoxicity, but not 4 BCL-mediated toxic effects (FIG. 8*e*). These results demonstrated that different combination of anti-BCL-IgGs showed diverse neutralization capacities against four-BCL-mediated cytotoxicity, but completely not to LukAB toxic effects.

Among Anti-S-Component-IgG Combination, Mixture of Anti-LukS-PV- And Anti-Hlga-IgGs Showed the Highest Level of Neutralization Activities Against BCL-Mediated Cytotoxicity Next, the present inventors have examined the neutralization abilities by the combination of cognate BCL S-IgGs against 5 BCL-mediated PMNs cytolytic activities. To this end, the present inventors estimated neutralization abilities by the combination of six different anti-S-component-IgGs against five BCL-mediated cytolytic activities (FIGS. 9*a* to 9*f*). When each possible six combination of anti-S-component-IgGs was incubated with human PMNs and five different BCLs, PMNs survival rates were calculated. PMNs survival rates were as follows: LukS-PV+HlgC (average survival rate 59.7%, FIG. 9*a*), LukS-PV+HlgA (85.8%, FIG. 9*b*), LukS-PV+LukE (45.2%, FIG. 9*c*), HlgA+LukE (45.9%, FIG. 9*d*), HlgA+HlgC (31.3%, FIG. 9*e*), and HlgC+LukE (36.8%, FIG. 9*f*). Among them, anti-LukS-PV and anti-HlgA-IgGs mixture most efficiently inhibited four BCL-mediated cytolytic activities (FIG. 9*b*) compared to five other combinations. These results indicated that the mixture of two anti-S-component-IgGs is able to neutralize four BCL-toxic effects, but not LukAB.

Figure 10A:
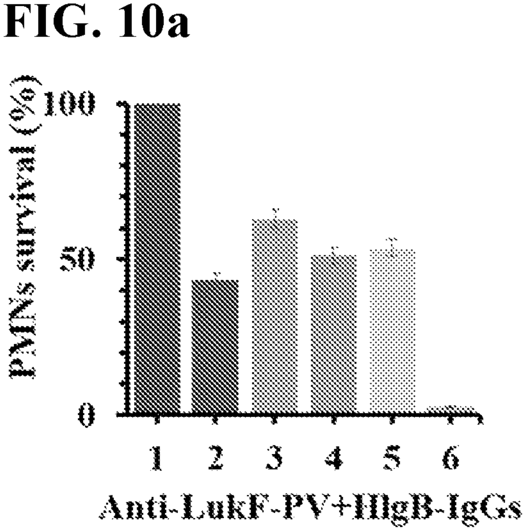
-FIGS. 10*a* to 10*d* show human PMN survival rates upon co-incubation of PMNs ($2\times10^6$ cells) with the mixture of cognate S-component (0.25 μg/ml) and F-component (0.25 μg/ml) of BCLs in the presence of each purified Anti-LukF-PV+HlgB-IgGs (FIG. 10*a*), anti-LukD+HlgB-IgGs (FIG. 10*b*), anti-LukF-PV+LukD-IgGs (FIG. 10*c*), and anti-LukF-PV+LukD+HlgB-IgGs (FIG. 10*d*). Column 1, no toxin (green); column 2, HlgA+HlgB (brown)
Figure 10B:
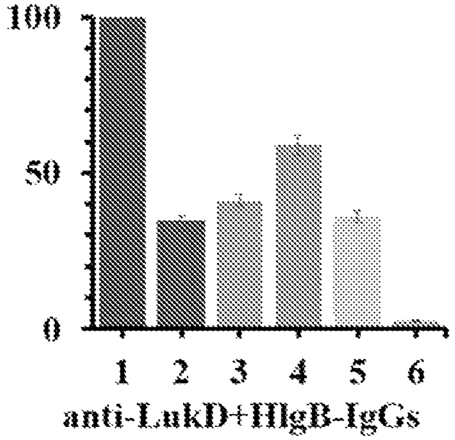
Figure 10C:
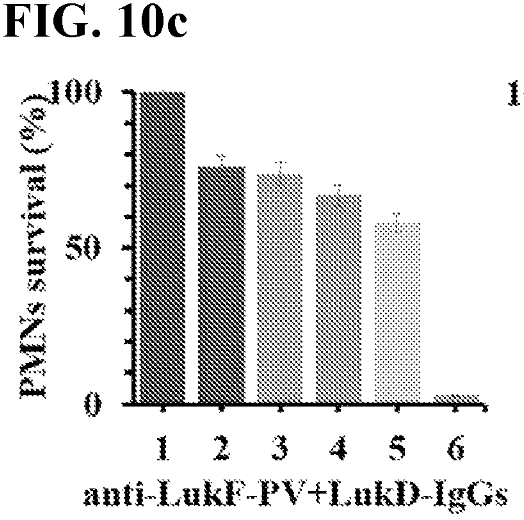
Figure 10D:
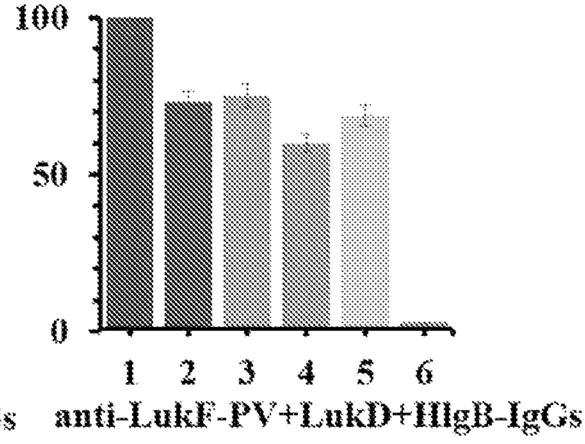

Among Anti-F-Component-IgG Combination, Mixture of Anti-LukF- And Anti-LukD-IgGs Showed Highest Level of Neutralization Activities Against Four-BCL-Mediated Cytotoxicities Further, the present inventors have examined the neutralization abilities by the combination of cognate BCL F-IgGs against 5 BCL-mediated PMNs cytolytic activities. To this end, the present inventors examined neutralization abilities by the combination of four different anti-F-component-IgGs against BCL-mediated cytolytic activities (FIGS. 10*a* to 10*d*). The average survival rates of PMNs by treatment with each mixture were as follows: anti-LukF-PV- and anti-HlgB-IgGs (52.9%. FIG. 10*a*), anti-LukD and anti-HlgB-IgG (42.6%, FIG. 10*b*), anti-LukF-PV- and anti-LukD-IgG (68.6%, FIG. 10*c*), and anti-LukF-PV-, anti-LukD and anti-HlgB-IgGs (69.0%, FIG. 10*d*). Among them, the combination of anti-LukF-PV- and anti-HlgB-IgGs showed higher PMN survival rate compared to other three combinations. These results indicated that three anti-F-component-IgGs also showed good neutralization activity against four BCL-toxic effects, but not LukAB.

Mixture of Anti-LukS-PV-, HlgA-, and $LukA_{E323A}B$-IgGs Neutralized Five BCL-Mediated PMNs Cytolytic Activities As shown from FIGS. 6*a* to 10*d*, any BCL-component-IgGs and any combination of IgGs did not inhibit LukAB-derived cytolytic activity. Therefore, the present inventors supposed that, to neutralize all five BCL-derived toxicity using anti-BCL-component-IgGs, anti-LukAB toxoid-IgGs with other selected anti-BCL-component-IgG should be used. For this reason, the present inventors have purified recombinant $LukA_{E323A}B$ toxoid and its rabbit anti-$LukA_{E323A}B$ IgG (FIG. 4). Because the present inventors found that that the mixture of anti-LukS-PV- and HlgA-IgGs highly neutralized four BCL-mediated cytolytic activity (FIG. 9*b*), the present inventors hypothesized that the mixture of three IgGs, such as anti-LukS-PV-, anti-HlgA and anti-$LukA_{E323A}B$ toxoid-IgG, will neutralize five BCL-mediated cytolytic activities. Also, the mixtures of three anti-F-component IgGs with anti-$LukA_{E323A}B$ toxoid-IgG (FIG. 10*d*) will be valuable candidates.

To address these possibilities, the present inventors incubated human PMNs with five BCLs and two different IgG combinations (FIGS. 11*a* to 11*c*). As a result of measuring the average survival rates of PMNs, the combinations of anti-LukS-PV-, anti-HlgA and anti-$LukA_{E323A}B$ toxoid-IgG (FIG. 11*a*) anti-LukF-PV, anti-HlgB- and anti-$LukA_{E323A}B$ toxoid-IgG (FIG. 11*b*) showed 94.7% and 68.0%, respectively, suggesting that the mixture of two S-component IgGs and one LukAB toxoid IgGs highly neutralized five *S. aureus* BCL-mediated PMN cytolytic activities.

Mixture of Anti-LukS-PV-, HlgA-, $Hla_{H35L}$ and $LukA_{E323A}B$-IgGs Protected Both Secreted Native *S. aureus* Toxin-Mediated Human PMN Cytolytic and Hemolytic Activities Until this time, five recombinant BCLs were used to examine human PMN cytolytic activity in vitro. Here, the present inventors examined whether purified anti-BCL IgGs also work toward the native BCLs that are secreted from pathogenic *S. aureus* USA300. To this end, the present inventors firstly checked the secreted BCL amounts during USA300 culture at different time points. As shown in FIG. 12, all five BCLs were highly secreted at 1.5 to 3 hours culturing. Under the same conditions, Hla was highly secreted at 1.5 to 9 hours. Based on these results, it was supposed that five BCLs and Hla toxins were commonly accumulated at 3-hour culturing point. Therefore, the present inventors collected the supernatant from *S. aureus*

USA3000 culture media at 3-hour culture point and concentrated to 1 mg/ml proteins concentration and used as a stock solution. When the present inventors quantified secreted BCL and Hla amounts in the stock solution by dot blot analysis, the average protein amounts of LukSF-PV, HlgAB, LukED, HlgCB, LukAB and Hla were turned out to be 0.13, 0.26, 0.32, 0.37, 0.24 and 1.50 μg/ml, respectively (Table 2).

TABLE 2

| Toxins | Protein amounts (μg/ml) after 3 hours of culture | Average amount (μg/ml) |
|---|---|---|
| LukS-PV | 0.10 | LukSF-PV 0.13 |
| LukF-PV | 0.16 | LukSF-PV 0.13 |
| HlgA | 0.17 | HlgAB 0.26 |
| HlgB | 0.40 | HlgAB 0.26 |
| HlgC | 0.34 | HlgCB, 0.37 |
| LukE | 0.36 | LukED 0.32 |
| LukD | 0.28 | LukED 0.32 |
| LukA | 0.25 | LukAB 0.24 |
| LukB | 0.22 | LukAB 0.24 |
| Hla | 1.50 | 1.50 |

Next, the present inventors examined whether native human PMNs can be protected by the mixture of four antibodies in vitro, such as anti-LukS-PV-, HlgA, $Hla_{H35L}$ and $LukA_{E323A}B$ toxoid-IgGs (FIGS. 13*a* to 13*d*). When the present inventors prepared human PMNs using Polymorphprep solution from naïve human whole blood, PMNs band was clearly shown without any damage (FIG. 13*a*, left), but, when the present inventors added six recombinant toxins (totally 4 μg of Hla, LukSF-PV, HlgAB, LukED, HlgCB, LukAB) into whole human blood, the white PMNs band was not recovered after centrifugation (FIG. 13*a*, middle). Upon adding six toxins and the mixture of four IgGs (64 μg of anti-$Hla_{H35L}$, LukS-PV-, HlgA and $LukA_{E323A}B$-IgGs) into the human whole blood, PMN band re-appeared after centrifugation (FIG. 13*a*, right). Further, when the cell numbers of recovered PMNs were counted by hemocytometer (FIG. 13*b*), only 20% PMNs were recovered from six toxin-treated whole blood (column 2) compared to control group (column 1). However, 95% PMNs were recovered from four IgGs-treated human whole blood (column 3). These results suggested that four screened IgGs of the present invention can efficiently block six toxin-mediated PMN cytolytic activities in vitro.

Also, *S. aureus* Hla and BCLs are known to induce hemolytic activity upon infection (Seilie E S, et al., 2017. *Semin Cell Dev Biol* 72:101-116). When six toxins were incubated with rabbit whole blood, higher hemolytic activity was observed compared to PBS-treated blood (FIG. 13C, tube 2), but, when 4 selected IgGs and six toxins were added to the rabbit whole blood, hemolytic activity was inhibited by 50% compared to control group (FIGS. 13*c* and 13*d*). These results supported that the mixture of four toxin antibodies of the present invention has inhibitory effects against *S. aureus* toxin-mediated human blood hemolytic activity.

Finally, the present inventors examined the protective activity by four selected IgGs against *S. aureus* culture media-mediated PMN cytolytic activity. First, to examine how much protein amounts of *S. aureus* culture media were necessary for exhibiting cytotoxic activity against human PMNs ($2\times10^6$ cells), different doses of culture media were incubated with PMNs (FIG. 14*a*). Upon addition of 16 μg/ml of culture media, PMNs were almost hydrolyzed. Based on these data, when human PMNs ($2\times10^6$ cells) were incubated with 250 μl of RPMI for 1 hour at 37° C., 100% PMNs survived (FIG. 14*b*, column 1), but, when PMNs were co-incubated with USA300 culture media (final concentration of 16 μg/ml) and the mixture of anti-LukS-PV-, HlgA-, $LukA_{E323A}B$ and $Hla_{H35L}$-IgGs (final concentration of 160 μg/ml), approximately 90% of PMNs survived (column 2). As expected, PMNs were incubated only with USA300 culture media (final concentration of 16 μg/ml), only 5% PMNs survived (column 3). These results demonstrated that 6 toxin-mediated PMN cytolytic damages were protected by addition of 4 selected toxin and toxoid-IgGs of the present invention in vitro.

Four Rabbit Anti-Toxin-IgGs Showed Bactericidal Effects Upon Co-Incubation with Human Whole Blood and *S. aureus* USA300

Serum antibodies by immunization of antigens are known to induce host-phagocyte-mediated opsonophagocytosis, resulting in the clearance of infected pathogens (Miller L S et al., 2020. FEMS *Microbiol Rev* 44:123-153). Since four selected four anti-rabbit toxin IgGs of the present invention exhibited inhibitory effects against *S. aureus* BCL and Hla toxin-mediated PMN cytolytic and RBC hemolytic effects, the present inventors examined whether the mixture of these four antibodies can induce bactericidal effects by co-incubation with *S. aureus* USA300 cells and human whole blood. To this end, USA300 cells ($2\times10^6$ cells) were co-incubated with the native purified IgGs (40 μg) or mixture of four toxin-derived IgGs (total 40 μg) and human whole blood (100 μl) for 3 hours, and then residual colony forming units (CFUs) were estimated (FIG. 15). When the control sample can show about $2\times10^6$ CFUs, naive rabbit IgGs- and the mixture four-toxin-IgGs-treated samples showed 25% and 6% CFUs compared to that of control group, respectively, suggesting that the mixture of four anti-toxin-IgGs has bactericidal effects in human whole blood.

Example 2: Exploration of CWAP Proteins that Bind to Human Complement Factor H (FH)

Experimental Methods

Preparation of pET28a Vector Containing clfA, clfB, sdrC, sdrD, sdrE, FnbpA and FnbpB N2-N3 Domains Cloning was performed using the Gibson assembly master mix (New England Biolabs, USA) according to the manufacture's protocol. The pET28a plasmid (Novagen, Germany) was used as a vector because pET28a already has the 6 histidine-harboring motif (referred to as 6-his-tag). To express $CWAP^{N2N3}$ domains, approximately 1 kbp of each gene clfA (215-575), clfB (200-555), sdrC (166-507), sdrD (224-570), sdrE (261-610), FnbpA (180-559) and FnbpB (140-500), which include N2 and N3 domains of *S. aureus* USA300 LAC strain. The coding regions were amplified by PCR (primer sequences summarized in Table 3) using Q5 high-fidelity polymerase. The cloned pET28a-clfA, clfB, sdrC, sdrD, sdrE, FnbpA and FnbpB were transformed into *E. coli* DH5α (Enzynomics, Korea) and spread on LB agar plates containing 10 μg/ml of kanamycin (Km) (Sigma-Aldrich, USA) and incubated at 37° C. overnight.

TABLE 3

Primer sequences used in Example 2

| Gene name | Primer sequence | SEQ ID NO: |
|---|---|---|
| clfA-F | ttgttagcagccggatctcatgaattagaatcgctgccagaatctga | 31 |
| clfA-R | atgggcagcagccatcatcatcatcatcacgcatttagtttagcggcagtagctg | 32 |
| clfB-F | ttgttagcagccggatctcattctgggtcaaccggcggc | 33 |
| clfB-R | atgggcagcagccatcatcatcatcatcacgttgctgaaccggtagtaaatgc | 34 |
| sdrC-F | ctttaagaaggagatataccatgagaactttaaatcgcatggcagtgaata | 35 |
| sdrC-R | cagtggtggtggtggtggtgtgtatcttcccatacatagtcacctag | 36 |
| sdrD-F | ctttaagaaggagatataccatggcacctaaacgtttgaatacaagaatgc | 37 |
| sdrD-R | cagtggtggtggtggtggtgatatacttcttgaccagctccgc | 38 |
| sdrE-F | ttgttagcagccggatctcaaattttgtataacttttcttcaggtttaacagta | 39 |
| sdrE-R | atgggcagcagccatcatcatcatcatcacgtaaacgcaaaaatgcgctttgcag | 40 |
| FnbpA-F | ctttaagaaggagatataccatggtageggaagctaaggaagctagtaa | 41 |
| FnbpA-R | cagtggtggtggtggtggtgagctgtgtggtaatcaatgtcaagag | 42 |
| FnbpB-F | taagaaggagatataccatgatgaaaagatcaactgacgttacagc | 43 |
| FnbpB-R | cagtggtggtggtggtggtgcactggcggctctgatttaaa | 44 |
| pET28a-C-fragment 1-F | gcatcctctctcgtttcatcggtatc | 45 |
| pET28a-C-fragment 1-R | caccaccaccaccaccactgagatc | 46 |
| pET28a-C-fragment 2-F | catggtatatctccttcttaaagttaaac | 47 |
| pET28a-C-fragment 2-R | gaaacgagagaggatgctcacgatac | 48 |
| pET28a-N-fragment 1-F | gcatcctctctcgtttcatcggtatc | 49 |
| pET28a-N-fragment 1-R | tgagatccggctgctaacaaagc | 50 |
| pET28a-N-fragment 2-F | gtgatgatgatgatgatggctgc | 51 |
| PET28a-N-fragment 2-R | gaaacgagagaggatgctcacgatac | 52 |
| T7 promoter | aaattaatacgactcactatagg | 53 |
| T7 terminator | atgctagttattgctcagcgg | 54 |

Transformation of pET28a-CWAP Plasmids DNAs into *E. coli* BL21(DE3) pLySs 100 ng DNAs of the prepared pET28a-clfA, clfB, sdrC, sdrD, sdrE, FnbpA and FnbpB were transformed into 100 μl of *E. coli* BL21(DE3) pLySs competent cells by the heat shock method and spread on LB agar plates containing 10 μg/ml of kanamycin (Km) and 50 μg/ml of chloramphenicol (Cm), and then incubated at 37° C. overnight.

Expression and Purification of CWAP$^{N2N3}$ Domains

The pET28a-clfA, clfB, sdrC, sdrD, sdrE, FnbpA and FnbpB-inserted *E. coli* BL21(DE3) pLySs were cultured in LB with 10 μg/ml of Km and 50 μg/ml of Cm and incubated at 37° C. overnight. 10 ml of cultured samples were inoculated into 1 L of LB containing 10 μg/ml of Km and 50 μg/ml of Cm and incubated at 37° C. for 1 hour and 30 min to 2 hour. When $OD_{600}$ reached 0.3 to 0.5, 200 μl of 1 M IPTG was added into 1 L of samples, and then samples were incubated 37° C. for 3 hours. To purify ClfA$^{N2N3}$, ClfB$^{N2N3}$, SdrC$^{N2N3}$, SdrD$^{N2N3}$, SdrE$^{N2N3}$, FnbpA$^{N2N3}$, FnbpB$^{N2N3}$ domains, the cultured solutions were centrifuged at 7,000×g at 4° C. for 20 min. After freezing the pellets at −80° C. for 30 min, the pellets were suspended in 40 ml of 20 mM sodium phosphate buffer (pH 7.4) containing 150 mM NaCl, 5 mM imidazole, 0.1% of triton X-100, and 5 mg of lysozyme (Bioshop, Canada), and one tablet of complete EDTA-free protease inhibitor cocktail (Merck, USA), and incubated at room temperature for 15 min. The samples were sonicated for 30 min on ice to break up the bacterial cell wall. The mixture was centrifuged at 20,400×g at 4° C. for 20 min. The supernatants were collected and filtered with a 0.45-μm syringe membrane filter. The expressed recombinant proteins were purified using the Ni-Sepharose 6 fast flow column (GE LifeScience, USA). Briefly, before application of samples, the Ni-Sepharose column was equilibrated with 20 mM sodium phosphate (pH 7.4) containing 150 mM NaCl and 5 mM imidazole (buffer A). After loading filtrated solutions onto the column, the column was washed with buffer A and then proteins were step-gradient eluted with 20 mM sodium phosphate (pH 7.4) containing 150 mM NaCl and 500 mM of imidazole, respectively. Eluted factions were collected and analyzed by SDS-PAGE under reducing conditions.

Preparation of $CWAP^{N2N3}$ Domains-Coupled Sepharose Affinity Column

The coupling between recombinant $CWAP^{N2N3}$ domains and CNBr-activated Sepharose beads (GE Health Care) was performed according to the manufacture's protocol. Briefly, 1 g of CNBr-activated Sepharose beads were washed 3 times with coupling buffer (0.1M $NaHCO_3$, pH 8.5). Five mg of $CWAP^{N2N3}$ proteins dissolved in 1 ml of coupling buffer were added to washed CNBr-activated beads, which were then suspended in 4 ml of coupling buffer. After incubation for 2 hours at RT, beads were washed 3 times with coupling buffer. Then, beads were incubated with 4 ml of 1M ethanolamine (pH 8.0) for 4 hours at room temperature. After incubation, beads were washed with 0.1M sodium phosphate (pH 7.2) until showing no UV absorbance at 280 nm and stored at 4° C.

Production of $CWAP^{N2N3}$ Domain Recognizing Antibodies in Rabbit

500 μg of purified $CWAP^{N2N3}$ domains dissolved in 500 μl of PBS were mixed with 500 μl of Complete Freund's Adjuvant (CFA, Sigma-Aldrich) to make an emulsion. After subcutaneous injection of the emulsion into rabbits, the same amounts of antigens were mixed and injected together with 500 μl of Incomplete Freund's Adjuvant (IFA, Sigma-Aldrich) after 7 days. One week later, 500 μl of blood were taken from the rabbit ear vein, and the generation of IgGs was examined by Western blot analysis. After confirming the generation of IgGs, rabbit sera were taken and stored at −80° C.

Purification of Rabbit Anti-$CWAP^{N2N3}$ Recognizing IgGs from Rabbit Sera

After washing *S. aureus* protein A-coupled Sepharose column (Sigma-Aldrich) with elution buffer (0.15 M glycine/HCl, pH 2.2), the column was equilibrated with washing buffer (0.1 M sodium phosphate containing 0.1 M NaCl, pH 7.4). The antigen-immunized rabbit sera (2 ml, approximately 100 mg proteins) were loaded onto the column which was then washed with washing buffer, and then the IgGs were eluted with elution buffer. The collected IgGs were neutralized immediately with neutralize buffer (1 M Tris/HCl buffer, pH 9.0). After changing to $CWAP^{N2N3}$ domains-coupled Sepharose column and washing the column with elution buffer (0.15 M glycine/HCl, pH 2.2), the column was equilibrated with washing buffer (0.1 M sodium phosphate containing 0.1 M NaCl, pH 7.4). The protein A column-collected IgG (approximately 6 mg proteins) were loaded onto the column which was then washed with washing buffer, and then the IgGs were eluted with elution buffer. The collected IgGs were neutralized immediately with neutralize buffer (1 M Tris/HCl buffer, pH 9.0). After buffer changing with PBS, the collected IgGs were analyzed by SDS-PAGE under reducing and non-reducing conditions.

Preparation of Fab'2 Fragments from Rabbit IgGs

Fab'2 fragments used in the present invention were prepared as described previously (Hymes A J et al., 1979. *J Biol Chem* 254:3148-51). Here, the method for preparation of anti-human FH-IgG Fab'2 fragments is typically applied to the preparation of other Fab'2 fragments. First, goat anti-human FH-IgGs were purified using *S. aureus* protein A-coupled Sepharose column (Sigma-Aldrich). Briefly, 500 μl (40 mg of proteins) of goat-anti-human FH (Complement Technology, Inc.) was loaded onto protein A column (1.5×8 cm, 10 ml) that was equilibrated with buffer A (0.1 M sodium phosphate, pH 7.4, containing 0.1 M NaCl). After washing the column with buffer A, bound IgGs were eluted with buffer B (0.15 M Glycine/HCl, pH 2.2) while monitoring UV absorbance at 280 nm. The collected IgGs were immediately neutralized with 1 M Tris/HCl (pH 9.0) until pH 7.5 was reached. After concentration of collected IgGs on Centricon (Merck Millipore Ltd.), 2.5 mg of goat FH IgGs and 50 μg of pepsin (Sigma-Aldrich) were mixed with 500 μl of 0.1M acetate buffer (pH 4.2) and then incubated at 37° C. for 18 hrs. Reactions were terminated by buffer-changing with cold 100 mM phosphate buffer (pH 7.4) containing 100 mM NaCl, and the reaction mixture was checked whether IgGs were properly cleaved under reducing and non-reducing conditions. When reaction proceeded, the digestion solution was concentrated and buffer-changed with buffer A for loading subsequent protein A column. The flow through (PT) fractions of protein A column containing F(ab')2 fragment were collected.

Purification of Human $CWAP^{N2N3}$ Recognizing IgGs from Human IVIg 5 ml of commercially available intravenous IgGs (IVIg, 500 mg proteins) were loaded onto the $CWAP^{N2N3}$ coupled Sepharose columns (SdrE, FnbpA: 1 ml beads; ClfA, FnbpB: 3 ml beads) and washed as described above. The human anti-$CWAP^{N2N3}$ recognizing IgGs were eluted and neutralized as described above. The obtained human IgGs were analyzed by SDS-PAGE under reducing and non-reducing conditions.

Dot Blot Immunoassay

3 μg of N2-N3 domains of $CWAP^{N2N3}$ ($ClfA^{N2N3}$, $ClfB^{N2N3}$, $SdrC^{N2N3}$, $SdrD^{N2N3}$, $SdrE^{N2N3}$, $FnbpA^{N2N3}$, $FnbpB^{N2N3}$) and BSA as a negative control were spotted on polyvinylidene fluoride (PVDF) membrane (Immobilon-$P^{SQ}$ Transfer Membrane, Merck, USA) and dried. The membrane was blocked by soaking in 5% skim milk in TBS for 2 hours at RT and then incubated with 7 μg of purified human fibrinogen (Sigma-Aldrich, USA), purified human fibronectin (Sigma-Aldrich, USA), human FH (Complement Technology, USA) and human FI (Complement Technology, USA), which were dissolved in 700 μl of 5% skim milk. Then, the membrane was washed 3 times with TBST for 10 min and incubated with 6,000-fold-diluted primary antibodies (rabbit-anti-human fibrinogen-IgG (Sigma-Aldrich, USA), rabbit-anti-human fibronectin-IgG (Sigma-Aldrich, USA), goat anti-human FH-IgG (Complement Technology, USA) and goat anti-human factor I-IgG (cat. No. A238, Complement Technology, USA) for 1 hour at RT. The membrane was washed 3 times with TBST for 10 min and incubated with 3000:1 diluted secondary antibody (mouse anti-rabbit IgG HRP or donkey anti-goat-IgG-HRP, Santa-cruz, USA) for 1 hour at RT. Then, the membrane was washed 3 times with TBST for 10 min and incubated with enhanced chemiluminescence (ECL) reagent (pico EPD, Elpis-Biotec, Korea) for 1 min.

Flow Cytometry

FACS analysis was performed to quantify the binding of FH to *S. aureus*. Bacteria were grown overnight on blood plates and then suspended in PBS. Bacteria were washed two times with PBS and the number of bacteria was estimated by measuring the OD at 600 nm. 20 μg of $CWAP^{N2N3}$ domains of $ClfA^{N2N3}$, $SdrC^{N2N3}$, $SdrE^{N2N3}$, $FnbpA^{N2N3}$, $FnbpB^{N2N3}$ rabbit F(ab')2 fragments were incubated with USA300 ($2\times10^7$ cells) at 4° C. for 1 hour. After incubation, samples were centrifuged at 1,500×g at 4° C. for 3 min, and then bacterial pellets were washed twice with 200 μl of PBS. After washing, bacteria were suspended in PBS, 30 μg FH were added and incubated at 4° C. for 1 hpur. After incubation, samples were centrifuged at 1,500×g at 4° C. for 3 min and then bacterial pellets were washed twice with 200 μl of PBS. Then, bacteria were resuspended in 20 μl of PBS with a polyclonal goat anti-human FH Fab'2-FITC conjugate and incubated for 1 hour on ice. The *S. aureus* cells were sonicated for 30 seconds to make cells single, followed by flow cytometer analysis, and 10000 events were recorded.

Cleavage of C3b into iC3b by Human FH/FI Complex in the Presence of CWAP$^{N2N3}$ Domains on the Immobilized Plate 20 μl of coating buffer, which was composed of 25 mM of sodium carbonate and 25 mM of sodium bicarbonate (pH 9.6) containing 3 μg of CWAPs$^{N2N3}$ domains, BSA and goat anti-human FH-IgG (1000:1 diluted), were coated onto microtiter plates. After washing wells with PBST 3 times, wells were incubated with 100 μl of 0.2% BSA in PBS at RT for 2 hours and then wells were washed 3 times with PBST, which contained 0.05% of Tween 20 in PBS (pH 7.4). Then, 0.37 μg of purified human FH was added. As a negative control, PBS was added instead of human FH. After 30 min of incubation, wells were washed 3 times with PBST. Then, 75 μl of mixture containing 1 μg of purified C3b and 1 μg of purified human FI in GVB$^{++}$ were added to each well and incubated at 37° C. for 3 hrs. After incubation, the supernatant was extracted and examined for the generated iC3b amounts via Western blot using 6000:1 diluted goat anti-human C3-IgG (Complement Technology, USA) as a primary antibody. Then, the membrane was washed 3 times with TBST and incubated with donkey anti-goat-IgG-HRP (Santacruz, USA) as a second antibody. After treatment with ECL reagent for 1 min, images were obtained as described above.

Detection of Human FH on Live *S. aureus* USA300 LAC Cells

Bacteria (1×10$^5$ CFUs) were prepared in 100 μl of PBS. Five μg of CWAP$^{N2N3}$ domains and 0.5 μg of FH were added thereto and incubated at 4° C. for 1 hour. After incubation, samples were centrifuged at 1,500×g at 4° C. for 3 min, and then 90 μl of supernatant was collected, and bacterial pellets were washed twice with 200 μl of PBS. Finally, the bacterial pellet was suspended with 90 μl of PBS. Each suspended bacterial pellet and the collected supernatant were loaded onto 6-15% gradient SDS-PAGE gel. After gel electrophoresis, the bands were transferred to the 0.45 μm PVDF membrane (Immobilon-P Transfer Membrane, Merck, USA) at 4° C. The membrane was blocked by soaking with 5% skim milk in TBST for 1 hour at RT. Then, the membrane was incubated with goat anti-human FH-IgG as a primary antibody, and then washed 3 times with TBST and incubated with donkey anti-goat-IgG-HRP (Santacruz, USA) as a second antibody. After treatment with ECL reagent for 1 min, images were obtained as described above.

Measurement of iC3b Amounts in the Presence of CWAPs$^{N2N3}$ Domains

*S. aureus* USA300 LAC strain cells (1×10$^5$ CFUs) were prepared in 100 μl of GVB$^{++}$. 10 μg of CWAPs$^{N2N3}$ and 0.1 μg of human FH were added thereto and incubated at 4° C. for 1 hour. After incubation, samples were centrifuged at 1,500×g at 4° C. for 3 min and 90 μl of supernatant was collected. Bacterial pellets were washed twice with 200 μl of PBS. Then, 1.5 μg of purified C3b, 0.25 μg of purified human FI in GVB$^{++}$ were added to the supernatant and pellet, and then incubated at 37° C. for 3 hours. Each pellet and the collected supernatant were loaded onto 6-15% gradient SDS-PAGE gel. After gel electrophoresis, the bands were transferred to the PVDF membrane at 4° C. The membrane was blocked by soaking with 5% skim milk in TBST for 1 hour at RT. Then, the membrane was incubated with goat anti-human C3-IgG as a primary antibody. The membrane was washed 3 times with TBST and incubated with donkey anti-goat-IgG-HRP as a second antibody (Santacruz, USA). After treatment with ECL reagent for 1 min, images were obtained as described above.

Examination of Binding Specificities of Rabbit Anti-CWAP-Fab'2 Against Other CWAP$^{N2N3}$ Domains 1 μg of CWAPs$^{N2N3}$ domains (ClfA$^{N2N3}$, ClfB$^{N2N3}$, SdrC$^{N2N3}$, SdrD$^{N2N3}$, SdrE$^{N2N3}$, FnbpA$^{N2N3}$, FnbpB$^{N2N3}$) were spotted on polyvinylidene fluoride (PVDF) membrane and dried. The membrane was blocked by soaking in 5% skim milk in TBS for 2 hours at RT, and then the membrane was incubated with 6,000:1 diluted primary antibodies (anti-CWAP$^{N2N3}$ domain recognizing rabbit Fab'2) in 5% skim milk for 1 hour at RT. The membranes were washed 3 times with TBST for 10 min and incubated with 3000:1 diluted secondary antibody (mouse anti-rabbit IgG HRP, Santacruz, USA) in 5% skim milk for 1 hour at RT. Then, the membrane was washed 3 times with TBST for 10 min and incubated with ECL reagent (pico EPD, Elpis-Biotec, Korea) for 1 min, and then images were obtained as described above.

Examination of Binding Specificities of Rabbit and Human Anti-CWAP-IgGs Against Other CWAP$^{N2N3}$ Domains 200 ng of CWAPs$^{N2N3}$ domains (ClfA$^{N2N3}$, ClfB$^{N2N3}$, SdrC$^{N2N3}$, SdrD$^{N2N3}$, SdrE$^{N2N3}$, FnbpA$^{N2N3}$, FnbpB$^{N2N3}$) were loaded onto SDS-PAGE gel. After gel electrophoresis, the bands were transferred to the PVDF membrane at 4° C. The membrane was blocked by soaking in 5% skim milk in TBST for 1 hour at RT, and then the membrane was incubated with 6,000:1 diluted primary antibodies (anti-CWAP$^{N2N3}$ domain recognizing rabbit and human IgGs) in 5% skim milk for 1 hour at RT. The membrane was washed 3 times with TBST for 10 min and incubated with 3000:1 diluted secondary antibody (mouse anti-rabbit IgG HRP, goat anti-human IgG HRP, Santacruz, USA) in 5% skim milk for 1 hour at RT. Then, the membrane was washed 3 times with TBST for 10 min and incubated with ECL reagent (pico EPD, Elpis-Biotec, Korea) for 1 min, and then images were obtained as described above.

Bactericidal Activities of *S. aureus* by CWAP$^{N2N3}$ Domain and by Purified Human or rabbit CWAP$^{N2N3}$ Recognizing IgGs in Human Whole Blood The opsonophagocytotic bacterial killing assay using human whole blood was performed as described previously (van der Maten E et al., 2017. Sci Rep 7:42137). Briefly, the purified CWAP$^{N2N3}$ proteins, human and rabbit anti-CWAPN$^{N2N3}$-IgGs were diluted with PBS to 0.5 mg/ml. After adding 100 μl of fresh whole blood into 1.5 ml tube, the mixture of 10 μl of proteins or IgGs (5 μg) was added into the same tube and vortexed. Finally, 100 μl of USA300 cells (1×10$^5$ cells/well) were added and suspended 10 times, and vortexed for 10 to 20 seconds. The mixture was incubated for 3 hours at 37° C. After incubation, bacteria were serially diluted and spread on TSB agar plates or sheep blood plates for counting CFUs.

Data Processing and Statistical Analysis

Unless otherwise stated, experiments were carried out at least three times independently, and the results were presented as the mean±SD. Other experimental results are a representative of at least three independent experiments that yielded similar results. Statistical significance was measured by unpaired Student's t test or Log-rank test with GraphPad Prism software. Differences were considered statistically significant when the P value was equal to or less than 0.05.

Experimental Results

Three N2-N3 Domains of Cell-Wall Associated Proteins (CWAPs) Bind Human Complement Factor H (FH)

To examine whether staphylococcal CWAPs' N2-N3 domains (referred to as CWAP$^{N2N3}$) can recognize a novel ligand molecule in human sera, the coding region of seven CWAP$^{N2N3}$ (about 350-370 amino acids length with tagged with 6×His, FIGS. 16*a* and 16*b*) were amplified by PCR and then the PCR products (FIG. S1) were cloned into pET28a vector, resulting in the expression construct (pET28a-CWAP$^{N2N3}$). For overproduction of His-tagged recombinant CWAP$^{N2N3}$, cultivated *E. coli* BL21(DE3) cells harboring pET28a-CWAP$^{N2N3}$ were stimulated with 0.2 mM IPTG at 37° C. for 3 hours. The purified proteins by nickel-affinity column were migrated with the expected molecular sizes around 35 to 45 kDa on SDS-PAGE (FIG. 16*c*). The yield was calculated to be about 15 to 20 mg of purified CWAP$^{N2N3}$ from one liter of culture medium.

Because CWAP$^{N2N3}$ have similar three-dimensional structure (Arora S, et al., 2016. *Front Microbiol* 7:540), the present inventors examined whether four human proteins (fibrinogen (Fg), fibronectin (Fn), complement factor H (FH) and complement factor I (FI)) can recognize seven CWAP$^{N2N3}$ in vitro. After confirming the same amounts of proteins to be blotted on PVDF membrane by staining with Ponceau S dye, each PVDF membrane strip was incubated with each 7 μg of human Fg, Fn, FH and FI proteins by dot blot immunoassay. After washing unbound proteins, bound proteins on the membrane were examined by their specific anti-Fg-, Fn-, FH-, and FI-IgGs (FIG. 17*a*). In the above conditions, human Fg showed high specific binding ability to FnbpA$^{N2N3}$ as reported previously (Deivanayagam C C et al., 2002. *Embo j* 21:6660-72.), whereas Fn showed specific binding ability to FnbpB$^{N2N3}$ (Broker B M et al, 2014. *Int J Med Microbiol* 304:204-14), indicating that two Fnbp$^{N2N3}$ proteins have high binding abilities to human Fg and Fn proteins. Also, human FH was recognized by four CWAP$^{N2N3}$ (ClfA$^{N2N3}$, SdrE$^{N2N3}$, FnbpA$^{N2N3}$ and FnbpB$^{N2N3}$). Under the same conditions, five CWAPs$^{N2N3}$ proteins (ClfA$^{N2N3}$, SdrC$^{N2N3}$, SdrE$^{N2N3}$, FnbpA$^{N2N3}$ and FnbpB$^{N2N3}$) showed the ability to bind to FI. Interestingly, ClfB$^{N2N3}$ and SdrD$^{N2N3}$ did not show any binding ability against these four human proteins. Although the interactions between FnbpA and Fg, between FnbpB$^{N2N3}$ and Fn, and between SdrE$^{N2N3}$ and FH or FI, were previously reported (Sharp J A, et al., 2012. *PLoS One* 7:e38407; Bingham R J et al., 2008. *Proc Natl Acad Sci USA* 105:12254-8; Burke FM e al., 2011. *FEBS J* 278:2359-71; Zhang Y et al., 2017. *Biochem J* 474:1619-163130), the interactions between ClfA$^{N2N3}$, FnbpA$^{N2N3}$, FnbpB$^{N2N3}$ and FH, FI were not reported previously.

If these CWAP$^{N2N3}$ domains have abilities to bind human FH, it can be expected that FH-bound CWAP$^{N2N3}$ domains will induce conversion of complement C3b to iC3b in the presence of FI. To prove this possibility, both SdrE$^{N2N3}$ and anti-FH-IgGs proteins were used as positive control proteins since SdrE$^{N2N3}$ was reported to bind human FH (Sharp J A et al., 2012. *PLoS One* 7:e38407; Zhang Y et al., 2017. *Biochem J* 474:1619-1631) and since anti-FH-IgGs have ability to bind FH. As shown in FIG. 17*b*, seven CWAP$^{N2N3}$ proteins were coated onto the microplate with positive control proteins. BSA was also coated as a negative control. After incubation with FH, unbound FH was washed out. After addition of C3b and FI, the plate was then incubated for 3 hours at 37° C. The generated iC3b was detected using anti-C3-mAb by Western blot analysis (FIG. 17*b*). As expected, the BSA-coated fraction almost did not generate 42 kDa fragments of iC3b even when adding FH/C3b/FI (lane 1), indicating that BSA cannot recruit FH. However, SdrE$^{N2N3}$-coated and anti-FH-IgG-coated fractions highly generated 42 kDa fragment in the presence of FH/C3b/FI (lanes 11 and 17), not in the presence of FI/C3b only (lanes 12 and 18), suggesting that SdrE$^{N2N3}$ and anti-FH-IgG can recruit FH, leading to conversion of C3b to iC3b by FI. Under the same conditions, ClfA$^{N2N3}$, FnbpA$^{N2N3}$ and FnbpB$^{N2N3}$-coated fractions produced 42 kDa fragments by adding FH, C3b and FI (lanes 3, 13 and 15, respectively), but not in the absence of FH (lanes 4, 14 and 16). These results re-confirmed that ClfA$^{N2N3}$, FnbpA$^{N2N3}$, FnbpB$^{N2N3}$ and SdrE$^{N2N3}$ domains have capabilities to bind human FH and then further FH is able to recruit FI, leading to hydrolysis of complement C3b to iC3b in vitro.

By Addition of FH-Binding CWAP$^{N2N3}$ Proteins, FH Recruitment onto *S. aureus* Cell Surface was Inhibited, Resulting in Decrease of Conversion of C3b to iC3b Since the present inventors observed that four *S. aureus* CWAPs showed binding abilities to FH, the present inventors examined whether FH recruitment on native CWAP-expressing live *S. aureus* cells can be inhibited by addition of FH-binding CWAP$^{N2N3}$ proteins. To this end, live *S. aureus* USA300 LAC cells were incubated with FH and five different proteins (ClfA$^{N2N3}$, SdrE$^{N2N3}$, FnbpA$^{N2N3}$, FnbpB$^{N2N3}$, and SdrC) (FIG. 18*a*). In case of PBS condition, added all FH protein was recruited on the bacterial surface (pellet) (lane 2) and not present in the supernatant (lane 1), indicating that *S. aureus* cells recruit FH. In case of ClfA$^{N2N3}$, SdrE$^{N2N3}$, and FnbpA$^{N2N3}$, almost half amounts of added FH existed in the supernatant (lanes 3, 5, and 7) and the other half amounts existed on the pellets (lanes 4, 6 and 8). As expected, addition of FnbpB$^{N2N3}$ completely inhibited the enrichment of FH on the bacterial surface (lane 10), leading to accumulation of all added FH in the supernatant (lane 9). In contrast, in case of SdrC$^{N2N3}$ protein, which was shown to have no ability to bind to FH (FIG. 17*a*), all added FH was recruited on the bacterial surface (lane 12), not in the supernatant (lane 11), indicating that SdrC$^{N2N3}$ protein has no inhibitory effects on FH binding to *S. aureus* (lane 11). Taken together, these results support that four FH-binding proteins (FnbpA$^{N2N3}$, FnbpB$^{N2N3}$, SdrE$^{N2N3}$ and ClfA$^{N2N3}$) function as competitive inhibitors with naïve CWAP proteins expressed on bacterial surface by binding FH. Among four proteins, FnbpB$^{N2N3}$ highly inhibited FH recruitment on *S. aureus* surface.

To further confirm these observations, the present inventors supposed that it would be valuable to examine whether FH-recognizing CWAP$^{N2N3}$ proteins can prevent FH-mediated iC3b generation on the *S. aureus* USA300 cell surface. The present inventors supposed that when *S. aureus* cells were incubated with FH/C3b/FI in the absence of FH-binding CWAP$^{N2N3}$ proteins, recruited FH on the bacterial surface will generate higher amounts of 43 kDa iC3b fragments from 100 kDa C3b. However, when FH-binding CWAP$^{N2N3}$ proteins are added, small amounts of FH will be recruited on the bacterial surface due to capturing FH by added CWAPs$^{N2N3}$ proteins, resulting in smaller amounts of 43 kDa iC3b deposition on the bacterial surface. To prove this possibility, when *S. aureus* USA300 cells were incubated with FH/C3b/FI and each five proteins (FIG. 18*b*), the amounts of produced iC3b amounts on PBS and SdrC added fractions were higher than those of four FH-binding CWAP$^{N2N3}$ proteins (lanes 1 and 3 vs lanes 2, 4-6, respectively). These results strongly indicated that FH-binding CWAP$^{N2N3}$ proteins inhibit the conversion of C3b to iC3b by capturing complement FH, leading to prevention of FI-mediated C3b conversion to iC3b on the bacterial surface.

Rabbit Anti-CWAP$^{N2N3}$ F(ab')$_2$ Fragments Inhibited FH Recruitment on the *S. aureus* Cell Surface Next, the present inventors tried to know whether rabbit anti-FH-binding CWAP$^{N2N3}$-IgG can also inhibit FH recruitment on the live *S. aureus* USA300 cell surface. To this end, it is difficult for the present inventors to use rabbit anti-human FH-IgGs or rabbit anti-CWAP$^{N2N3}$-IgGs since *S. aureus* protein A may non-specifically capture native IgGs by binding to Fc domains of IgGs. To solve this problem, the present inventors decided to prepare six different F(ab')2 fragments from native FH-IgGs and five anti-FH-binding CWAP$^{N2N3}$-IgGs proteins by pepsin treatments (FIG. 23). As shown in FIG. 24*a*, purified anti-FH-Fab'2 and five anti-CWAP$^{N2N3}$ F(ab')2 fragments showed 100 kDa size under non-reducing and 25 kDa size under reducing conditions, respectively, suggesting that all prepared anti-Fab'2 fragments were properly prepared. As a result of examining the binding specificities of six purified anti-Fab'2 fragments against their cognate antigens, four F(ab')2 fragments of ClfA$^{N2N3}$, FnbpA$^{N2N3}$, FnbpB$^{N2N3}$ and FH specifically recognized their cognate antigens (FIGS. 24*b* and 24*c*), but two Fab'2 fragments of SdrC$^{N2N3}$ and SdrE$^{N2N3}$ weakly recognized SdrD$^{N2N3}$ and FnbpB$^{N2N3}$ (FIG. 24*c*), respectively, suggesting that six prepared Fab'2 fragments had desired characteristics.

As shown in FIG. 19*a*, FITC-conjugated anti-FH-Fab'2 fragment properly recognized recruited FH on the bacterial surface when USA300 cells were co-incubated with FH, indicating that FH can bind CWAP proteins of live USA 300 cells. Further, to examine the binding specificity of FH binding to four CWAP$^{N2-N3}$ proteins of live bacteria, *S. aureus* USA300 cells (2×10$^{7}$ cells) were first incubated with five different anti-CWAP Fab'2 fragments (each 20 μg protein amounts) and then bacterial cells were washed to remove unbound anti-CWAP F(ab')2 fragments. Then, *S. aureus* USA300 cells were incubated with purified FH (each 30 μg protein amounts) and then bacterial cells were washed to remove unbound FH. Then, recruited FH amounts on each anti-CWAP Fab'2 fragments-treated bacterial cell surface were examined using FITC-conjugated anti-FH-Fab'2 fragment by FACS analyses (FIG. 19*a*). Three anti-CWAP$^{N2N3}$-Fab'2 fragments (SdrE, FnbpA and FnbpB)-treated bacterial cells specifically inhibited FH binding to bacterial cells compared anti-Fab'2 fragment-non treated cells (FIG. 19*a* (c-e vs a)), but anti-ClfA Fab'2 fragments treatment showed low level of inhibitory effects (b of FIG. 19*a*). As expected, 20 μg of anti-SdrC-Fab'2 fragment treatment did not affect FH binding to USA300 cells (f of FIG. 19*a*). Taken together, these results re-confirmed that anti-purified four CWAP$^{N2N3}$ antibodies have abilities to block FH binding to native CWAP proteins expressed on the live bacteria.

Based on the FACS data, the recruited FH amounts on the bacterial surface were quantified (FIG. 19*b*). As expected, anti-FnbpB-Fab'2 fragment showed 60% inhibition of FH binding to *S. aureus* cell surface compared to control group (columns 6 vs 1). The inhibition abilities gradually decreased in the order of anti-SdrE (50%, column 4)>FnbpA (40%, column 5)>ClfA-Fab'2 (30%, column 6). Anti-SdrC-Fab'2 fragment almost did not show any inhibitory effects (10%, column3). These results coincide with those of FIG. 2*a*.

Purified Rabbit FH-Binding CWAP$^{N2N3}$ Proteins and their Antibodies Enhance Human Whole Blood-Mediated Bactericidal Activities Against *S. aureus* USA300 Cells The present inventors hypothesized that if the present inventors can obtain human and rabbit anti-CWAP$^{N2N3}$ domain recognizing IgGs from human intravenous IgGs (IVIg) and rabbit sera, respectively, these anti-FH-binding CWAP$^{N2N3}$-recognizing IgGs will bind *S. aureus* naïve CWAP proteins and this binding will prevent the recruitment of FH on *S. aureus* surface, resulting in the enhancement of C3b-mediated opsonophagocytosis by host phagocytes. To prove this assumption, the present inventors purified human and rabbit anti-CWAP$^{N2N3}$ recognizing IgGs, such as anti-ClfA$^{N2N3}$, anti-SdrE$^{N2N3}$, anti-FnbpA$^{N2N3}$, and anti-FnbpB$^{N2N3}$-IgGs. The purification of these four IgGs was carried out using their specific protein-conjugated Sepharose columns. As for human sera sources, commercially-available human IVIg was used since healthy human sera are known to contain anti-*S. aureus* CWAP-specific-antibodies (Dryla A et al., 2005. *Clin Diagn Lab Immunol* 12:387-98). Rabbit sera were obtained by three times immunization of CWAP$^{N2N3}$ domains into rabbits. After loading human IVIg or anti-CWAP$^{N2N3}$ domains-immunized rabbit sera onto CWAPN$^{N2N3}$-conjugated columns, rabbit anti-CWAP$^{N2N3}$ domains recognizing-IgGs (FIG. 24) and human anti-CWAP$^{N2N3}$ domains recognizing-IgGs (FIG. 25) were eluted. As a result, human IVIg contained approximately 0.1% anti-CWAPs$^{N2N3}$ domain-recognizing IgGs and rabbit sera contained approximately 1% anti-CWAP$^{N2N3}$ domain-recognizing IgGs. As a result of examining the purities of these four IgGs on SDS-PAGE under reducing and non-reducing conditions (FIG. 26), it could be seen that purified IgGs form tetramer structures in the non-reducing conditions.

Next, the present inventors have examined the specificities of purified rabbit and human IgGs against their antigens (FnbpA$^{N2N3}$, FnbpB$^{N2N3}$, ClfA$^{N2N3}$, and SdrE$^{N2N3}$ domains) by Western blot analyses or dot blot analysis, respectively. As shown in FIG. 20*a*, four rabbit anti-CWAP$^{N2N3}$-recognizing IgGs specifically recognized their cognate antigens against seven CWAP$^{N2N3}$ domains, but purified human anti-CWAP-IgGs showed broad recognition patterns except for ClfA (FIG. 20*b*). For examples, anti-SdrE$^{N2N3}$-IgGs recognized four antigens (ClfA and three Sdr family proteins). Also, anti-FnbpAN2N3 domain recognized five antigens (three Sdr and two FNBP family proteins). Anti-FnbpB$^{N2N3}$-IgGs also recognized four antigens (ClfB$^{N2N3}$, SdrE$^{N2N3}$ and two FNBP$^{N2N3}$ proteins) (FIG. 20*b*). These results suggest that human anti-CWAP$^{N2N3}$-IgGs have more broad recognition patterns compared to rabbit anti-CWAP$^{N2N3}$-IgGs.

Finally, the present inventors tried to estimate psonophagocytoses-mediated bacterial killing activities of CWAP$^{N2N3}$ domains or these purified antibodies. After incubation of *S. aureus* USA300 cells (1×10$^{5}$ cells) with CWAP$^{N2N3}$ domains proteins (5 μg) in 100 μl of human whole blood for 3 hours at 37° C., colony-forming units (CFUs) of *S. aureus* USA300 LAC cells were measured. When each CWAP$^{N2N3}$ domain was added, CFUs were significantly decreased compared to the control group (FIG. 21*a*). These results support that CWAP$^{N2N3}$ domains may inhibit the FH recruitment on *S. aureus* cell surface, leading to the increase of C3b deposition and induction of C3b-mediated opsononophagocytosis by host phagocytes. In the same way, the present inventors examined the effects of human and rabbit anti-CWAP$^{N2N3}$-IgGs-mediated bactericidal effects against *S. aureus* USA300 LAC cells using human whole blood (FIGS. 21*b* and 21*c*). By incubation of human anti-CWAP$^{N2N3}$-IgGs (5 μg) with *S. aureus* USA300 LAC cells (1×10$^{5}$ cells) in 100 μl of human whole blood for 3 h at 37° C., the CFUs were decreased 2 to 4 times compared to the control groups, such as PBS, human IVIg and naïve rabbit sera (FIGS. 21*b* and 21*c*). Further, when the mixture of anti-ClfA$^{N2N3}$ and FnbpB$^{N2N3}$ IgGs was added to the mixture of bacteria and whole blood, CFUs were also decreased compared to the control group (FIG. 21*b*). Also, when the mixture of 5 μg of rabbit anti-ClfA, anti-FnbpB and anti-FNBPA$^{N2N3}$-IgGs was added to the mixture of bacteria and whole blood, CFUs were decreased 2 times compared to that of naïve rabbit IgGs (FIG. 21*c*). In case of rabbit IgGs, the present inventors observed that the mixture of four IgGs showed higher bactericidal activity than the single IgGs. Taken together, these results support that anti-CWAP$^{N2N3}$ domains IgGs have specific bactericidal activity against *S. aureus* USA300 LAC strain upon incubation with human whole blood.

Example 3: Selection of Blood Coagulation Inhibitors

Experimental Methods

Purification of Recombinant Coa and vWbp Proteins

Polyhistidine-tagged recombinant six proteins (Coa$^{whole}$, coa$^{N}$, coa$^{C}$, vWbp$^{whole}$, vWbp$^{N}$, and vWbp$^{C}$) were cloned and expressed using an *E. coli* expression system. These genes were amplified by PCR from USA300 genome sequences using Q5 High Fidelity DNA polymerase (Thermo Fisher Scientific). The PCR product was cloned into pET28a-vector, resulting in expression of proteins with an N-terminal or C-terminal 6×His-tag. For purification of cloned recombinant proteins, the present inventors inserted 6×His-tag in both N- and C-terminal regions. Obtained clones were sequenced to verify the correct construction. The recombinant proteins were expressed in BL21 pLysS *E. coli* using 0.2 mM isopropy-1β-D-1-thiogalactopyranoside (IPTG). The expressed proteins were purified using Ni-Sepharose 6 fast flow resin (GE healthcare, 17-5318-01, 5 ml) with loading buffer (20 mM sodium phosphate, 0.1% triton X-100, 150 mM NaCl, 5 mM imidazole, pH 7.4), washing buffer (20 mM sodium phosphate, 150 mM NaCl, 5 mM imidazole, pH 7.4) and elution buffer (20 mM sodium phosphate, 150 mM NaCl, 500 mM imidazole, pH 7.4).

SDS PAGE Analysis of the Purified Recombinant coa and vWbp Domain Proteins

3 μg of each domain protein (coa$^{whole}$, Coa$^{N}$, coa$^{C}$; vWbp$^{whole}$; vWbp$^{N}$; vWbp$^{C}$) was mixed with 4× loading sample buffer (LSB, SH+) and then loaded onto 15% SDS-PAGE gel for 1 hour (35 mA, 600V, 100 W).

Rabbit Immunization for Obtaining coa and vWbp Protein Antibodies

500 μg of purified single components of *S. aureus* Coa and vWbp proteins dissolved in 500 μl of PBS were mixed with 500 μl of Complete Freund's Adjuvant (Sigma-Aldrich) and mixed to make emulsions. After subcutaneous injection of each emulsion into rabbits, and two weeks later, the same amounts of antigens were mixed with 500 μl of Incomplete Freund's Adjuvant (Sigma-Aldrich) and injected via subcutaneous route. Two week later, 500 μl of blood were taken from the rabbit ear vein and the generation of IgGs of each antigen was examined by Western blot analysis. If antibodies were produced, rabbit whole bloods were collected and sera were obtained therefrom. Rabbit sera were stored at −80° C. until use.

Examination of Raised Antibody-Specificity Against Different Domain Proteins of Coa and vWbp 3 μg of each domain protein (Coa$^{whole}$, Coa$^{N}$, Coa$^{C}$; vWbp$^{whole}$; vWbp$^{N}$; vWbp$^{C}$) and negative control protein (BSA) were spotted on polyvinylidene fluoride (PVDF) membrane (0.22 μm, Immobilon-P$^{SQ}$ Transfer Membrane, Merck, USA) and dried. The membrane was blocked by soaking in 5% skim milk in TBS for 2 hours at RT and then the membrane was incubated with 3,000:1 diluted primary antibodies (anti-rCoa$^{whole}$ and -rCoa$^{N}$, -rvWbp$^{whole}$, -r vWbp$^{N}$) in 5% skim milk for 1 hour at RT. The membrane was washed 3 times with TBST for 10 min and incubated with 6000:1 diluted secondary antibody (mouse anti-rabbit IgG HRP, Santacruz, USA) in 5% skim milk for 1 hour at RT. Then, the membrane was washed 3 times with TBST for 10 min and incubated with ECL reagent (pico EPD, Elpis-Biotec, Korea) for 1 min.

Expression Patterns of Coa and vWbp Proteins During *S. aureus* USA300 Culture in RPMI Medium USA300 was cultured in 10 ml of RPMI at 37° C. at 180 rpm overnight. Then, 1 ml of bacteria seed culture solution was added to 50 ml of RPMI and cultured at 37° C. at 180 rpm, and 1 ml of bacteria culture solution was taken at different time points (0 h, 1.5 h, 3 h, 6 h, 9 h, 12 h). Then, the taken bacteria culture solution was measured for its optical density ($OD_{600}$) value, and then centrifuged at 4,400×g at RT for 3 min. 20 μl of bacteria supernatant was loaded onto 15% SDS-PAGE gel. After gel electrophoresis, the bands were transferred to the PVDF membrane at 4° C. The membrane was blocked by soaking with 5% skim milk in TBST for 1 hour at RT. Then, the membrane was incubated with anti-rabbit-Coa$^{whole}$- and anti-rabbit -rvWbp$^{whole}$-IgGs as a primary antibody. The membrane was washed 3 times with TBST and incubated with mouse anti-rabbit-IgG-HRP as a second antibody (Santacruz, USA). After treatment with ECL reagent for 1 min, images were obtained.

Identification of coa and vWbp-Recognition Proteins Expressed on the *S. aureus* Cell Surface 3 μg of N2-N3 domains of seven different recombinant MSCRAMMs (ClfA$^{N2N3}$, ClfB$^{N2N3}$, SdrC$^{N2N3}$, SdrD$^{N2N3}$, SdrE$^{N2N3}$, FnbpA$^{N2N3}$, FnbpB$^{N2N3}$) and BSA as a negative control were spotted on polyvinylidene fluoride (PVDF) membrane (Immobilon-P$^{SQ}$ Transfer Membrane, Merck, USA) and dried. The membrane was blocked by soaking in 5% skim milk in TBS for 2 hours at RT and then incubated with 7 μg of different purified recombinant Coa$^{whole}$, Coa$^{N}$, Coa$^{C}$ or vWbp$^{whole}$; vWbp$^{N}$; vWbp$^{C}$, which were dissolved in 700 μl of 5% skim milk. Then, the membrane was washed 3 times with TBST for 10 min and incubated with 3,000-fold diluted primary antibodies (anti-rabbit-Coa$^{whole}$-IgG, anti-rabbit-Coa$^{N}$-IgG, anti-rabbit-Coa$^{C}$-IgG, anti-rabbit-vWbp$^{whole}$-IgG, anti-rabbit-vWbp$^{N}$-IgG, anti-rabbit-vWbp$^{C}$-IgG) for 1 hour at RT. The membrane was washed 3 times with TBST for 10 min and incubated with 6000:1 diluted secondary antibody (mouse anti-rabbit IgG HRP, Santacruz, USA) for 1 hour at RT. Then, the membrane was washed 3 times with TBST for 10 min and incubated with enhanced chemiluminescence (ECL) reagent (pico EPD, Elpis-Biotec, Korea) for 1 min.

Confirmation of Binding Specificity Between Coa and Fnbp Proteins Using Anti-Fnbp-F(ab)$_2$' Fragments 3 μg of Coa$^{C}$ protein or 20 μg of anti-Fnbp-F(ab)$_2$', and anti-SdrC-F(ab)$_2$' fragment as negative control, were co-incubated with bacteria cells (USA300, 1×10$^5$ CFUs) at 4° C. for 1 hour. After incubation, samples were centrifuged at 4,400×g at 4° C. for 3 min, and then bacterial pellets were washed twice with 500 μl of PBS. Each suspended bacterial pellet was loaded onto 15% gradient SDS-PAGE gel. After gel electrophoresis, the bands were transferred to the 0.45-μm PVDF membrane (Immobilon-P Transfer Membrane, Merck, USA) at 4° C. The membrane was blocked by soaking with 5% skim milk in TBST for 1 hour at RT. Then, the membrane was incubated with anti-rabbit-Coa$^{C}$-IgG as a primary antibody, and then washed 3 times with TBST and incubated with mouse anti-rabbit IgG HRP (Santacruz, USA) as a second antibody. After treatment with ECL reagent for 1 min, images were obtained.

Induction of Blood Coagulation by Different Dose of Purified coa$^{whole}$ or vWbp$^{whole}$ 200 μl of hirudin-treated human blood was placed in 5-ml round-bottom tube. Then, different amounts of Coa$^{whole}$ and vWbp$^{whole}$ (1 μg, 5 μg, 10 μg, 20 μg, 40 μg, 50 μg) or PBS were added. Samples were incubated at room temperature, and blood coagulation was verified by tipping the tubes to 45° angles at intervals of 1.5 hours.

Measurement for Prevention of Blood Coagulation by Different Dose of Purified anti-Coa$^{whole}$-IgG or anti-vWbp$^{whole}$-IgG 200 μl of hirudin-treated human blood was placed in 5-ml round-bottom tube. Then, different amounts of anti-Coa$^{whole}$-IgG and anti-vWbp$^{whole}$-IgG (10 μg, 20 μg, 40 μg, 80 μg, 100 μg) were added. Next, 5 μg of Coa$^{whole}$ and vWbp$^{whole}$ or PBS was added. Samples were incubated at room temperature, and blood coagulation was verified by tipping the tubes to 45° angles at intervals of 1.5 hours.

Measurement of Inhibition Effects of Anti-Coa$^{whole}$ IgG or Anti-vWbp$^{whole}$ IgG Against Secreted Coa and vWbp-Mediated Blood Coagulation

*S. aureus* USA300 LAC cells were cultured in 50 ml of RPMI at 37° C. at 180 rpm for 2 hours, and then bacteria were centrifuged at 4,400×g at 4° C. for 3 min and 100 μl of bacteria supernatant was added into 200 μl of hirudin-treated human blood. 5 μg of vWbp$^{whole}$ and 1 μg of Coa$^{whole}$ were added to 200 μl of hirudin-treated human blood as positive control. 80 μg of anti-coa$^{whole}$-IgG and 80 μg of anti-vWbp$^{whole}$-IgG or 40 μg of anti-coa$^{whole}$-IgG mixed with 40 μg of anti-vWbp$^{whole}$-IgG were added to 200 μl of hirudin-treated human blood, and then 100 μl of bacteria supernatant was added. Samples were incubated at room temperature, and blood coagulation was verified by tipping the tubes to 45° angles at intervals of 1.5 hours.

Inhibitory Effect of anti-Coa$^{whole}$-IgG or vWbp$^{whole}$-IgG Against Blood Coagulation in vivo To verify the in vivo effects of Coa$^{whole}$ and vWbp$^{whole}$, in vivo passive immunity experiments were performed using antibodies obtained by injecting them into rabbits. First, 4 rabbits were divided into 2 groups, each consisting of 2 rabbits (FIG. 37). The first group was injected with PBS and then injected with the *S. aureus* USA300 strain (1.6×10$^{8}$ CFUs) via the ear vein. The second group was injected with a mixture of 1 mg of coa$^{whole}$ protein-conjugated Sepharose column-purified anti-coa$^{whole}$-IgG and 1 mg of vWbp$^{whole}$ protein-conjugated Sepharose column-purified anti-vWbp$^{whole}$-IgG via the left ear vein, and after 1 hour, injected with the *S. aureus* USA300 strain (1.6×10$^{8}$ CFUs) via the right ear vein. Then, the weight change and survival rate of the rabbits were examined.

Experimental Results

Cloning and Purification of Recombinant *S. aureus* Coagulase and vonWillebrand Factor-Binding Domain Proteins (vWbp)

Since it has been proposed that *S. aureus* Coa and vWbp proteins function as major *S. aureus* virulence factors, the present inventors hypothesized that these factors will bind to bacteria surface during infection via specific receptor(s) rather than working as secreted factors in order to escape more efficiently from host immunity by production of fibrin clot in blood vessel, suggesting that some unidentified receptor protein(s) will exist on the bacterial surface. If the present inventors can find this receptor on the bacterial surface, the antibody against the receptor will block the interaction between Coa or vWbp and receptor, leading to prevention of fibrin clot generation. To identify these receptors expressed on bacterial surface, the present inventors prepared recombinant proteins harboring Coa and vWbp domains and their specific antibodies.

Examination of Raised Antibody-Specificity Against Different Domain Proteins of Coa and vWbp by Dot Blot Analyses As shown in FIG. 27, the present inventors constructed six proteins, namely, two whole Coa and vWbp proteins, two N-terminal D1-D2 domains, and two C-terminal repeat domain of Coa and vWbp, based on the genome sequences of *S. aureus* USA300 LAC strain. The whole proteins of Coa and vWbp were composed of 607 and 508 amino acids (aa), respectively, and N-terminal domains of Coa and vWbp consisted of 283 and 252 aa, respectively, and C-terminal repeats domains were composed of 297 and 232 aa, respectively. After cloning of these genes, the present inventors have expressed six different recombinant proteins (Coa-whole, Coa-N, Coa-C, vWbp-whole, vWbp-N and vWbp-C) and then purified to homogeneity as shown FIG. 28. These proteins were used to raise rabbit polyclonal anti-Coa and vWbp-recognizing IgGs by two times immunization via subcutaneous injection. As a result of examining the antigen recognition specificity of IgG of each purified protein, anti-Coa$^{whole}$-IgG recognized Coa$^{whole}$, Coa$^{N}$, and Coa$^{C}$, whereas anti-Coa$^{N}$-IgG recognized only Coa$^{whole}$ and Coa$^{N}$, and did not recognize Coa$^{C}$ (FIG. 29*a*). In addition, anti-vWbp-IgGs are also showed specific binding to their antigens (FIG. 29*b*). These results indicate that the four generated Coa and vWbp-IgGs have specificities against their antigens.

Expression Patterns of Coa and vWbp Proteins During *S. aureus* USA300 Culture

Since all six proteins and their rabbit polyclonal antibodies were obtained, the expression patterns of these two secreted enzymes were examined by Western blot analysis using collected cultured RPMI medium of *S. aureus* USA300 strain at different time points. As shown in FIG. 30*a*, Ccoa$^{whole}$ protein (60 kDa) was secreted from 1.5-hOUR culture, maximally detected at 3-hOUR culture and then detected until 9 hours with gradually decreased amounts. As expected, *S. aureus* protein A (45 kDa) was accumulated on culture supernatant until 3-hour incubation (red arrow). However, vWbp (50 kDa) was maximally detected at 1.5-hour culture and detected until 12 hours with gradually decreased amounts (FIG. 30*b*). Protein A secretion showed a pattern similar to that of Coa (FIG. 30*b*). These results suggest that Coa$^{whole}$ and vWbp$^{whole}$ proteins were secreted maximally between 1.5 hours and 3 hours.

Identification of Coa and vWbp-Recognition Proteins Expressed on the *S. aureus* Cell Surface The present inventors tried to screen the Coa and vWbp recognizing proteins that are expressed on the bacterial surface during bacterial growth. First, *S. aureus* cell-wall associated proteins (CWAP) were targeted as recognition molecules of these two secreted enzymes. The present inventors used the seven recombinant CWAP proteins for screening of coa- and vWbp-recognizing proteins by dot blot immuno-assay (FIG. 31). After spotting these seven CWAP proteins and BSA as a control onto the PVDF membrane strips, each strip was co-incubated with six different purified recombinant Coa and vWbp domain proteins, and then each strip was incubated with each domain-specific IgGc to examine which Coa- or vWbp domain protein can bind CWAP$^{N2N3}$ proteins. As shown in FIG. 31*a*, Coa$^{whole}$ protein, Coa$^{N}$, and Coa$^{C}$ proteins specifically recognized both FnbpA$^{N2N3}$ and FnbpB$^{N2N3}$ domains. Under the same conditions, $vWbp^{whole}$ proteins showed binding abilities against five different N2-N3 domains ($ClfB^{N2N3}$, $SdrC^{N2N3}$, $SdrE^{N2N3}$, $FnbpA^{N2N3}$ and $FnbpB^{N2N3}$ domains) and $vWbp^{N}$ domain showed strong binding to $FnbpA^{N2N3}$ and weak binding to three other CWAP proteins (FIG. 31*b*). However, vWbp-C proteins showed broader binding abilities to six N2-N3 domains of CWAP proteins except for $ClfA^{N2N3}$ and $SdrD^{N2N3}$. These results suggest that Coa proteins may recognize Fnbp proteins that are expressed on the *S. aureus* bacterial surface, indicating that two *S. aureus* Fnbp CWAP proteins may functions as Coa-recognition proteins. However, vWbp proteins are more broadly recognized by several *S. aureus* CWAPs.

Confirmation of Binding Specificity Between Coa and Fnbp Proteins Using Anti-Fnbp-F(ab)2' Fragments Next, the present inventors observed the specific binding between coa proteins and two $Fnbp^{N2N3}$ proteins, the present inventors tried to confirm this specific interaction using *S. aureus* USA300 live bacteria, $Coa^{whole}$ and anti-Fnbp-F $(ab')_2$ fragments. The reason for preparation of anti-Fnbp-F $(ab')_2$ fragments is that since *S. aureus* protein A is well-known to consume added IgGs by binding to IgG Fc domain, the present inventors expected that anti-Fnbp-IgGs will not sufficiently inhibit the interaction between $Coa^{whole}$ and naïve Fnbp proteins of USA300 cells. By using anti-Fnbp-$F(ab')_2$ fragments, the present inventors assumed that it will be possible to see whether the binding between Coa and two $Fnbp^{N2N3}$ proteins is specific or not. As shown in FIG. 32, when *S. aureus* cells were co-incubated with $Coa^{C}$ protein or the mixture of $Coa^{C}$ anti-SdrC-$F(ab')_2$ fragment, $Coa^{C}$-proteins were recruited on the bacterial pellet (lanes 1 and 2). However, when bacterial cells were incubated with $Coa^{C}$ and either anti-$FnbpA^{N2N3}$-$F(ab')_2$ fragment or anti-$FnbpB^{N2N3}$-$F(ab')_2$ fragment, added $Coa^{C}$ was not recruited on the bacterial pellet (lanes 3 and 4), indicating that the interaction between naïve Fnbp proteins expressed on bacterial surface and $Coa^{C}$ proteins were specifically inhibited by the anti-Fnbp-$F(ab')_2$ fragments. These results support that Coa protein recognizes the FNBP proteins expressed on the bacterial surface.

Induction of Blood Coagulation by $Coa^{whole}$ or $vWbp^{whole}$ and Blood Coagulation Inhibitory Effects of Anti-$Coa^{whole}$-IgG and $vWbp^{whole}$-IgGs Next, the present inventors have tried to examine the biological functions of the recombinant $Coa^{whole}$ and $vWbp^{whole}$ using human whole blood. When the human blood was incubated with different doses of $Coa^{whole}$ protein, blood was coagulated by addition of 1 μg of $Coa^{whole}$ protein, but the blood was clotted by addition of 5 μg of $vWbp^{whole}$ (FIG. 33*a*), indicating that purified recombinant $Coa^{whole}$ and $vWbp^{whole}$ proteins are functionally active proteins. Next, the present inventors examined the effects of the anti-$coa^{whole}$-IgG and anti-$vWbp^{whole}$-IgGs on the Coa- and vWbp-mediated blood coagulation (FIG. 33*b*). When 80 μg of anti-$Coa^{whole}$-IgG or 80 μg of anti-$vWbp^{whole}$-IgG was added to the mixture of human blood and 5 μg of $Coa^{whole}$ or $vWbp^{whole}$ proteins, enzymes-mediated blood coagulations were inhibited. These results suggest that generated anti-$Coa^{whole}$- and $vWbp^{whole}$-IgGs can inhibit the $Coa^{whole}$- or $vWbp^{whole}$-protein-mediated blood coagulation reactions in vitro.

USA300 Culture Media-Mediated Human Blood Coagulation Can Be Inhibited by Anti-$Coa^{whole}$-IgG and anti-$vWbp^{whole}$-IgG As shown in FIG. 30, the present inventors already detected secreted Coa and vWbp upon culture of *S. aureus* 300 LAC cells. Thus, the present inventors examined whether secreted Coa and vWbp-mediated blood coagulation can be blocked by anti-$Coa^{whole}$-IgG and anti-$vWbp^{whole}$-IgG. When 200 μl of human whole blood was incubated with 100 μl of USA300 culture medium (containing approximately 0.5 μg of Coa and 0.5 μg of vWbp proteins, blood was clotted after 1.5 hours of incubation (FIG. 34, tube 4). Under this condition, when 80 μg of purified anti-$Coa^{whole}$-IgG or anti-$vWbp^{whole}$-IgG was added, blood was not clotted (tubes 6 and 7). Also, when each 40 μg of anti-$Coa^{whole}$-IgG or 40 μg of anti-$vWbp^{whole}$-IgG were added to Coa- or vWbp-containing blood, clotting was induced (tube 8). These results demonstrate that clotting activities of secreted Coa or vWbp from live bacteria were inhibited by added IgGs.

$Coa^{N}$ and $vWbp^{N}$ Domains Only Induced Human Blood Coagulation, but Not by $Coa^{C}$ and $vWbp^{C}$ Proteins To determine which domains of Coa and vWbp proteins are involved in human blood coagulation, whole blood was incubated with four different proteins ($Coa^{N}$, $vWbp^{N}$, $Coa^{C}$ and $vWbp^{C}$). When blood clotting was examined after 1.5 hours of incubation, two N-terminal domains, $Coa^{N}$ and $vWbp^{N}$, induced blood clotting, but two C-terminal domains did not induce blood clotting (FIG. 35). These results show that pro-thrombin-binding N-terminal domains, not fibrinogen-binding C-terminal domains, are essential for human blood coagulation.

$Coa^{N}$ and $vWbp^{N}$-Mediated Human Blood Coagulation or Blood Coagulation by Secreted Coa and vWbp from USA300 were Inhibited by Ant-$iCoa^{N}$-IgG and anti-$vWbp^{N}$-IgG, but Not Anti-$Coa^{C}$ and Anti-$vWbp^{C}$ IgGs Next, since the present inventors have observed the importance of $Coa^{N}$ or $vWbp^{N}$ for blood coagulation, the present inventors used two trigger proteins to examine whether anti-$Coa^{N}$- or $vWbp^{N}$-specific IgGs could these protein-mediated clotting. One trigger protein was Coa and vWbp contained in USA300 cultured medium (FIG. 36*a*), and purified recombinant $Coa^{N}$ oR $vWbp^{N}$ was as a second trigger (FIG. 36*b*). When anti-$Coa^{N}$-IgG or anti-$vWbp^{N}$-IgG were added to the tube containing culture media and blood (tube 2), clotting was not induced (tubes 3 and 4), but clotting was induced by addition of anti-$Coa^{C}$-IgG or anti-$vWbp^{C}$-IgG (tubes 5 and 6). Also, $Coa^{N}$ and $vWbp^{N}$-mediated human blood coagulations were inhibited by anti-$Coa^{N}$-IgG and anti-$vWbp^{N}$-IgG (FIG. 36*b*, tubes 4 and 5). These results show that anti-$Coa^{N}$-IgG and anti-$vWbp^{N}$-IgG will be invaluable molecules for prevention of Coa or vWbp-mediated human coagulation during *S. aureus* infection.

Blood Coagulation Inhibitory Effects of Anti-$Coa^{whole}$-IgG or $vWbp^{whole}$-IgG in vivo The present inventors have found that $Coa^{whole}$, $vWbp^{whole}$, $Coa^{N}$, and $vWbp^{N}$ domains have human blood coagulation-inducing activity, and that each polyclonal antibody obtained by immunizing rabbits with these four proteins selectively inhibits blood coagulation reactions caused by these proteins. Thus, the present inventors conducted an in vivo passive immunity using antibodies obtained by injecting $Coa^{whole}$ and $vWbp^{whole}$ proteins into rabbits.

Among four rabbits, two rabbits of a first group were injected with PBS and then injected with the *S. aureus* USA300 strain ($1.6\times10^{8}$ CFUs) via the ear vein, and two rabbits of a second group were injected with a mixture of 1 mg of anti-$Coa^{whole}$-IgG (obtained by purification with $Coa^{whole}$ protein-conjugated Sepharose column) and 1 mg of anti-$vWbp^{whole}$-IgG (obtained by purification with $vWbp^{whole}$ protein-conjugated Sepharose column) via the left ear vein, and after 1 hour, injected with the USA300 strain ($1.6\times10^{8}$ CFUs) via the right ear vein.

TABLE 4

| Constitution of rabbit groups for in vivo experiment | | | |
|---|---|---|---|
| Group | Rabbit No. | Body weight (g) | USA 300 number |
| Saline | 1 | 3180 | $1.6 \times 10^8$/100 μl |
| | 4 | 3005 | |
| Anti-Coa$^{whole}$-IgG + | 2 | 3220 | |
| anti-vWbp$^{whole}$-IgG | 3 | 2980 | |

As a result of measuring the body weight of each rabbit at 12-hour intervals, rabbit No. 1 in group 1 died after 138 hours, but all rabbits in group 2 survived up to 167 hours and showed the smallest weight loss (FIG. 38). As a result of calculating the survival rate based on these measurement results, the rabbits (Nos. 2 and 3) in group 2 injected with anti-Coa$^{whole}$-IgG and anti-vWbp$^{whole}$-IgG (each 1 mg) survived for 7 days and showed the smallest weight loss (FIG. 39). From these results, the blood coagulation inhibitory effect of anti-Coa-IgG and anti-vWbp-IgG confirmed in vitro could be confirmed again in vivo.

Example 4: Confirmation of Effect of Co-Administration with Antibiotic

In order to maximize the MRSA infectious disease treatment effect of the combination of the four *Staphylococcus aureus*-derived toxins discovered in Example 1, the present inventors explored an optimal antibiotic that can completely remove the residual MRSA strain in the kidneys of infected individuals when co-administered with the toxins. As a result, as described later, the present inventors confirmed that, when vancomycin and teicoplanin were co-administered with the vaccine composition of the present invention, there was a remarkable synergistic effect.

4-1: Vancomycin

Experimental Methods

First, a total of 80 μg of four antigens (HlgA, LukS, Hla$_{H35L}$, and LukA$_{E323A}$B) (20 μg for each antigen) was dissolved in 250 μl of saline, mixed with the same volume of alum adjuvant, incubated for 1 hour, and then intramuscularly injected 3 times at 2-week intervals. Two weeks later, sera were collected from the five immunized rabbits, and total IgG in the sera was separated and purified using a protein A column. The purified total IgG was injected intravenously into rabbits at a concentration of 10 mg/kg/rabbit, and then vancomycin (7.5 mg/kg/rabbit) was injected intramuscularly into the rabbits. Next, the rabbits were infected with the *S. aureus* USA300 MRSA strain ($1\times10^9$ cells/rabbit), and the survival rate of the rabbits, the number of residual bacteria in the kidney, and the abscess patterns created in the kidney were examined for 15 days.

A total of 20 rabbits (New Zealand White) were divided into 4 groups, each consisting of 5 rabbits. For group 1 (G1-Alum-IgG injection), polyclonal IgG purified by a protein-A column from the sera of rabbits injected with alum alone was injected intravenously into rabbits at a dose of 10 mg/kg, and then the rabbits were infected with the *S. aureus* USA300 strain at $1\times10^9$ CFUs/rabbit.

For group 2 (G2-anti-4 antigen-IgG-mixture injection), a polyclonal IgG obtained by dissolving a total of 80 μg of 4 antigens (HlgA, LukS, Hla$_{H35L}$ and LukA$_{E323A}$) (20 μg for each antigen) in 250 μl of saline, mixing the antigen solution with the same volume of alum, immunizing rabbits by intramuscular injection of the mixture three times at 2-week intervals, and purifying IgGs for these antigens from the sera of the rabbits by a protein-A column was injected intravenously into five rabbits at a dose of 10 mg/kg, and then the rabbits were infected with the *S. aureus* USA300 strain at $1\times10^9$ CFUs/rabbit.

For group 3 (injection of G3-vancomycin alone), vancomycin was injected intramuscularly into five rabbits at a dose of 7.5 mg/kg twice a day for 5 days (a total of 10 times), and then the rabbits were injected with the *S. aureus* USA300 at $1\times10^9$ CFUs/rabbit.

For group 4 (G4-anti-4 antigen-IgG-mixture-vancomycin injection), a polyclonal IgG obtained by purifying IgGs using a protein-A column from the sera obtained after antigen immunization in the same manner as in group 2 was injected intravenously into rabbits at a dose of 10 mg/kg, and then the rabbits were injected intramuscularly with vancomycin at a dose of 7.5 mg/kg twice a day for 5 days (a total of 10 times) and then infected with the *S. aureus* USA300 strain at $1\times10^9$ CFUs/rabbit.

After the four groups were infected with the *S. aureus* USA300 MRSA strain, the rabbits were weighed daily and the weight change was observed until day 14. On day 15, the rabbits were euthanized, the kidneys were harvested, and abscesses created and residual bacteria (colony forming units, CFUs) in the kidneys were measured.

Experimental Results

As a result of examining the survival rate of rabbits in each group for 2 weeks after infection with MRSA, as shown in FIG. 40*a*, 5 rabbits in group 4 (G4-anti-4 antigen-IgG-mixture-vancomycin injection) survived 100%, whereas, in group 3 (G3-injected with vancomycin alone), one rabbit died on day 3 and one rabbit died on day 5, indicating a survival rate of 60%, and in group 1 (G1) injected with alum alone, all 5 rabbits died by day 3, indicating a survival rate of 0%. In group 2 (G2-anti-4 antigen-IgG-mixture injection) injected with only antibodies purified from the rabbits immunized with the four antigens, 2 rabbits died on day 3 and 2 rabbits died on day 4, indicating a survival rate of 20% until day 14. From the above results, it could be seen that a remarkably improved therapeutic effect was exhibited when vancomycin was co-administered with the antibody mixture induced by the four antigens discovered in the present invention.

As a result of harvesting and observing the kidneys from the rabbits of groups 2 and 4, abscesses were observed in the kidneys from 4 dead rabbits out of the five rabbits of group 2, whereas no abscesses were observed in the kidneys from the five rabbits of group 4 (FIG. 40*b*). From these results, it was confirmed that the antibodies against the four *Staphylococcus aureus*-derived toxin antigens protected immune cells by neutralizing the toxins secreted during MRSA infection, but when they were co-administered with vancomycin, they could protect the host in various ways while more completely removing the bacteria.

4-2: Teicoplanin

Experimental Methods

A total of 20 rabbits (New Zealand white) were divided into 4 groups, each consisting of 5 rabbits. 10 rabbits immunized with four vaccines 3 times at 2-week intervals were divided into two groups. For five rabbits of group 2 (G2), the survival rate for 7 days after immunization with the USA300 MRSA strain, the number of residual bacteria in the kidneys, and the patterns of abscesses created in the kidneys were examined, and the remaining 5 rabbits of group 4 (G4) were infected with the USA300 MRSA strain in the same manner as G2, and after 3 hours, injected intramuscularly with teicoplanin. The remaining 10 rabbits were divided into group 1 (G1) (consisting of five rabbits) injected with saline alone and group 3 (G3) injected with teicoplanin alone.

Group 1 (G1-injected with saline alone) was injected with saline alone three times at 2-week intervals and infected with the *S. aureus* USA300 strain at $8.5\times10^7$ CFUs/kg.

For group 2 (G2-immunized with 4 antigen-mixture three times), a mixture of four antigens [HlgA (40 μg/rabbit), LukS (30 μg/rabbit), $Hla_{H35L}$ (25 μg/rabbit) and $LukA_{E323A}$ (40 μg/rabbit)] was dissolved in 135 μl of saline and mixed with 135 μl of alum, and then the rabbits were immunized with the antigen mixture by intramuscular injection three times at 2-week intervals. After 7 days when the serum IgG titer sufficiently increased, the rabbits were infected with the *S. aureus* USA300 strain at a concentration of $8.5\times10^7$ CFUs/kg.

For group 3 (G3-injected with teicoplanin alone), five rabbits were infected intramuscularly with the *S. aureus* USA300 strain at a concentration of $8.5\times10^7$ CFUs/kg, and after 3 hours, intramuscularly injected once with teicoplanin at 7.5 mg/kg.

For group 4 (G4-anti-4 antigen-IgG-mixture-teicoplanin injection), rabbits were immunized with the four antigens (HlgA, LukS, $Hla_{H35L}$ and $LukA_{E323A}$) three times at 2-week intervals in the same manner as group 2. After 7 days, when the serum IgG titer sufficiently increased, the rabbits were infected with the *S. aureus* USA300 strain at a concentration of $8.5\times10^7$ CFUs/kg, and after 3 hours, intramuscularly injected once with teicoplanin at 7.5 mg/kg.

After the rabbits of groups 2 and 4 were immunized with the antigens, blood was collected every week, and the IgG titers against the four antigens were quantified by ELISA. 7 days after 3 immunizations, the rabbits were infected with the *S. aureus* USA300 MRSA strain and weighed every day, and the weight changes were observed until day 7. On day 7, the rabbits were euthanized, the kidneys were harvested, and abscesses created and residual bacteria (colony forming units, CFUs) in the kidneys were measured.

Experimental Results

The rabbit blood was collected weekly while immunizing the four-antigen mixture three times, and the IgG titer against each antigen in the serum was measured (FIG. 41*a*). As shown in the antibody titer of group 2 (FIG. 41*a*(*i*)) and the antibody titer of group 4 (FIG. 41*a*(*i*)), each antigen uniformly induced antibody generation, and the IgG titer was kept constant. The antibody titer slightly decreased on day 42 after the second immunization, but increased again on day 49 after the third immunization, and thus the rabbits were infected with the USA300 MRSA strain. The ELISA results shown in FIG. 42*a-ii* indicate the average values of the five rabbits for the antibody titers produced in the sera from the five rabbits of group 4. It could be seen that the IgG values were measured in patterns almost similar to those of group 2, and the IgG value against each antigen increased after 3 immunizations.

As a result of examining the survival rate of rabbits in each group for 7 days after infection with MRSA, the 10 rabbits of group 3 (G3-injection with teicoplanin alone) and group 4 (G4-injection with the 4-antigen mixture 3 times at 2-week intervals, followed by infection with USA300 MRSA, followed by intramuscular injection of teicoplanin) survived 100% until day 7, whereas, in group 2 (G2-immunized with the 4-antigen mixture three times), one rabbit died on day 1 and one rabbit died on day 5 after infection with USA300 MRSA, indicating a survival rate of 60%, and in group 1 (G1) injected with PBS alone, one rabbit on day 1, two rabbits on day 4, and one rabbit on day 7 died, indicating a survival rate of only 20%. Taken together, these results demonstrate that the survival rate of individuals infected with MRSA is remarkably increased when teicoplanin is co-administered with the four-antigen mixture of the present invention, which induce efficient active immunity.

FIG. 41*c* shows the results of counting the number of residual bacteria (CFU value) remaining after mincing live rabbit kidneys. Group 2 injected with the mixture of four antigens three times at 2-week intervals and group 3 injected with teicoplanin alone each showed a statistically significant decrease in the number of residual bacteria in the kidneys compared to group 1 injected with PBS alone, and group 4 (G4), to which teicoplanin was co-administered with the four antigens, showed an about 100-fold decrease on average in the number of residual bacteria compared to group 1.

The results of harvesting and observing live rabbit kidneys from each group up to day 7 are shown in FIG. 41*d*. In the kidneys from the rabbits of groups 3 and 4, which showed similar survival rates, abscesses were observed in the kidneys of rabbit No. 12 among the six rabbits of group 3, and the color of the kidneys of rabbit No. 13 changed to black. On the other hand, abscesses were not observed in the kidneys from the 6 rabbits of group 4 except for rabbit No. 6. Meanwhile, in group 1 injected with PBS alone, the kidneys from rabbit No. 2 were harvested from the dead rabbit, and the kidneys from rabbit No. 3 were kidneys from the surviving rabbit, and these kidneys all had abscesses.

As described above, the four antigens discovered in the present invention are a minimal combination of antigens and can thoroughly inhibit cell lysis caused by 11 toxins of *Staphylococcus aureus*. In addition to the excellent therapeutic effect of this combination of antigens, the present inventors have found that, when this antigen combination is co-administered with vancomycin, teicoplanin, or a combination thereof in order to completely remove even bacteria remaining in the kidneys of infected individuals, bacteria remaining in the kidneys of infected individuals can be almost completely removed, and the survival rate of the infected individuals can also be further improved.

Although the present invention has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereto.

The invention claimed is:

1. A composition comprising: *Staphylococcus aureus* toxins comprising alpha-hemolysin mutant H35L ($Hla_{H35L}$) Leukocidal toxin S (LukS), Leukocidal toxin $A_{E323A}B$ ($LukA_{E323A}B$), and gamma-hemolysin (HlgA).

2. The composition according to claim 1, wherein the composition further contains a glycopeptide-based antibiotic.

3. The composition according to claim 2, wherein the glycopeptide-based antibiotic is selected from the group consisting of vancomycin, teicoplanin, and a combination thereof.

4. A method for preventing or treating *Staphylococcus aureus* infectious disease comprising co-administering the composition according to claim 1 with a glycopeptide-based antibiotic.

5. The method according to claim 4, wherein the glycopeptide-based antibiotic is selected from the group consisting of vancomycin, teicoplanin and a combination thereof.

6. A method for preventing or treating *Staphylococcus aureus* infectious disease comprising administering to a subject in need thereof a composition according to claim 1.

7. A method for preventing or treating *Staphylococcus aureus* infectious disease comprising administering to a subject in need thereof a composition according to claim 2.

* * * * *